(12) United States Patent
Ganz et al.

(10) Patent No.: US 9,896,481 B2
(45) Date of Patent: *Feb. 20, 2018

(54) MODIFIED MINI-HEPCIDIN PEPTIDES AND METHODS OF USING THEREOF

(71) Applicant: The Regents of the University of California, Oakland, CA (US)

(72) Inventors: Tomas Ganz, Los Angeles, CA (US); Elizabeta Nemeth, Sherman Oaks, CA (US); Piotr Ruchala, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/082,158

(22) Filed: Mar. 28, 2016

(65) Prior Publication Data

US 2016/0200765 A1   Jul. 14, 2016

Related U.S. Application Data

(63) Continuation of application No. 14/363,012, filed as application No. PCT/US2012/068180 on Dec. 6, 2012, now Pat. No. 9,328,140.

(60) Provisional application No. 61/568,724, filed on Dec. 9, 2011.

(51) Int. Cl.
| | |
|---|---|
| A61K 38/10 | (2006.01) |
| C07K 7/06 | (2006.01) |
| A61K 38/04 | (2006.01) |
| C07K 14/575 | (2006.01) |
| C07K 14/47 | (2006.01) |
| C07K 16/00 | (2006.01) |
| A61K 38/00 | (2006.01) |

(52) U.S. Cl.
CPC ............... *C07K 7/06* (2013.01); *A61K 38/04* (2013.01); *C07K 14/47* (2013.01); *C07K 14/575* (2013.01); *C07K 16/00* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,758,550 A * | 7/1988 | Cardinaux ........... | C07K 14/585 514/11.9 |
| 8,435,941 B2 | 5/2013 | Ganz et al. | |
| 2008/0213277 A1 | 9/2008 | Sasu et al. | |
| 2011/0183362 A1 | 7/2011 | Lauth et al. | |
| 2013/0203662 A1 | 8/2013 | Ganz et al. | |

FOREIGN PATENT DOCUMENTS

| | | |
|---|---|---|
| CN | 102245626 A | 11/2011 |
| WO | 2010065815 A2 | 6/2010 |
| WO | 2013086143 A1 | 6/2013 |
| WO | 2014145561 A2 | 9/2014 |

OTHER PUBLICATIONS

"Communication pursuant to Article 94(3) EPC received in EP 12856566.0", Sep. 16, 2016.
"Notice for Reasons for Rejection received in JP 2014-546062", dated Oct. 4, 2016.
Examination Report No. 1 received in AU 2012327226, dated Feb. 27, 2015.
Carstens, Bodil Borte, "The analysis of the interaction between hepcidin and ferroportion, Master Thesis, Division of Chemical and Structural Biology", May 1, 2009, Publisher: The Institute for Molecular Bioscience at the University of Queensland.
English translation of First Office Action received in CN201280064227.1, dated Nov. 17, 2015, and received Dec. 10, 2015.
Preza, et al., "Minihepcidins are rationally designed small peptides that mimic hepcidin activity in mice and may be useful for the treatment of iron overload", Nov. 1, 2011, pp. 4880-4888, vol. 121, No. 12, Publisher: J Clin Invest.
Supplementary European Search Report received in EP 12856566.0, dated Jun. 10, 2015.
Hunter, et al., "The solution structure of human hepcidin, a peptide hormone with antimicrobial activity that is involved in iron uptake and hereditary hemochromatosis", Jul. 22, 2002, pp. 37597-37603, vol. 277, No. 40, Publisher: J Biol Chem.
International Search Report received in PCT/US2012/068180, dated Apr. 1, 2013.
Betts & Russell, "Amino Acid Properties and Consequences of Substitutions", 2003, pp. 289-316, Publisher: Bioinff.mnatics for Geneticists. Ed. Barnes and Gray, John Wiley & Sons, Ltd.
Bracher, et al., "The Relative Rates of Thiol- Thioester Exchange and Hydrolysis for Alkyl and Aryl Thioalkanoates in Water", Jul. 5, 2011, pp. 399-412, vol. 41, Publisher: Orig Life Evol 13iosph.
Burgess, A., "Designing anlino acids to determine the loeal conformations of Peptides", Mar. 1994, pp. 2649-2653, vol. 91, Publisher: PNAS USA.
Clark, et al., "Understanding the Structure/Activity Relationships of the Iron Regulatory Peptide Hepcidin", Mar. 25, 2011, pp. 336-343, vol. 18, No. 3, Publisher: Chem Biol.
Clark, et al., "Design, Synthesis, and Characterization of Cyclic Analogues of the Iron Regulatory Peptide Hormone Hepcidin", Jul. 29, 2013, pp. 519-526, vol. 100, No. 5, Publisher: Peptide Science.
Fernandes, et al., "The n1olecular basis of hepcid:in-resistant hereditary hemochromatosis", Jul. 9, 2009, pp. 437-443, vol. 114, No. 2, Publisher: Blood.
Fung, et al., "Thiol-derivatized minihepddins retain biological activity", Jan. 6, 2015, pp. 763-766, vol. 25, Publisher: Bioorganic & Medicinal Chemistry Letters.
Janecka, et al., "Structural studies of position 2 modified endomorphin-2 analogs by NMR spectroscopy and molecular modeling", 2009, pp. 1293-1307 (Abstract), vol. 83, No. 7, Publisher: Polish Journal of Chemistry.
Malesevic, et al., "Spectroscopic detection of pseudo-turns in homodetic cyclic penta- and hexapeptidcs comprising beta-homoproline", 2006, pp. 165-177 (Abstract), vol. 12, No. 2, Publisher: Internat'l J of Peptide Research and Therapeutics.

(Continued)

*Primary Examiner* — Fred H Reynolds
(74) *Attorney, Agent, or Firm* — Suzannah K. Sundy, Esq.; Canady + Lortz LLP

(57) ABSTRACT

Disclosed herein are peptides which exhibit hepcidin activity and methods of making and using thereof.

18 Claims, 19 Drawing Sheets

(56) References Cited

OTHER PUBLICATIONS

Pegoraro and Moroder, "6.4 Synthesis of Lipopeptides", May 14, 2014, pp. 333-374, Publisher: Houben-Weyl Methods of Organic Chemistry vol. E 22b, 4th Edition Supplement: Synthesis of Peptides and Peptidomimetics.

Preza, et al., "Cellular Catabolism of the Iron-Regulatory Peptide Hormone Hepcidin", Mar. 2013, p. e.58934, vol. 8, No. 3, Publisher: PLoS ONE.

Ramos, et al., ".Nfinihepcidins prevent iron overload in a hepcidin-deficient mouse model of severe hemochromatosis", Nov. 1, 2012, pp. 3829-3836, vol. 120, No. 18, Publisher: Blood.

Rijkers, et al., "A convenient solid phase synthesis of S-palmitoyl transmembrane peptides", Apr. 1, 2005, pp. 3341-3345, vol. 46, Publisher: Tetrahedron Letters.

Singh and Whitesides, "Thiol-disulfide interchange", 1993, pp. 633-658, Publisher: Eds S. Patai and Z. Rappoport, John Wiley & Sons, Inc.

Yousefi-Salakdeh, et al., "A method for S- and 0-palmitoylation of peptides: synthesis of pulmonary surfactant protein-C models", 1990, pp. 557-562, vol. 343, Publisher: Biochem J.

\* cited by examiner

SEQUENCE LISTING

```
<160> NUMBER OF SEQ ID NOS: 101

<210> SEQ ID NO 1
<211> LENGTH: 25
<212> TYPE: PRT
<213> ORGANISM: Homo sapiens

<400> SEQUENCE: 1

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 2
<211> LENGTH: 10
<212> TYPE: PRT
<213> ORGANISM: Artificial Sequence
<220> FEATURE:
<223> OTHER INFORMATION: Based on Homo sapiens sequence

<400> SEQUENCE: 2

Asp Thr His Phe Pro Ile Cys Ile Phe Cys
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Based on Homo sapiens sequence
```

```
<400> SEQUENCE: 3

Phe Pro Ile Cys
1

<210> SEQ ID NO 4
<211> LENGTH: 5
<212> TYPE: PRT
<213> ORGANISM: Artificial Sequence
<220> FEATURE:
<223> OTHER INFORMATION: Based on Homo sapiens sequence

<400> SEQUENCE: 4

His Phe Pro Ile Cys
1               5

<210> SEQ ID NO 5
<211> LENGTH: 6
<212> TYPE: PRT
<213> ORGANISM: Artificial Sequence
<220> FEATURE:
<223> OTHER INFORMATION: Based on Homo sapiens sequence

<400> SEQUENCE: 5

His Phe Pro Ile Cys Ile
1               5

<210> SEQ ID NO 6
<211> LENGTH: 7
<212> TYPE: PRT
<213> ORGANISM: Artificial Sequence
<220> FEATURE:
<223> OTHER INFORMATION: Based on Homo sapiens sequence

<400> SEQUENCE: 6

His Phe Pro Ile Cys Ile Phe
1               5

<210> SEQ ID NO 7
<211> LENGTH: 7
<212> TYPE: PRT
<213> ORGANISM: Artificial Sequence
<220> FEATURE:
<223> OTHER INFORMATION: Based on Homo sapiens sequence

<400> SEQUENCE: 7

Asp Thr His Phe Pro Ile Cys
1               5

<210> SEQ ID NO 8
<211> LENGTH: 8
<212> TYPE: PRT
<213> ORGANISM: Artificial Sequence
<220> FEATURE:
<223> OTHER INFORMATION: Based on Homo sapiens sequence

<400> SEQUENCE: 8

Asp Thr His Phe Pro Ile Cys Ile
1               5

<210> SEQ ID NO 9
<211> LENGTH: 9
<212> TYPE: PRT
<213> ORGANISM: Artificial Sequence
<220> FEATURE:
<223> OTHER INFORMATION: Based on Homo sapiens sequence
```

```
<400> SEQUENCE: 9

Asp Thr His Phe Pro Ile Cys Ile Phe
1               5

<210> SEQ ID NO 10
<211> LENGTH: 10
<212> TYPE: PRT
<213> ORGANISM: Artificial Sequence
<220> FEATURE:
<223> OTHER INFORMATION: Based on Homo sapiens sequence

<400> SEQUENCE: 10

Asp Thr His Phe Pro Ile Ala Ile Phe Cys
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Based on Homo sapiens sequence

<400> SEQUENCE: 11

Asp Thr His Ala Pro Ile Cys Ile Phe
1               5

<210> SEQ ID NO 12
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (7)..(7)
<223> OTHER INFORMATION: Xaa is S-t-butylthio-L-cysteine

<400> SEQUENCE: 12

Asp Thr His Ala Pro Ile Xaa Ile Phe
1               5

<210> SEQ ID NO 13
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (7)..(7)
<223> OTHER INFORMATION: Xaa is t-butylthio-L-cysteine

<400> SEQUENCE: 13

Asp Thr His Ala Pro Ile Xaa Ile Phe
1               5

<210> SEQ ID NO 14
<211> LENGTH: 9
<212> TYPE: PRT
<213> ORGANISM: Artificial Sequence
<220> FEATURE:
<223> OTHER INFORMATION: Based on Homo sapiens sequence

<400> SEQUENCE: 14

Asp Thr His Phe Pro Ile Ala Ile Phe
1               5
```

-continued

```
<210> SEQ ID NO 15
<211> LENGTH: 9
<212> TYPE: PRT
<213> ORGANISM: Artificial Sequence
<220> FEATURE:
<223> OTHER INFORMATION: Based on Homo sapiens sequence

<400> SEQUENCE: 15

Asp Thr His Phe Pro Ile Ser Ile Phe
1               5

<210> SEQ ID NO 16
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (7)..(7)
<223> OTHER INFORMATION: D-amino acid

<400> SEQUENCE: 16

Asp Thr His Phe Pro Ile Cys Ile Phe
1               5

<210> SEQ ID NO 17
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (7)..(7)
<223> OTHER INFORMATION: Xaa is L-homocysteine

<400> SEQUENCE: 17

Asp Thr His Ala Pro Ile Xaa Ile Phe
1               5

<210> SEQ ID NO 18
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (7)..(7)
<223> OTHER INFORMATION: Xaa is L-penicillamine

<400> SEQUENCE: 18

Asp Thr His Ala Pro Ile Xaa Ile Phe
1               5

<210> SEQ ID NO 19
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (7)..(7)
<223> OTHER INFORMATION: Xaa is D-penicillamine

<400> SEQUENCE: 19

Asp Thr His Phe Pro Ile Xaa Ile Phe
1               5
```

<210> SEQ ID NO 20
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (7)..(7)
<223> OTHER INFORMATION: Xaa is N-(bromoacetyl)-L-2,3-diaminopropionic
      acid

<400> SEQUENCE: 20

Asp Thr His Ala Pro Ile Xaa Ile Phe
1               5

<210> SEQ ID NO 21
<211> LENGTH: 10
<212> TYPE: PRT
<213> ORGANISM: Artificial Sequence
<220> FEATURE:
<223> OTHER INFORMATION: Based on Homo sapiens
<220> FEATURE:
<221> NAME/KEY: misc_feature
<222> LOCATION: (1)..(1)
<223> OTHER INFORMATION: Amino acid residue connected by a disulfide
      link to form a cyclized structure
<220> FEATURE:
<221> NAME/KEY: misc_feature
<222> LOCATION: (8)..(8)
<223> OTHER INFORMATION: Amino acid residue connected by a disulfide
      link to form a cyclized structure

<400> SEQUENCE: 21

Cys Asp Thr His Phe Pro Ile Cys Ile Phe
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (7)..(7)
<223> OTHER INFORMATION: Amino acid residue connected by a disulfide
      link to form a cyclized structure
<220> FEATURE:
<221> NAME/KEY: misc_feature
<222> LOCATION: (9)..(9)
<223> OTHER INFORMATION: Having CONH2-CH2-CH2-S bound thereto and S
      forms a disulfide link with the amino acid residue at postiion 7

<400> SEQUENCE: 22

Asp Thr His Phe Pro Ile Cys Ile Phe
1               5

<210> SEQ ID NO 23
<211> LENGTH: 8
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Amino acid residue connected by a disulfide
      link to form a cyclized structure
<220> FEATURE:
<221> NAME/KEY: misc_feature

```
<222> LOCATION: (6)..(6)
<223> OTHER INFORMATION: Amino acid residue connected by a disulfide
      link to form a cyclized structure

<400> SEQUENCE: 23

Cys His Phe Pro Ile Cys Ile Phe
1               5

<210> SEQ ID NO 24
<211> LENGTH: 7
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (5)..(5)
<223> OTHER INFORMATION: Amino acid residue connected by a disulfide
      link to form a cyclized structure
<220> FEATURE:
<221> NAME/KEY: misc_feature
<222> LOCATION: (7)..(7)
<223> OTHER INFORMATION: Having CONH2-CH2-CH2-S bound thereto and S
      forms a disulfide link with the amino acid residue at postiion 5

<400> SEQUENCE: 24

His Phe Pro Ile Cys Ile Phe
1               5

<210> SEQ ID NO 25
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (4)..(4)
<223> OTHER INFORMATION: Xaa is L-phenylglycine
<220> FEATURE:
<221> NAME/KEY: misc_feature
<222> LOCATION: (5)..(5)
<223> OTHER INFORMATION: Xaa is octahydroindole-2-carboxylic acid
<220> FEATURE:
<221> NAME/KEY: misc_feature
<222> LOCATION: (6)..(6)
<223> OTHER INFORMATION: Xaa is L-alpha-cyclohexylglycine
<220> FEATURE:
<221> NAME/KEY: misc_feature
<222> LOCATION: (8)..(8)
<223> OTHER INFORMATION: Xaa is L-alpha-cyclohexylglycine

<400> SEQUENCE: 25

Asp Xaa His Xaa Xaa Xaa Cys Xaa Phe
1               5

<210> SEQ ID NO 26
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (2)..(2)
<223> OTHER INFORMATION: Xaa is L-tert-leucine
<220> FEATURE:
<221> NAME/KEY: misc_feature
<222> LOCATION: (5)..(5)
```

```
<223> OTHER INFORMATION: Xaa is octahydroindole-2-carboxylic acid
<220> FEATURE:
<221> NAME/KEY: misc_feature
<222> LOCATION: (6)..(6)
<223> OTHER INFORMATION: Xaa is L-alpha-cyclohexylglycine
<220> FEATURE:
<221> NAME/KEY: misc_feature
<222> LOCATION: (8)..(8)
<223> OTHER INFORMATION: Xaa is L-alpha-cyclohexylglycine

<400> SEQUENCE: 26

Asp Xaa His Pro Xaa Xaa Cys Xaa Phe
1               5

<210> SEQ ID NO 27
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino aciids

<400> SEQUENCE: 27

Phe Ile Cys Ile Pro Phe His Thr Asp
1               5

<210> SEQ ID NO 28
<211> LENGTH: 7
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(7)
<223> OTHER INFORMATION: D-amino acids

<400> SEQUENCE: 28

Phe Ile Cys Ile Pro Phe His
1               5

<210> SEQ ID NO 29
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino acids
<220> FEATURE:
<221> NAME/KEY: misc_feature
<222> LOCATION: (1)..(1)
<223> OTHER INFORMATION: Having chenodeoxycholate-(D)Asp-(PEG11)- bound
      thereto

<400> SEQUENCE: 29

Phe Ile Cys Ile Pro Phe His Thr Asp
1               5

<210> SEQ ID NO 30
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
```

```
<221> NAME/KEY: misc_feature
<222> LOCATION: (1)..(9)
<223> OTHER INFORMATION: D-amino acids
<220> FEATURE:
<221> NAME/KEY: misc_feature
<222> LOCATION: (1)..(1)
<223> OTHER INFORMATION: Having ursodeoxycholate-(D)Asp-(PEG11)- bound
      thereto

<400> SEQUENCE: 30

Phe Ile Cys Ile Pro Phe His Thr Asp
1               5

<210> SEQ ID NO 31
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino acids
<220> FEATURE:
<221> NAME/KEY: misc_feature
<222> LOCATION: (9)..(9)
<223> OTHER INFORMATION: Having -(PEG11)-GYIPEAPRDGQAYVRKDGEWVLLSTFL
      bound thereto

<400> SEQUENCE: 31

Phe Ile Cys Ile Pro Phe His Thr Asp
1               5

<210> SEQ ID NO 32
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino acids
<220> FEATURE:
<221> NAME/KEY: misc_feature
<222> LOCATION: (9)..(9)
<223> OTHER INFORMATION: Having -(PEG11)-(GPHyp)10 bound thereto

<400> SEQUENCE: 32

Phe Ile Cys Ile Pro Phe His Thr Asp
1               5

<210> SEQ ID NO 33
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino acids
<220> FEATURE:
<221> NAME/KEY: misc_feature
<222> LOCATION: (1)..(1)
<223> OTHER INFORMATION: Having palmitoyl-(PEG11)- bound thereto

<400> SEQUENCE: 33

Phe Ile Cys Ile Pro Phe His Thr Asp
1               5
```

```
<210> SEQ ID NO 34
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino acids
<220> FEATURE:
<221> NAME/KEY: misc_feature
<222> LOCATION: (1)..(1)
<223> OTHER INFORMATION: Having (Palmitoyl)2-Dap-PEG11- bound thereto

<400> SEQUENCE: 34

Phe Ile Cys Ile Pro Phe His Thr Asp
1               5

<210> SEQ ID NO 35
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (4)..(4)
<223> OTHER INFORMATION: Xaa is beta-homophenylalanine

<400> SEQUENCE: 35

Asp Thr His Xaa Pro Ile Cys Ile Phe
1               5

<210> SEQ ID NO 36
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (4)..(4)
<223> OTHER INFORMATION: Xaa is 3,3-diphenyl-L-alanine

<400> SEQUENCE: 36

Asp Thr His Xaa Pro Ile Cys Ile Phe
1               5

<210> SEQ ID NO 37
<211> LENGTH: 9
<212> TYPE: PRT
<213> ORGANISM: Artificial Sequence
<220> FEATURE:
<223> OTHER INFORMATION: Based on Homo sapien sequence
<220> FEATURE:
<221> NAME/KEY: misc_feature
<222> LOCATION: (4)..(4)
<223> OTHER INFORMATION: Xaa is L-biphenylalanine

<400> SEQUENCE: 37

Asp Thr His Xaa Pro Ile Cys Ile Phe
1               5

<210> SEQ ID NO 38
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
```

<221> NAME/KEY: misc_feature
<222> LOCATION: (4)..(4)
<223> OTHER INFORMATION: Xaa is (1-naphthyl)-L-alanine

<400> SEQUENCE: 38

Asp Thr His Xaa Pro Ile Cys Ile Phe
1               5

<210> SEQ ID NO 39
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (4)..(4)
<223> OTHER INFORMATION: Xaa is (S)-3-Amino-4,4-diphenylbutanoic acid

<400> SEQUENCE: 39

Asp Thr His Xaa Pro Ile Cys Ile Phe
1               5

<210> SEQ ID NO 40
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (9)..(9)
<223> OTHER INFORMATION: Xaa is beta-homophenylalanine

<400> SEQUENCE: 40

Asp Thr His Phe Pro Ile Cys Ile Xaa
1               5

<210> SEQ ID NO 41
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (9)..(9)
<223> OTHER INFORMATION: Xaa is 3,3-diphenyl-L-alanine

<400> SEQUENCE: 41

Asp Thr His Phe Pro Ile Cys Ile Xaa
1               5

<210> SEQ ID NO 42
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (9)..(9)
<223> OTHER INFORMATION: Xaa is L-biphenylalanine

<400> SEQUENCE: 42

Asp Thr His Phe Pro Ile Cys Ile Xaa
1               5

<210> SEQ ID NO 43

```
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (9)..(9)
<223> OTHER INFORMATION: Xaa is (1-naphthyl)-L-alanine

<400> SEQUENCE: 43

Asp Thr His Phe Pro Ile Cys Ile Xaa
1               5

<210> SEQ ID NO 44
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (9)..(9)
<223> OTHER INFORMATION: Xaa is (S)-3-Amino-4,4-diphenylbutanoic acid

<400> SEQUENCE: 44

Asp Thr His Phe Pro Ile Cys Ile Xaa
1               5

<210> SEQ ID NO 45
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (9)..(9)
<223> OTHER INFORMATION: Xaa is 3,3-diphenyl-L-alanine

<400> SEQUENCE: 45

Asp Thr His Xaa Pro Ile Cys Ile Xaa
1               5

<210> SEQ ID NO 46
<211> LENGTH: 7
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (2)..(2)
<223> OTHER INFORMATION: Xaa is 3,3-diphenyl-L-alanine

<400> SEQUENCE: 46

Asp Xaa Pro Ile Cys Ile Phe
1               5

<210> SEQ ID NO 47
<211> LENGTH: 7
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
```

```
<222> LOCATION: (2)..(2)
<223> OTHER INFORMATION: Xaa is 3,3-diphenyl-L-alanine
<220> FEATURE:
<221> NAME/KEY: misc_feature
<222> LOCATION: (7)..(7)
<223> OTHER INFORMATION: Xaa is 3,3-diphenyl-L-alanine

<400> SEQUENCE: 47

Asp Xaa Pro Ile Cys Ile Xaa
1               5

<210> SEQ ID NO 48
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (6)..(6)
<223> OTHER INFORMATION: D-amino acid
<220> FEATURE:
<221> NAME/KEY: misc_feature
<222> LOCATION: (8)..(8)
<223> OTHER INFORMATION: D-amino acid
<220> FEATURE:
<221> NAME/KEY: misc_feature
<222> LOCATION: (9)..(9)
<223> OTHER INFORMATION: Xaa is 3,3-diphenyl-L-alanine

<400> SEQUENCE: 48

Asp Thr His Xaa Pro Arg Cys Arg Xaa
1               5

<210> SEQ ID NO 49
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is octahydroindole-2-carboxylic acid

<400> SEQUENCE: 49

Asp Thr His Xaa Xaa Ile Cys Ile Phe
1               5

<210> SEQ ID NO 50
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is octahydroindole-2-carboxylic acid
<220> FEATURE:
<221> NAME/KEY: misc_feature
```

```
<222> LOCATION: (9)..(9)
<223> OTHER INFORMATION: Xaa is 3,3-diphenyl-L-alanine

<400> SEQUENCE: 50

Asp Thr His Xaa Xaa Ile Cys Ile Xaa
1               5

<210> SEQ ID NO 51
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (9)..(9)
<223> OTHER INFORMATION: Xaa is 3,3-diphenyl-L-alanine

<400> SEQUENCE: 51

Asp Thr His Xaa Pro Cys Cys Cys Xaa
1               5

<210> SEQ ID NO 52
<211> LENGTH: 12
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (10)..(10)
<223> OTHER INFORMATION: D-amino acid

<400> SEQUENCE: 52

Asp Thr His Phe Pro Ile Cys Ile Phe Pro Pro Lys
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (10)..(10)
<223> OTHER INFORMATION: D-amino acid

<400> SEQUENCE: 53

Asp Thr His Phe Pro Ile Cys Ile Phe Pro Pro Arg
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (10)..(10)
<223> OTHER INFORMATION: Xaa is L-beta-homoproline

<400> SEQUENCE: 54

Asp Thr His Phe Pro Ile Cys Ile Phe Xaa Pro Lys
1               5                   10
```

<210> SEQ ID NO 55
<211> LENGTH: 12
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (10)..(10)
<223> OTHER INFORMATION: Xaa is L-beta-homoproline

<400> SEQUENCE: 55

Asp Thr His Phe Pro Ile Cys Ile Phe Xaa Pro Arg
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (10)..(10)
<223> OTHER INFORMATION: D-amino acid
<220> FEATURE:
<221> NAME/KEY: misc_feature
<222> LOCATION: (11)..(11)
<223> OTHER INFORMATION: Xaa is L-beta-homoproline

<400> SEQUENCE: 56

Asp Thr His Phe Pro Ile Cys Ile Phe Pro Xaa Lys
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (10)..(10)
<223> OTHER INFORMATION: D-amino acid
<220> FEATURE:
<221> NAME/KEY: misc_feature
<222> LOCATION: (11)..(11)
<223> OTHER INFORMATION: Xaa is L-beta-homoproline

<400> SEQUENCE: 57

Asp Thr His Phe Pro Ile Cys Ile Phe Pro Xaa Arg
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (9)..(9)
<223> OTHER INFORMATION: Xaa is beta-homophenylalanine
<220> FEATURE:
<221> NAME/KEY: misc_feature
<222> LOCATION: (10)..(10)
<223> OTHER INFORMATION: D-amino acid

<400> SEQUENCE: 58

Asp Thr His Phe Pro Ile Cys Ile Xaa Pro Pro Lys

<210> SEQ ID NO 59
<211> LENGTH: 12
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (9)..(9)
<223> OTHER INFORMATION: Xaa is beta-homophenylalanine
<220> FEATURE:
<221> NAME/KEY: misc_feature
<222> LOCATION: (10)..(10)
<223> OTHER INFORMATION: L-amino acid
<220> FEATURE:
<221> NAME/KEY: misc_feature
<222> LOCATION: (10)..(10)
<223> OTHER INFORMATION: D-amino acid

<400> SEQUENCE: 59

Asp Thr His Phe Pro Ile Cys Ile Xaa Pro Pro Arg
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (9)..(9)
<223> OTHER INFORMATION: Xaa is beta-homophenylalanine
<220> FEATURE:
<221> NAME/KEY: misc_feature
<222> LOCATION: (10)..(10)
<223> OTHER INFORMATION: D-amino acid
<220> FEATURE:
<221> NAME/KEY: misc_feature
<222> LOCATION: (11)..(11)
<223> OTHER INFORMATION: Xaa is L-beta-homoproline

<400> SEQUENCE: 60

Asp Thr His Phe Pro Ile Cys Ile Xaa Pro Xaa Lys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (9)..(9)
<223> OTHER INFORMATION: Xaa is beta-homophenylalanine
<220> FEATURE:
<221> NAME/KEY: misc_feature
<222> LOCATION: (10)..(10)
<223> OTHER INFORMATION: D-amino acid
<220> FEATURE:
<221> NAME/KEY: misc_feature
<222> LOCATION: (11)..(11)
<223> OTHER INFORMATION: Xaa is L-beta-homoproline

<400> SEQUENCE: 61

Asp Thr His Phe Pro Ile Cys Ile Xaa Pro Xaa Arg
1               5                   10

<210> SEQ ID NO 62

```
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (2)..(2)
<223> OTHER INFORMATION: Xaa is isonipecotic acid
<220> FEATURE:
<221> NAME/KEY: misc_feature
<222> LOCATION: (3)..(3)
<223> OTHER INFORMATION: Xaa is 3,3-diphenyl-D-alanine
<220> FEATURE:
<221> NAME/KEY: misc_feature
<222> LOCATION: (4)..(4)
<223> OTHER INFORMATION: Xaa is (aminomethyl)cyclohexane carboxylic acid
<220> FEATURE:
<221> NAME/KEY: misc_feature
<222> LOCATION: (6)..(6)
<223> OTHER INFORMATION: Xaa is (aminomethyl)cyclohexane carboxylic acid
<220> FEATURE:
<221> NAME/KEY: misc_feature
<222> LOCATION: (7)..(7)
<223> OTHER INFORMATION: Xaa is isonipecotic acid
<220> FEATURE:
<221> NAME/KEY: misc_feature
<222> LOCATION: (8)..(8)
<223> OTHER INFORMATION: Xaa is 3,3-diphenyl-L-alanine
<220> FEATURE:
<221> NAME/KEY: misc_feature
<222> LOCATION: (9)..(9)
<223> OTHER INFORMATION: Xaa is cysteamide, oxidized

<400> SEQUENCE: 62

Cys Xaa Xaa Xaa Arg Xaa Xaa Xaa Xaa
1               5

<210> SEQ ID NO 63
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (3)..(3)
<223> OTHER INFORMATION: Xaa is 3,3-diphenyl-D-alanine
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa is isonipecotic acid
<220> FEATURE:
<221> NAME/KEY: misc_feature
<222> LOCATION: (8)..(8)
<223> OTHER INFORMATION: Xaa is 3,3-diphenyl-L-alanine
<220> FEATURE:
<221> NAME/KEY: misc_feature
<222> LOCATION: (9)..(9)
<223> OTHER INFORMATION: Xaa is cysteamide, oxidized

<400> SEQUENCE: 63

Cys Pro Xaa Xaa Arg Xaa Xaa Xaa Xaa
1               5

<210> SEQ ID NO 64
<211> LENGTH: 9
```

```
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (2)..(2)
<223> OTHER INFORMATION: D-amino acid
<220> FEATURE:
<221> NAME/KEY: misc_feature
<222> LOCATION: (3)..(3)
<223> OTHER INFORMATION: Xaa is 3,3-diphenyl-D-alanine
<220> FEATURE:
<221> NAME/KEY: misc_feature
<222> LOCATION: (4)..(4)
<223> OTHER INFORMATION: Xaa is (aminomethyl)cyclohexane carboxylic acid
<220> FEATURE:
<221> NAME/KEY: misc_feature
<222> LOCATION: (6)..(6)
<223> OTHER INFORMATION: Xaa is (aminomethyl)cyclohexane carboxylic acid
<220> FEATURE:
<221> NAME/KEY: misc_feature
<222> LOCATION: (7)..(7)
<223> OTHER INFORMATION: Xaa is isonipecotic acid
<220> FEATURE:
<221> NAME/KEY: misc_feature
<222> LOCATION: (8)..(8)
<223> OTHER INFORMATION: Xaa is 3,3-diphenyl-L-alanine
<220> FEATURE:
<221> NAME/KEY: misc_feature
<222> LOCATION: (9)..(9)
<223> OTHER INFORMATION: Xaa is cysteamide, oxidized

<400> SEQUENCE: 64

Cys Pro Xaa Xaa Arg Xaa Xaa Xaa Xaa
1               5

<210> SEQ ID NO 65
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (3)..(3)
<223> OTHER INFORMATION: Xaa is 3,3-diphenyl-D-alanine
<220> FEATURE:
<221> NAME/KEY: misc_feature
<222> LOCATION: (4)..(4)
<223> OTHER INFORMATION: Xaa is (aminomethyl)cyclohexane carboxylic acid
<220> FEATURE:
<221> NAME/KEY: misc_feature
<222> LOCATION: (6)..(6)
<223> OTHER INFORMATION: Xaa is (aminomethyl)cyclohexane carboxylic acid
<220> FEATURE:
<221> NAME/KEY: misc_feature
<222> LOCATION: (7)..(7)
<223> OTHER INFORMATION: Xaa is isonipecotic acid
<220> FEATURE:
<221> NAME/KEY: misc_feature
<222> LOCATION: (8)..(8)
<223> OTHER INFORMATION: Xaa is 3,3-diphenyl-L-alanine
<220> FEATURE:
<221> NAME/KEY: misc_feature
<222> LOCATION: (9)..(9)
<223> OTHER INFORMATION: Xaa is cysteamide, oxidized

<400> SEQUENCE: 65

Cys Gly Xaa Xaa Arg Xaa Xaa Xaa Xaa
1               5

<210> SEQ ID NO 66
<211> LENGTH: 27
<212> TYPE: PRT
```

<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Having -(PEG11)- bound thereto

<400> SEQUENCE: 66

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 67
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (9)..(9)
<223> OTHER INFORMATION: Xaa is 3,3-diphenyl-L-alanine

<400> SEQUENCE: 67

Asp Thr His Xaa Pro Arg Cys Arg Xaa
1               5

<210> SEQ ID NO 68
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino acids
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (9)..(9)
<223> OTHER INFORMATION: Having palmitoyl-(PEG11)- bound thereto

<400> SEQUENCE: 68

Asp Thr His Xaa Pro Ile Cys Ile Phe
1               5

<210> SEQ ID NO 69
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino acids
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature

```
<222> LOCATION: (9)..(9)
<223> OTHER INFORMATION: Having palmitoyl-(PEG11)- bound thereto
<220> FEATURE:
<221> NAME/KEY: misc_feature
<222> LOCATION: (9)..(9)
<223> OTHER INFORMATION: Xaa is 3,3-diphenyl-L-alanine

<400> SEQUENCE: 69

Asp Thr His Xaa Pro Ile Cys Ile Xaa
1               5

<210> SEQ ID NO 70
<211> LENGTH: 7
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(7)
<223> OTHER INFORMATION: D-amino acids
<220> FEATURE:
<221> NAME/KEY: misc_feature
<222> LOCATION: (2)..(2)
<223> OTHER INFORMATION: Xaa is 3,3-diphenyl-L-alanine
<220> FEATURE:
<221> NAME/KEY: misc_feature
<222> LOCATION: (7)..(7)
<223> OTHER INFORMATION: Having palmitoyl-(PEG11)- bound thereto

<400> SEQUENCE: 70

His Xaa Pro Ile Cys Ile Phe
1               5

<210> SEQ ID NO 71
<211> LENGTH: 7
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(7)
<223> OTHER INFORMATION: D-amino acids
<220> FEATURE:
<221> NAME/KEY: misc_feature
<222> LOCATION: (2)..(2)
<223> OTHER INFORMATION: Xaa is 3,3-diphenyl-L-alanine
<220> FEATURE:
<221> NAME/KEY: misc_feature
<222> LOCATION: (7)..(7)
<223> OTHER INFORMATION: Having palmitoyl-(PEG11)- bound thereto
<220> FEATURE:
<221> NAME/KEY: misc_feature
<222> LOCATION: (7)..(7)
<223> OTHER INFORMATION: Xaa is 3,3-diphenyl-L-alanine

<400> SEQUENCE: 71

His Xaa Pro Ile Cys Ile Xaa
1               5

<210> SEQ ID NO 72
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino acids
<220> FEATURE:
<221> NAME/KEY: misc_feature
```

```
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (9)..(9)
<223> OTHER INFORMATION: Having palmitoyl-(PEG11)- bound thereto

<400> SEQUENCE: 72

Asp Thr His Xaa Pro Val Cys Val Phe
1               5

<210> SEQ ID NO 73
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino acids
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (9)..(9)
<223> OTHER INFORMATION: Having palmitoyl-(PEG11)- bound thereto

<400> SEQUENCE: 73

Asp Thr His Xaa Pro Leu Cys Leu Phe
1               5

<210> SEQ ID NO 74
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is N-MeAsp
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (9)..(9)
<223> OTHER INFORMATION: Having palmitoyl-PEG-miniPEG3- bound thereto
<220> FEATURE:
<221> NAME/KEY: misc_feature
<222> LOCATION: (9)..(9)
<223> OTHER INFORMATION: Xaa is beta-homophenylalanine

<400> SEQUENCE: 74

Xaa Thr His Xaa Pro Ile Cys Ile Xaa
1               5

<210> SEQ ID NO 75
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is N-MeAsp
<220> FEATURE:
<221> NAME/KEY: misc_feature
```

```
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (9)..(9)
<223> OTHER INFORMATION: Having palmitoyl-PEG-miniPEG3- bound thereto
<220> FEATURE:
<221> NAME/KEY: misc_feature
<222> LOCATION: (9)..(9)
<223> OTHER INFORMATION: Xaa is beta-homophenylalanine

<400> SEQUENCE: 75

Xaa Thr His Xaa Xaa Ile Cys Ile Xaa
1               5

<210> SEQ ID NO 76
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is N-MeAsp
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (6)..(6)
<223> OTHER INFORMATION: Xaa is Ach
<220> FEATURE:
<221> NAME/KEY: misc_feature
<222> LOCATION: (8)..(8)
<223> OTHER INFORMATION: Xaa is Ach
<220> FEATURE:
<221> NAME/KEY: misc_feature
<222> LOCATION: (9)..(9)
<223> OTHER INFORMATION: Having palmitoyl-PEG-miniPEG3- bound thereto

<400> SEQUENCE: 76

Xaa Thr His Xaa Pro Xaa Cys Xaa Phe
1               5

<210> SEQ ID NO 77
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is N-MeAsp
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is octahydroindole-2-carboxylic acid
<220> FEATURE:
<221> NAME/KEY: misc_feature
<222> LOCATION: (9)..(9)
<223> OTHER INFORMATION: Having palmitoyl-PEG-miniPEG3- bound thereto
<220> FEATURE:
<221> NAME/KEY: misc_feature
<222> LOCATION: (9)..(9)
```

```
<223> OTHER INFORMATION: Xaa is beta-homophenylalanine

<400> SEQUENCE: 77

Xaa Thr His Xaa Xaa Arg Cys Arg Xaa
1               5

<210> SEQ ID NO 78
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is N-MeAsp
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (9)..(9)
<223> OTHER INFORMATION: Having palmitoyl-PEG-miniPEG3- bound thereto
<220> FEATURE:
<221> NAME/KEY: misc_feature
<222> LOCATION: (9)..(9)
<223> OTHER INFORMATION: Xaa is beta-homophenylalanine

<400> SEQUENCE: 78

Xaa Thr His Xaa Xaa Arg Cys Arg Xaa
1               5

<210> SEQ ID NO 79
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (9)..(9)
<223> OTHER INFORMATION: Having palmitoyl-PEG-miniPEG3- bound thereto
<220> FEATURE:
<221> NAME/KEY: misc_feature
<222> LOCATION: (9)..(9)
<223> OTHER INFORMATION: Xaa is beta-homophenylalanine

<400> SEQUENCE: 79

Xaa Thr His Xaa Pro Ile Cys Ile Xaa
1               5

<210> SEQ ID NO 80
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
```

<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (9)..(9)
<223> OTHER INFORMATION: Having palmitoyl-PEG-miniPEG3- bound thereto
<220> FEATURE:
<221> NAME/KEY: misc_feature
<222> LOCATION: (9)..(9)
<223> OTHER INFORMATION: Xaa is beta-homophenylalanine

<400> SEQUENCE: 80

Xaa Thr His Xaa Xaa Ile Cys Ile Xaa
1               5

<210> SEQ ID NO 81
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (6)..(6)
<223> OTHER INFORMATION: Xaa is Ach
<220> FEATURE:
<221> NAME/KEY: misc_feature
<222> LOCATION: (8)..(8)
<223> OTHER INFORMATION: Xaa is Ach
<220> FEATURE:
<221> NAME/KEY: misc_feature
<222> LOCATION: (9)..(9)
<223> OTHER INFORMATION: Having palmitoyl-PEG-miniPEG3- bound thereto

<400> SEQUENCE: 81

Xaa Thr His Xaa Pro Xaa Cys Xaa Phe
1               5

<210> SEQ ID NO 82
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (9)..(9)
<223> OTHER INFORMATION: Having palmitoyl-PEG-miniPEG3- bound thereto

```
<220> FEATURE:
<221> NAME/KEY: misc_feature
<222> LOCATION: (9)..(9)
<223> OTHER INFORMATION: Xaa is beta-homophenylalanine

<400> SEQUENCE: 82

Xaa Thr His Xaa Xaa Arg Cys Arg Xaa
1               5

<210> SEQ ID NO 83
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (6)..(6)
<223> OTHER INFORMATION: D-amino acid
<220> FEATURE:
<221> NAME/KEY: misc_feature
<222> LOCATION: (8)..(8)
<223> OTHER INFORMATION: D-amino acid
<220> FEATURE:
<221> NAME/KEY: misc_feature
<222> LOCATION: (9)..(9)
<223> OTHER INFORMATION: Having palmitoyl-PEG-miniPEG3- bound thereto
<220> FEATURE:
<221> NAME/KEY: misc_feature
<222> LOCATION: (9)..(9)
<223> OTHER INFORMATION: Xaa is beta-homophenylalanine

<400> SEQUENCE: 83

Xaa Thr His Xaa Xaa Arg Cys Arg Xaa
1               5

<210> SEQ ID NO 84
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (6)..(6)
<223> OTHER INFORMATION: Xaa is N-MeArg
<220> FEATURE:
<221> NAME/KEY: misc_feature
<222> LOCATION: (8)..(8)
<223> OTHER INFORMATION: Xaa is N-MeArg
<220> FEATURE:
```

```
<221> NAME/KEY: misc_feature
<222> LOCATION: (9)..(9)
<223> OTHER INFORMATION: Having palmitoyl-PEG-miniPEG3- bound thereto
<220> FEATURE:
<221> NAME/KEY: misc_feature
<222> LOCATION: (9)..(9)
<223> OTHER INFORMATION: Xaa is beta-homophenylalanine

<400> SEQUENCE: 84

Xaa Thr His Xaa Xaa Xaa Cys Xaa Xaa
1               5

<210> SEQ ID NO 85
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (6)..(6)
<223> OTHER INFORMATION: Xaa is bhArg
<220> FEATURE:
<221> NAME/KEY: misc_feature
<222> LOCATION: (8)..(8)
<223> OTHER INFORMATION: Xaa is bhArg
<220> FEATURE:
<221> NAME/KEY: misc_feature
<222> LOCATION: (9)..(9)
<223> OTHER INFORMATION: Having palmitoyl-PEG-miniPEG3- bound thereto
<220> FEATURE:
<221> NAME/KEY: misc_feature
<222> LOCATION: (9)..(9)
<223> OTHER INFORMATION: Xaa is beta-homophenylalanine

<400> SEQUENCE: 85

Xaa Thr His Xaa Xaa Xaa Cys Xaa Xaa
1               5

<210> SEQ ID NO 86
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (9)..(9)
<223> OTHER INFORMATION: Having palmitoyl-PEG- bound thereto
<220> FEATURE:
<221> NAME/KEY: misc_feature
```

<222> LOCATION: (9)..(9)
<223> OTHER INFORMATION: Xaa is beta-homophenylalanine

<400> SEQUENCE: 86

Xaa Thr His Xaa Xaa Arg Cys Arg Xaa
1               5

<210> SEQ ID NO 87
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (9)..(9)
<223> OTHER INFORMATION: Xaa is beta-homophenylalanine

<400> SEQUENCE: 87

Xaa Thr His Xaa Xaa Arg Cys Arg Xaa
1               5

<210> SEQ ID NO 88
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (7)..(7)
<223> OTHER INFORMATION: Xaa is Cys(S-S-Pal)
<220> FEATURE:
<221> NAME/KEY: misc_feature
<222> LOCATION: (9)..(9)
<223> OTHER INFORMATION: Xaa is beta-homophenylalanine

<400> SEQUENCE: 88

Xaa Thr His Xaa Xaa Arg Xaa Arg Xaa
1               5

<210> SEQ ID NO 89
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature

```
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (7)..(7)
<223> OTHER INFORMATION: Xaa is Cys(S-S-cysteamine-Pal)
<220> FEATURE:
<221> NAME/KEY: misc_feature
<222> LOCATION: (9)..(9)
<223> OTHER INFORMATION: Xaa is beta-homophenylalanine

<400> SEQUENCE: 89

Xaa Thr His Xaa Xaa Arg Xaa Arg Xaa
1               5

<210> SEQ ID NO 90
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (7)..(7)
<223> OTHER INFORMATION: Xaa is Cys(S-S-Cys-NHPal)
<220> FEATURE:
<221> NAME/KEY: misc_feature
<222> LOCATION: (9)..(9)
<223> OTHER INFORMATION: Xaa is beta-homophenylalanine

<400> SEQUENCE: 90

Xaa Thr His Xaa Xaa Arg Xaa Arg Xaa
1               5

<210> SEQ ID NO 91
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (7)..(7)
```

```
<223> OTHER INFORMATION: Xaa is Cys(S-S-Cys)
<220> FEATURE:
<221> NAME/KEY: misc_feature
<222> LOCATION: (9)..(9)
<223> OTHER INFORMATION: Having palmitoyl-PEG-miniPEG3- bound thereto
<220> FEATURE:
<221> NAME/KEY: misc_feature
<222> LOCATION: (9)..(9)
<223> OTHER INFORMATION: Xaa is beta-homophenylalanine

<400> SEQUENCE: 91

Xaa Thr His Xaa Xaa Arg Xaa Arg Xaa
1               5

<210> SEQ ID NO 92
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida(NHPal)
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (9)..(9)
<223> OTHER INFORMATION: Xaa is beta-homophenylalanine

<400> SEQUENCE: 92

Xaa Thr His Xaa Xaa Arg Cys Arg Xaa
1               5

<210> SEQ ID NO 93
<211> LENGTH: 10
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (9)..(9)
<223> OTHER INFORMATION: Xaa is beta-homophenylalanine
<220> FEATURE:
<221> NAME/KEY: misc_feature
<222> LOCATION: (10)..(10)
<223> OTHER INFORMATION: Xaa is Ida(NHPal)

<400> SEQUENCE: 93

Xaa Thr His Xaa Xaa Arg Cys Arg Xaa Xaa
1               5                   10

<210> SEQ ID NO 94
```

```
<211> LENGTH: 10
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (9)..(9)
<223> OTHER INFORMATION: Xaa is beta-homophenylalanine
<220> FEATURE:
<221> NAME/KEY: misc_feature
<222> LOCATION: (10)..(10)
<223> OTHER INFORMATION: Xaa is Ahx-Ida(NHPal)

<400> SEQUENCE: 94

Xaa Thr His Xaa Xaa Arg Cys Arg Xaa Xaa
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (9)..(9)
<223> OTHER INFORMATION: Xaa is beta-homophenylalanine
<220> FEATURE:
<221> NAME/KEY: misc_feature
<222> LOCATION: (10)..(10)
<223> OTHER INFORMATION: Xaa is Ahx-Ida(NBzl2)

<400> SEQUENCE: 95

Xaa Thr His Xaa Xaa Arg Cys Arg Xaa Xaa
1               5                   10

<210> SEQ ID NO 96
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
```

```
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (9)..(9)
<223> OTHER INFORMATION: Having C16 bound thereto
<220> FEATURE:
<221> NAME/KEY: misc_feature
<222> LOCATION: (9)..(9)
<223> OTHER INFORMATION: Xaa is beta-homophenylalanine

<400> SEQUENCE: 96

Xaa Thr His Xaa Xaa Arg Cys Arg Xaa
1               5

<210> SEQ ID NO 97
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino acids
<220> FEATURE:
<221> NAME/KEY: misc_feature
<222> LOCATION: (7)..(7)
<223> OTHER INFORMATION: Xaa is Cys(S-S-tBut)
<220> FEATURE:
<221> NAME/KEY: misc_feature
<222> LOCATION: (9)..(9)
<223> OTHER INFORMATION: Having butanoyl-PEG11- bound thereto

<400> SEQUENCE: 97

Asp Thr His Phe Pro Arg Xaa Arg Trp
1               5

<210> SEQ ID NO 98
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino acids
<220> FEATURE:
<221> NAME/KEY: misc_feature
<222> LOCATION: (7)..(7)
<223> OTHER INFORMATION: Xaa is Cys(S-S-tBut)
<220> FEATURE:
<221> NAME/KEY: misc_feature
<222> LOCATION: (9)..(9)
<223> OTHER INFORMATION: Having octanoyl-PEG11- bound thereto

<400> SEQUENCE: 98

Asp Thr His Phe Pro Arg Xaa Arg Trp
1               5

<210> SEQ ID NO 99
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino acids
```

```
<220> FEATURE:
<221> NAME/KEY: misc_feature
<222> LOCATION: (7)..(7)
<223> OTHER INFORMATION: Xaa is Cys(S-S-tBut)
<220> FEATURE:
<221> NAME/KEY: misc_feature
<222> LOCATION: (9)..(9)
<223> OTHER INFORMATION: Having palmitoyl-PEG11- bound thereto

<400> SEQUENCE: 99

Asp Thr His Phe Pro Arg Xaa Arg Trp
1               5

<210> SEQ ID NO 100
<211> LENGTH: 9
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(9)
<223> OTHER INFORMATION: D-amino acids
<220> FEATURE:
<221> NAME/KEY: misc_feature
<222> LOCATION: (7)..(7)
<223> OTHER INFORMATION: Xaa is Cys(S-S-tBut)
<220> FEATURE:
<221> NAME/KEY: misc_feature
<222> LOCATION: (9)..(9)
<223> OTHER INFORMATION: Having tetracosanoyl-PEG11- bound thereto

<400> SEQUENCE: 100

Asp Thr His Phe Pro Arg Xaa Arg Trp
1               5

<210> SEQ ID NO 101
<211> LENGTH: 10
<212> TYPE: PRT
<213> ORGANISM: Artificial Sequence
<220> FEATURE:
<223> OTHER INFORMATION: Based on Homo sapiens sequence
<220> FEATURE:
<221> NAME/KEY: misc_feature
<222> LOCATION: (1)..(1)
<223> OTHER INFORMATION: Xaa is Ida
<220> FEATURE:
<221> NAME/KEY: misc_feature
<222> LOCATION: (4)..(4)
<223> OTHER INFORMATION: Xaa is 3,3-diphenyl-L-alanine
<220> FEATURE:
<221> NAME/KEY: misc_feature
<222> LOCATION: (5)..(5)
<223> OTHER INFORMATION: Xaa is L-beta-homoproline
<220> FEATURE:
<221> NAME/KEY: misc_feature
<222> LOCATION: (10)..(10)
<223> OTHER INFORMATION: Xaa is Ahx-Ida(NHPal)

<400> SEQUENCE: 101

Xaa Thr His Xaa Xaa Arg Cys Arg Trp Xaa
1               5                   10
```

MODIFIED MINI-HEPCIDIN PEPTIDES AND METHODS OF USING THEREOF

CROSS-REFERENCE TO RELATED APPLICATIONS

This application is a continuation of U.S. patent application Ser. No. 14/363,012, filed 5 Jun. 2014, which is a 371 National Phase Entry of PCT/US2012/068180, filed 6 Dec. 2012, and claims the benefit of U.S. Patent Application Ser. No. 61/568,724, filed 9 Dec. 2011, which are herein incorporated by reference in their entirety.

This application is related to U.S. patent application Ser. No. 13/131,792, which is a 371 National Phase entry of PCT/US2009/066711, filed 4 Dec. 2009, and U.S. Provisional Application Ser. No. 61/120,277, filed 5 Dec. 2008, all of which are herein incorporated by reference in their entirety.

ACKNOWLEDGEMENT OF GOVERNMENT SUPPORT

This invention was made with Government support under DK090554, awarded by the National Institutes of Health. The Government has certain rights in the invention.

REFERENCE TO A SEQUENCE LISTING SUBMITTED VIA EFS-WEB

The content of the ASCII text file of the sequence listing named "20151228_034044_097US1_subseq_ST25" which is 42.8 kb in size was created on Dec. 28, 2015, and electronically submitted via EFS-Web on Apr. 6, 2016, is incorporated herein by reference in its entirety.

BACKGROUND OF THE INVENTION

1. Field of the Invention

The present invention generally relates to peptides which exhibit hepcidin activity.

2. Description of the Related Art

Hepcidin, a peptide hormone produced by the liver, is a regulator of iron homeostasis in humans and other mammals. Hepcidin acts by binding to its receptor, the iron export channel ferroportin, and causing its internalization and degradation. Human hepcidin is a 25-amino acid peptide (Hep25). See Krause et al. (2000) FEBS Lett 480:147-150, and Park et al. (2001) J Biol Chem 276:7806-7810. The structure of the bioactive 25-amino acid form of hepcidin is a simple hairpin with 8 cysteines that form 4 disulfide bonds as described by Jordan et al. (2009) J Biol Chem 284:24155-67. The N terminal region is required for iron-regulatory function, and deletion of 5 N-terminal amino acid residues results in a loss of iron-regulatory function. See Nemeth et al. (2006) Blood 107:328-33.

Abnormal hepcidin activity is associated with iron overload diseases which include hereditary hemochromatosis and iron-loading anemias and myelodysplasia. Hereditary hemochromatosis (HH) is a genetic iron overload disease that is mainly caused by hepcidin deficiency, or very rarely by hepcidin resistance. This allows excessive absorption of iron from the diet and development of iron overload. Clinical manifestations of HH may include liver disease (hepatic cirrhosis, hepatocellular carcinoma), diabetes, and heart failure. Currently, the only treatment for HH is regular phlebotomy, which is effective but very burdensome for the patients.

Iron-loading anemias are hereditary anemias with ineffective erythropoiesis such as β-thalassemia, which are accompanied by severe iron overload. Complications from iron overload are the main cause of morbidity and mortality for these patients. Hepcidin deficiency is the main cause of iron overload in untransfused patients, and contributes to iron overload in transfused patients. The current treatment for iron overload in these patients is iron chelation which is very burdensome, sometimes ineffective and accompanied by frequent side effects.

SUMMARY OF THE INVENTION

The present invention generally relates to peptides which exhibit hepcidin activity and methods of using thereof.

The present invention provides peptides, which may be isolated and/or purified, comprising, consisting essentially or consisting of the following Structural Formula IA or IB:

A1-A2-A3-A4-A5-A6-A7-A8-A9-A10    IA

A10-A9-A8-A7-A6-A5-A4-A3-A2-A1    IB wherein

A1 is Asp, D-Asp, Glu, D-Glu, pyroglutamate, D-pyroglutamate, Gln, D-Gln, Asn, D-Asn, or an unnatural amino acid commonly used as a substitute thereof such as bhAsp, Ida, Ida(NHPal), and N-MeAsp, preferably Ida and N-MeAsp;

A2 is Thr, D-Thr, Ser, D-Ser, Val, D-Val, Ile, D-Ile, Ala, D-Ala or an unnatural amino acid commonly used as a substitute thereof such as Tle, Inp, Chg, bhThr, and N-MeThr;

A3 is His, D-His, Asn, D-Asn, Arg, D-Arg, or an unnatural amino acid commonly used as a substitute thereof such as L-His(π-Me), D-His(π-Me), L-His(τ-Me), or D-His(τ-Me);

A4 is Phe, D-Phe, Leu, D-Leu, Ile, D-Ile, Trp, D-Trp, Tyr, D-Tyr, or an unnatural amino acid commonly used as a substitute thereof such as Phg, bhPhe, Dpa, Bip, 1Nal, 2Nal, bhDpa, Amc, PheF5, hPhe, Igl, or cyclohexylalanine, preferably Dpa;

A5 is Pro, D-Pro, Ser, D-Ser, or an unnatural amino acid commonly used as a substitute thereof such as Oic, bhPro, trans-4-PhPro, cis-4-PhPro, cis-5-PhPro, and Idc, preferably bhPro;

A6 is Arg, D-Arg, Ile, D-Ile, Leu, D-Leu, Thr, D-Thr, Lys, D-Lys, Val, D-Val, or an unnatural amino acid commonly used as a substitute thereof such as D-Nω,ω-dimethyl-arginine, L-Nω,ω-dimethyl-arginine, D-homoarginine, L-homoarginine, D-norarginine, L-norarginine, citrulline, a modified Arg wherein the guanidinium group is modified or substituted, Norleucine, norvaline, bhIle, Ach, N-MeArg, and N-MeIle, preferably Arg;

A7 is Cys, D-Cys, Ser, D-Ser, Ala, D-Ala, or an unnatural amino acid such as Cys(S-tBut), homoCys, Pen, (D)Pen, preferably S-tertiary butyl-cysteine, Cys(S-S-Pal), Cys(S-S-cysteamine-Pal), Cys(S-S-Cys-NHPal), and Cys(S-S-Cys);

A8 is Arg, D-Arg, Ile, D-Ile, Leu, D-Leu, Thr, D-Thr, Lys, D-Lys, Val, D-Val, or an unnatural amino acid commonly used as a substitute thereof such as D-Nω,ω-dimethyl-arginine, L-Nω,ω-dimethyl-arginine, D-homoarginine, L-homoarginine, D-norarginine, L-norarginine, citrulline, a modified Arg wherein the guanidinium group is modified or substituted, Norleucine, norvaline, bhIle, Ach, N-MeArg, and N-MeIle, preferably Arg;

A9 is Phe, D-Phe, Leu, D-Leu, Ile, D-Ile, Tyr, D-Tyr, Trp, D-Trp, Phe-$R^a$, D-Phe-$R^a$, Dpa-$R^a$, D-Dpa-$R^a$, Trp-$R^a$, bhPhe-R$^a$, or an unnatural amino acid commonly used as a substitute thereof such as PheF5, N-MePhe, benzylamide, 2-aminoindane, bhPhe, Dpa, Bip, 1Nal, 2Nal, bhDpa, and cyclohexylalanine, which may or may not have R$^a$ linked thereto, preferably bhPhe and bhPhe-R$^a$, wherein R$^a$ is palmitoyl-PEG-, wherein PEG is PEG11 or miniPEG3, palmitoyl-PEG-PEG, wherein PEG is PEG11 or miniPEG3, butanoyl (C4)-PEG11-, octanoyl (C8, Caprylic)-PEG11-, palmitoyl (C16)-PEG11-, or tetracosanoyl (C24, Lignoceric)-PEG11-; and A10 is Cys, D-Cys, Ser, D-Ser, Ala, D-Ala, or an unnatural amino acid such as Ida, Ida(NHPal)Ahx, and Ida(NBzl2)Ahx;

wherein the carboxy-terminal amino acid is in amide or carboxy-form; wherein at least one sulfhydryl amino acid is present as one of the amino acids in the sequence; and wherein A1, A1 to A2, A10, or a combination thereof are optionally absent, with the proviso that the peptide is not one of the peptides as set forth in Table 1. In some embodiments, the peptides of the present invention contain at least one of the following: a) A1=N-MeAsp, Ida, or Ida(NHPal); b) A5=bhPro; c) A6=D-Val, D-Leu, Lys, D-Lys, Arg, D-Arg, Ach, bhArg, or N-MeArg; d) A7=Cys(S-S-Pal), Cys(S-S-cysteamine-Pal), Cys(S-S-Cys-NHPal), or Cys(S-S-Cys); and/or e) A8=D-Val, D-Leu, Lys, D-Lys, Arg, D-Arg, Ach, bhArg, or N-MeArg. In some embodiments, i) when A1 is Ida and A9 is Phe, then A10 is not Ahx-Ida(NHPal); ii) when A1 is Ida, A9 is not bhPhe-R$^b$, wherein R$^b$ is S-(palmityl) thioglycolic-PEG-; iii) when A4 is D-Phe, A7 is not D-Cys (S-S-tBut) and A9 is not D-Trp-R$^c$, wherein R$^c$ is Butanoyl-PEG11-, Octanoyl-PEG11-, Palmitoyl-PEG11-, or Tetracosanoyl-PEG11-; or iv) when A1 is Ida and A9 is bhPhe-R$^d$, wherein R$^d$ is palmitoyl-PEG-miniPEG3-, A6 and A8 are not both D-Arg or both bhArg. In some embodiments, A1 is D-Asp, N-MeAsp, Ida, or Ida(NHPal); A2 is Thr or D-Thr; A3 is His or D-His; A4 is Dpa or D-Dpa; A5 is Pro, D-Pro, bhPro, or Oic; A6 is Ile, D-Ile, Arg, D-Val, D-Leu, Ach, or N-MeArg; A7 is Cys, D-Cys, Cys(S-S-Pal), Cys(S-S-cysteamine-Pal), Cys(S-S-Cys-NHPal), or Cys(S-S-Cys); A8 is Ile, D-Ile, Arg, D-Val, D-Leu, Ach, or N-MeArg; A9 is Phe, D-Phe, Dpa, D-Dpa, Trp, D-Trp, bhPhe, Phe-R$^a$, D-Phe-R$^a$, Dpa-R$^a$, D-Dpa-R$^a$, Trp-R$^a$, bhPhe-R$^a$, wherein R$^a$ is palmitoyl-PEG-, wherein PEG is PEG11 or miniPEG3, palmitoyl-PEG-PEG, wherein PEG is PEG11 or miniPEG3, butanoyl (C4)-PEG11-, octanoyl (C8, Caprylic)-PEG11-, palmitoyl (C16)-PEG11-, or tetracosanoyl (C24, Lignoceric)-PEG11-; and A10, if present, is Ida(NHPal)Ahx or Ida(NBzl2)Ahx. In some embodiments, A6 and/or A8 is a lysine derivative such as N-ε-Dinitrophenyl-lysine, N-ε-Methyl-lysine, N,N-ε-Dimethyl-lysine, and N,N,N-ε-Trimethyl-lysine. In some embodiments, the peptide is selected from the group consisting of: PR42', PR47, PR48, PR49, PR50, PR51, PR52, PR53, PR56, PR57, PR58, PR59, PR60, PR61, PR63, PR65, PR66, PR67, PR68, PR69, PR70, PR71, PR72, PR73, PR74, and PR82.

In some embodiments, the peptides form a cyclic structure by a disulfide bond. In some embodiments, the peptides exhibit hepcidin activity. In some embodiments, the peptides bind ferroportin, preferably human ferroportin.

In some embodiments, the present invention provides compositions and medicaments which comprise at least one peptide, which may be isolated, synthesized and/or purified, comprising, consisting essentially or consisting of Structural Formula IA or IB as set forth herein. In some embodiments, the present invention provides method of manufacturing medicaments for the treatment of diseases of iron metabolism, such as iron overload diseases, which comprise at least one peptide, which may be isolated and/or purified, comprising, consisting essentially or consisting of Structural Formula IA or IB as set forth herein. Also provided are methods of treating a disease of iron metabolism in a subject, such as a mammalian subject, preferably a human subject, which comprises administering at least one peptide, which may be isolated and/or purified, comprising, consisting essentially or consisting of Structural Formula IA or IB as set forth herein or a composition comprising said at least one peptide to the subject. In some embodiments, the peptide is administered in a therapeutically effective amount. In some embodiments, the therapeutically effective amount is an effective daily dose administered as a single daily dose or as divided daily doses. The peptides of the present invention can also be administered at a variety of doses.

In some embodiments the dose is given as a weekly dose, e.g. from 1-10,000 μg/kg/dose. In some embodiments, the daily dose is about 1-1,000, preferably about 10-500 μm/kg/day. Dosages can vary according to the type of formulation of peptidyl drug administered as well as the route of administration. One skilled in the art can adjust the dosage by changing the route of administration or formulation, so that the dosage administered would result in a similar pharmacokinetic or biological profile as would result from the preferred dosage ranges described herein. In some embodiments, the composition to be administered is formulated for oral, pulmonary or mucosal administration.

Some embodiments include any dosage with any route of administration which results in an effective pharmacokinetic and pharmacodynamic profile by reducing serum iron values by 10-80%. Some preferred doses include those that result in a desired reduction in serum iron. Administration of the peptidyl or protein formulations of the present invention includes both direct administration, including self-administration, and indirect administration, including the act of prescribing a drug. For example, a physician who instructs a patient to self-administer a drug and/or provides a patient with a prescription for a drug is considered to be administering the drug to the patient.

In some embodiments, the present invention provides methods of binding a ferroportin or inducing ferroportin internalization and degradation which comprises contacting the ferroportin with at least one peptide or composition as disclosed herein.

In some embodiments, the present invention provides kits comprising at least one peptide or composition as disclosed herein packaged together with a reagent, a device, instructional material, or a combination thereof.

In some embodiments, the present invention provides complexes which comprise at least one peptide as disclosed herein bound to a ferroportin, preferably a human ferroportin, or an antibody, such as an antibody which specifically binds a peptide as disclosed herein, Hep25, or a combination thereof.

In some embodiments, the present invention provides the use of at least one peptide, which may be isolated and/or purified, comprising, consisting essentially or consisting of Structural Formula IA or IB as set forth herein or a composition comprising, consisting essentially of, or consisting of said at least one peptide for the manufacture of a medicament for treating a disease of iron metabolism and/or lowering the amount of iron in a subject in need thereof, wherein the medicament is prepared to be administered at an effective daily dose, as a single daily dose, or as divided daily doses. In some embodiments, the dose is about 1-1,000, preferably about 10-500 μm/kg/day. In some embodiments, the medicament is formulated for subcutaneous injection or oral, pulmonary or mucosal administration.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 10A shows the structural formula of PR65 (SEQ ID NO:86). Ida=iminodiacetic acid, Dpa=diphenylalanine, bhPro=beta-homo proline, bhPhe=beta-homo phenylalanine. FIG. 10B shows the serum iron in wild-type C57BL/6 mice 4 hours after intraperitoneal injection of solvent, native hepcidin or PR65 (n=4-8 in each group). **p=0.01, *p=0.005. FIG. 10C shows the serum iron in wild-type C57BL/6 mice 4 hours after intraperitoneal or subcutaneous injection of 20 nmoles of PR65 (n=4 in each group). *p=0.007, p=0.04. In FIGS. 10B and 10C** the bars represent mean values and error bars standard deviations.

FIG. 11A shows that PR65 induced a dose-dependent decrease in serum iron 24 hours after a subcutaneous injection. Mean values and standard deviations are shown, n=3-5 mice per point. #p=0.005, &p=0.004, *p<0.001. FIG. 11B shows the time course of hypoferremia induced by a subcutaneous injection of 100 nmoles of PR65. Mean and standard deviations are shown, n=4-6 mice per point. #p=0.008, *p<0.001.

FIGS. 13A-13E show that PR65 prevented iron loading in iron-depleted hepcidin knockout mice. All mice were placed on an iron-deficient diet (4 ppm iron) from ages 5-6 weeks until 12 weeks. The "baseline" group (n=7) was examined at 12 weeks of age (white bars). The rest of the mice were fed an iron-loading diet (300 ppm) for 2 more weeks while receiving daily subcutaneous injections of solvent (grey bars, n=6) or PR65 at 20, 50 or 100 nmoles per day (black bars, n=4 per dose). The mice were analyzed 24 hours after the last injection. Compared to solvent, PR65 injections resulted in: FIG. 13A—iron retention in the spleen; FIG. 13B—a dose-dependent decrease in serum iron; FIG. 13C—a corresponding dose-dependent decrease in Hb levels; FIG. 13D—a decrease in heart iron at higher doses; and FIG. 13E—decreased liver iron. Liver iron content in PR65-injected mice did not significantly differ from that in the baseline group of mice, indicating that little to no new iron was absorbed or deposited in the liver during the 2-week treatment. Graphs show means and standard deviations. Student's t-test was used to compare the mean of each condition to that of solvent treatment (p value over bars). In FIG. 13E, mean of each condition was also compared to the baseline (p values at lines over bars).

FIG. 15A—spleen iron increased more than 15-fold confirming PR65 activity; FIG. 15B—serum iron concentrations were similar 24 hours after the last injection; FIG. 15C—hemoglobin decreased by 2 g/dL indicating iron restriction to erythropoiesis; FIG. 15D—heart iron tended to decrease, though the difference was not statistically significant at the number of mice tested; FIG. 15E—liver iron decreased by about 20%.

DETAILED DESCRIPTION OF THE INVENTION

Figure 1:
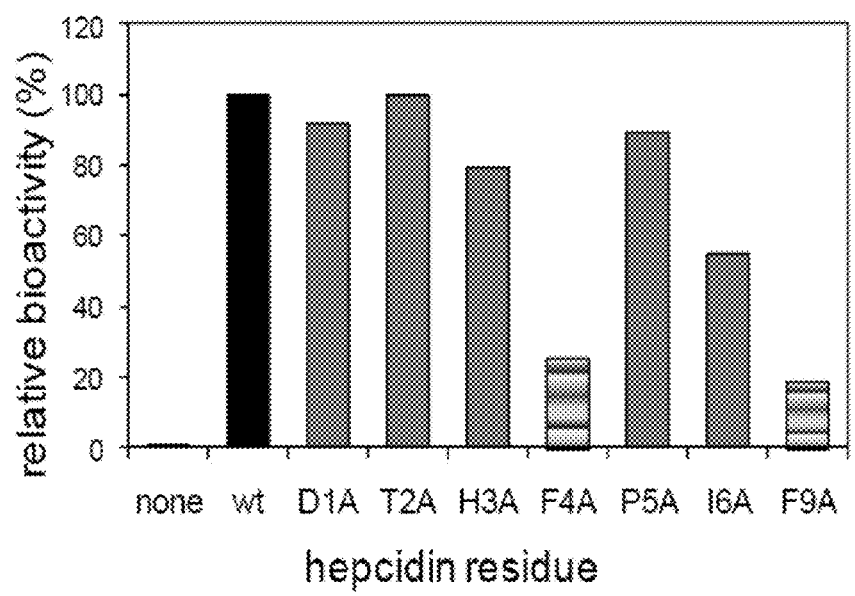
FIG. 1 is a graph showing the relative hepcidin activity of alanine substitutions in Hep25.

The present invention provides peptides which are useful in the study and treatment of diseases of iron metabolism.

As used herein, a "disease of iron metabolism" includes diseases where aberrant iron metabolism directly causes the disease, or where iron blood levels are dysregulated causing disease, or where iron dysregulation is a consequence of another disease, or where diseases can be treated by modulating iron levels, and the like. More specifically, a disease of iron metabolism according to this disclosure includes iron overload diseases, iron deficiency disorders, disorders of iron biodistribution, other disorders of iron metabolism and other disorders potentially related to iron metabolism, etc. Diseases of iron metabolism include hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia intermedia, alpha thalassemia, sideroblastic anemia, porphyria, porphyria cutanea tarda, African iron overload, hyperferritinemia, ceruloplasmin deficiency, atransferrinemia, congenital dyserythropoietic anemia, anemia of chronic disease, anemia of inflammation, anemia of infection, hypochromic microcytic anemia, iron-deficiency anemia, iron-refractory iron deficiency anemia, anemia of chronic kidney disease, erythropoietin resistance, iron deficiency of obesity, other anemias, benign or malignant tumors that overproduce hepcidin or induce its overproduction, conditions with hepcidin excess, Friedreich ataxia, gracile syndrome, Hallervorden-Spatz disease, Wilson's disease, pulmonary hemosiderosis, hepatocellular carcinoma, cancer, hepatitis, cirrhosis of liver, pica, chronic renal failure, insulin resistance, diabetes, atherosclerosis, neurodegenerative disorders, multiple sclerosis, Parkinson's disease, Huntington's disease, and Alzheimer's disease. As used herein, "iron overload diseases" and "diseases of iron overload" refer diseases and disorders that result in or may cause abnormally high levels of iron in afflicted subjects if untreated.

In some cases the diseases and disorders included in the definition of "disease of iron metabolism" are not typically identified as being iron related. For example, hepcidin is highly expressed in the murine pancreas suggesting that diabetes (Type I or Type II), insulin resistance, glucose intolerance and other disorders may be ameliorated by treating underlying iron metabolism disorders. See Ilyin, G. et al. (2003) FEBS Lett. 542 22-26, which is herein incorporated by reference. As such, these diseases are encompassed under the broad definition. Those skilled in the art are readily able to determine whether a given disease is a "disease or iron metabolism" according to the present invention using methods known in the art, including the assays of WO 2004092405, which is herein incorporated by reference, and assays which monitor hepcidin, hemojuvelin, or iron levels and expression, which are known in the art such as those described in U.S. Pat. No. 7,534,764, which is herein incorporated by reference.

In preferred embodiments of the present invention, the diseases of iron metabolism are iron overload diseases, which include hereditary hemochromatosis, iron-loading anemias, alcoholic liver diseases and chronic hepatitis C.

As used herein, the terms "protein", "polypeptide" and "peptide" are used interchangeably to refer to two or more amino acids linked together. Except for the abbreviations for the uncommon or unnatural amino acids set forth in Table 2 below, the three-letter and one-letter abbreviations, as used in the art, are used herein to represent amino acid residues. Except when preceded with "D-", the amino acid is an L-amino acid. Groups or strings of amino acid abbreviations are used to represent peptides. Except when specifically indicated, peptides are indicated with the N-terminus on the left and the sequence is written from the N-terminus to the C-terminus.

The peptides of the present invention may be made using methods known in the art including chemical synthesis (solid-phase, solution phase, or a combination of both), biosynthesis or in vitro synthesis using recombinant DNA methods. See e.g. Kelly & Winkler (1990) Genetic Engineering Principles and Methods, vol. 12, J. K. Setlow ed., Plenum Press, NY, pp. 1-19; Merrifield (1964) J Amer Chem Soc 85:2149; Houghten (1985) PNAS USA 82:5131-5135; and Stewart & Young (1984) Solid Phase Peptide Synthesis, 2ed. Pierce, Rockford, Ill., which are herein incorporated by reference. The peptides of the present invention may be purified using protein purification techniques known in the art such as reverse phase high-performance liquid chromatography (HPLC), ion-exchange or immunoaffinity chromatography, precipitation, filtration, size exclusion, or electrophoresis. See Olsnes, S. and A. Pihl (1973) Biochem. 12(16):3121-3126; and Scopes (1982) Protein Purification, Springer-Verlag, NY, which are herein incorporated by reference. Alternatively, the peptides of the present invention may be made by recombinant DNA techniques known in the art. Thus, polynucleotides that encode the polypeptides of the present invention are contemplated herein. In preferred embodiments, the polynucleotides are isolated. As used herein "isolated polynucleotides" refers to polynucleotides that are in an environment different from that in which the polynucleotide naturally occurs.

In some embodiments, the peptides of the present invention are substantially purified. As used herein, a "substantially purified" compound refers to a compound that is removed from its natural environment and is at least about 60% free, preferably about 75% free, and most preferably about 90% free from other macromolecular components with which the compound is naturally associated, or a compound that is at least about 60% free, preferably about 75% free, and most preferably about 90% free from other peptide components as measured by HPLC with detection at 214 nm.

As used herein, an "isolated" compound refers to a compound which is isolated from its native environment. For example, an isolated peptide is one which does not have its native amino acids, which correspond to the full length polypeptide, flanking the N-terminus, C-terminus, or both. For example, isolated Hep1-9 refers to an isolated peptide comprising amino acid residues 1-9 of Hep25 which may have non-native amino acids at its N-terminus, C-terminus, or both, but does not have a cysteine amino acid residue following its $9^{th}$ amino acid residue at the C-terminus. As set forth herein, references to amino acid positions correspond to the amino acid residues of Hep25. For example, reference to amino acid position 9, corresponds to the $9^{th}$ amino acid residue of Hep25.

The peptides of the present invention bind ferroportin, preferably human ferroportin. Preferred peptides of the present invention specifically bind human ferroportin. As used herein, "specifically binds" refers to a specific binding agent's preferential interaction with a given ligand over other agents in a sample. For example, a specific binding agent that specifically binds a given ligand, binds the given ligand, under suitable conditions, in an amount or a degree that is observable over that of any nonspecific interaction with other components in the sample. Suitable conditions are those that allow interaction between a given specific binding agent and a given ligand. These conditions include pH, temperature, concentration, solvent, time of incubation, and the like, and may differ among given specific binding agent and ligand pairs, but may be readily determined by those skilled in the art.

The peptides of the present invention that mimic the hepcidin activity of Hep25, the bioactive human 25-amino acid form, are herein referred to as "mini-hepcidins". As used herein, a compound having "hepcidin activity" means that the compound has the ability to lower plasma iron concentrations in subjects (e.g. mice or humans), when administered thereto (e.g. parenterally injected or orally administered), in a dose-dependent and time-dependent manner. See e.g. as demonstrated in Rivera et al. (2005), Blood 106:2196-9.

In some embodiments, the peptides of the present invention have in vitro activity as assayed by the ability to cause the internalization and degradation of ferroportin in a ferroportin-expressing cell line as taught in Nemeth et al. (2006) Blood 107:328-33. In vitro activity may be measured by the dose-dependent loss of fluorescence of cells engineered to display ferroportin fused to green fluorescent protein as in Nemeth et al. (2006) Blood 107:328-33. Aliquots of cells are incubated for 24 hours with graded concentrations of a reference preparation of Hep25 or a mini-hepcidin. As provided herein, the $EC_{50}$ values are provided as the concentration of a given compound (e.g. peptide) that elicits 50% of the maximal loss of fluorescence generated by the reference Hep25 preparation. $EC_{50}$ of Hep25 preparations in this assay range from 5 to 15 nM and preferred mini-hepcidins have $EC_{50}$ values in in vitro activity assays of about 1,000 nM or less.

Other methods known in the art for calculating the hepcidin activity and in vitro activity of peptides according to the present invention may be used. For example, the in vitro activity of compounds may be measured by their ability to internalize cellular ferroportin, which is determined by immunohistochemistry or flow cytometry using antibodies which recognizes extracellular epitopes of ferroportin. Alternatively, the in vitro activity of compounds may be measured by their dose-dependent ability to inhibit the efflux of iron from ferroportin-expressing cells that are preloaded with radioisotopes or stable isotopes of iron, as in Nemeth et al. (2006) Blood 107:328-33.

Design of Mini-Hepcidins

Previous studies indicate that the N-terminal segment of Hep25 is important for its hepcidin activity and is likely to form the contact interface with ferroportin. However, the importance of each N-terminal amino acid to hepcidin activity was unknown. Therefore, alanine-scanning mutagenesis was performed on residues 1-6 of Hep25 to determine the contribution of each N-terminal amino acid to hepcidin activity. As shown in FIG. 1, the T2A substitution did not substantially impact hepcidin activity. Phenylalanine substitutions (F4A or F9A) caused the largest decrease, more than about 70%, in hepcidin activity. The remaining alanine substitutions had detectable decreases in hepcidin activity which were not as significant as the F4A or F9A substitutions.

Figure 2A:
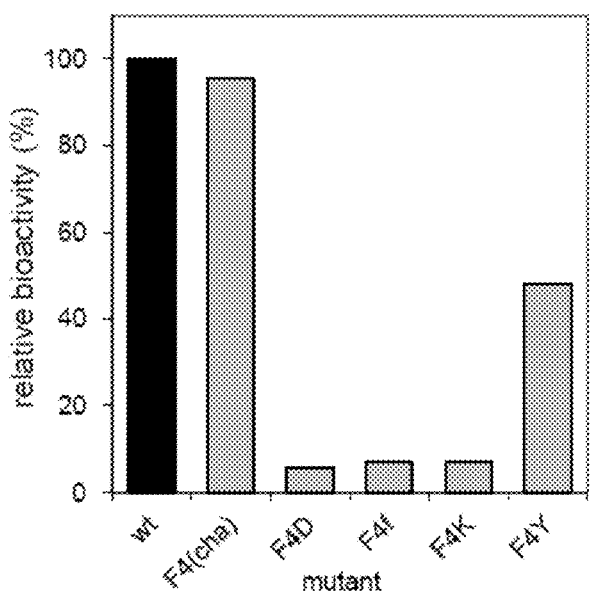
FIG. 2A is a graph showing the relative hepcidin activities of F4 substitutions in Hep25.

To determine whether the highly conserved and apparently structurally important F4 phenylalanine is important for hepcidin activity, the F4 amino acid of Hep25 was systematically substituted with other amino acids. As shown in FIG. 2A, making the side-chain more polar (F4Y) led to substantial loss of hepcidin activity as did the substitution with D-phenylalanine (f) or charged amino acids (D, K and Y). However, hepcidin activity was maintained when the F4 residue was substituted with nonaromatic cyclohexylalanine, thereby indicating that a bulky hydrophobic residue is sufficient for activity.

Figure 2B:
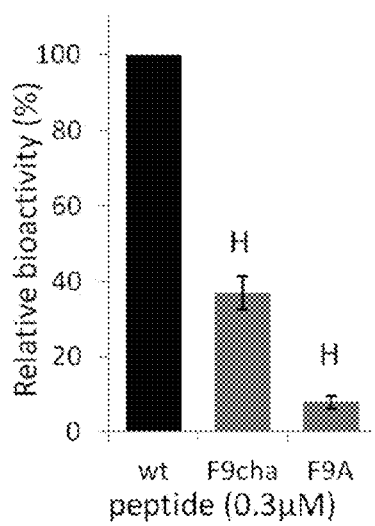
FIG. 2B is a graph showing the relative hepcidin activities of F9 substitutions in Hep25.

To determine whether the highly conserved and apparently structurally important F9 phenylalanine is important for hepcidin activity, the F9 amino acid of Hep25 was substituted with other amino acids. As shown in FIG. 2B, hepcidin activity not only decreased when F9 was substituted with alanine, but also when it was substituted with nonaromatic cyclohexylalanine, thereby indicating that an aromatic residue may be important for activity.

Mutational studies indicate that C326, the cysteine residue at position 326 of human ferroportin, is the critical residue involved in binding hepcidin. Thus, various N-terminal fragments of Hep25 containing a thiol, i.e. Hep 4-7, Hep3-7, Hep3-8, Hep3-9, Hep1-7, Hep1-8, Hep1-9, and Hep1-10 C7A, were chemically synthesized, refolded and their activities relative to Hep25 were assayed using flow-cytometric quantitation of the ferroportin-GFP degradation, iron efflux estimation based on measurements of cellular ferritin, and radioisotopic iron efflux studies. The sequences and $EC_{50}$'s of these N-terminal fragments are shown in Table 1.

Figure 3A:
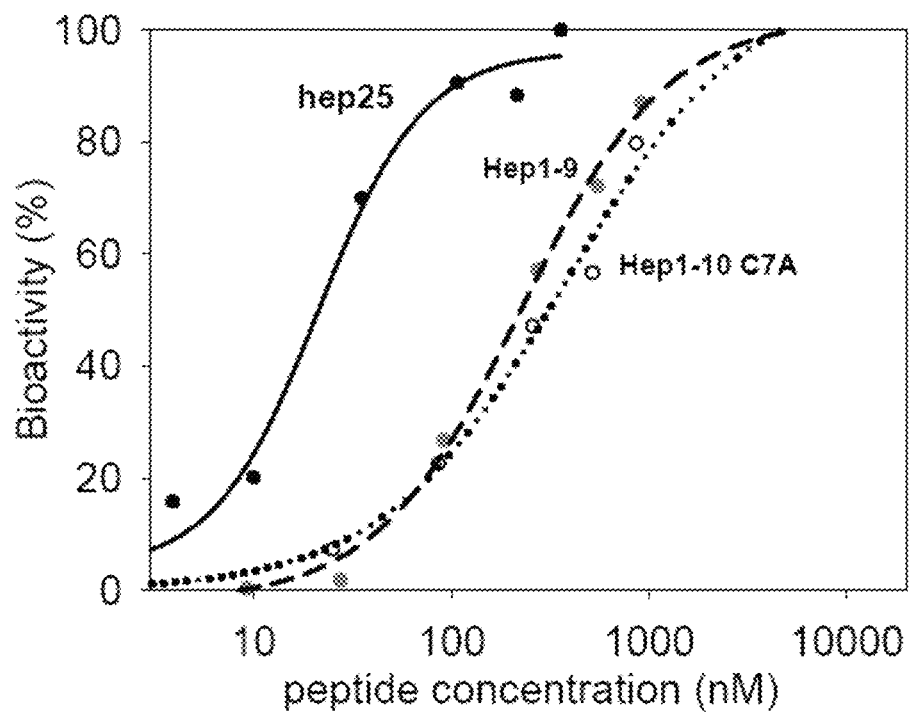
FIG. 3A is a graph showing the hepcidin activities of Hep1-9 and Hep1-10 C7A relative to Hep25 (A).
Figure 3B:
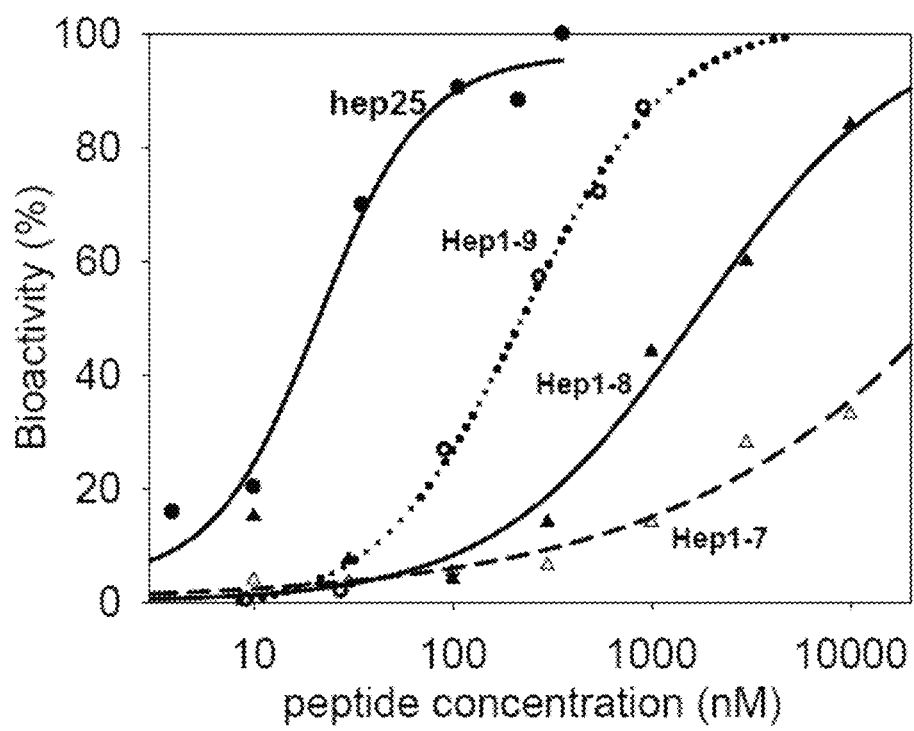
FIG. 3B is a graph showing the hepcidin activities of Hep1-7 and Hep1-8 relative to Hep1-9 or Hep25.
Figure 3C:
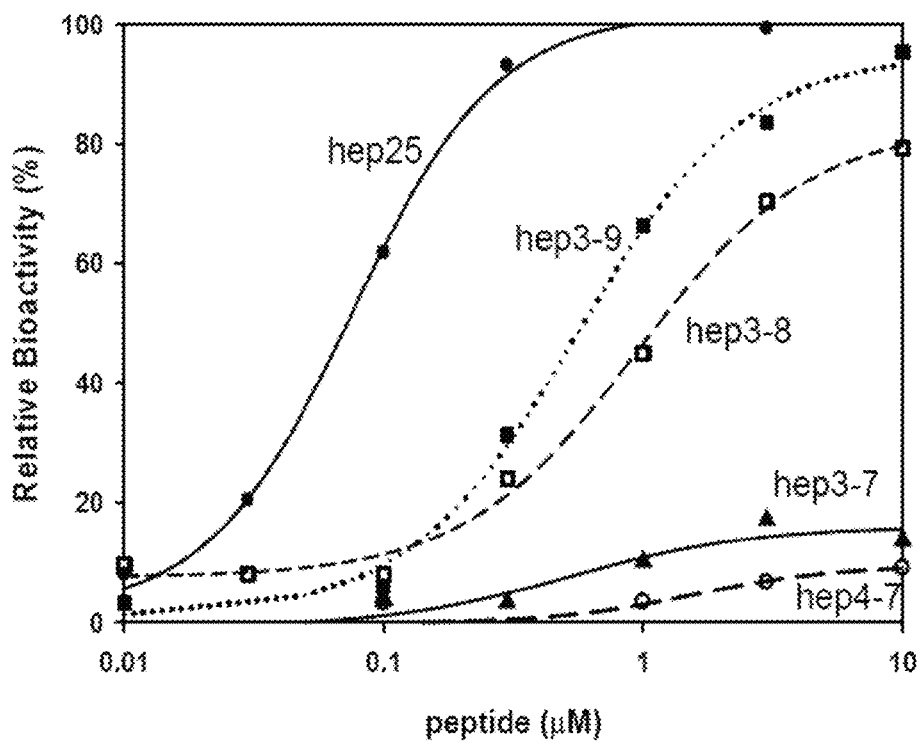
FIG. 3C is a graph showing the hepcidin activities of Hep4-7, Hep3-7, Hep3-8 and Hep3-9 relative to Hep25.

Remarkably and unexpectedly, as shown in FIG. 3, Hep1-9 and Hep1-10 C7A were found to be quite active in the flow-cytometry assay of ferroportin-GFP internalization. On a mass basis, Hep1-9 and Hep1-10 C7A were only about 4-times less potent and on a molar basis, about 10-times less potent than Hep25. Thus, Hep1-9 and Hep1-10 C7A were used as the basis to construct other peptides having hepcidin activity.

Figure 4:
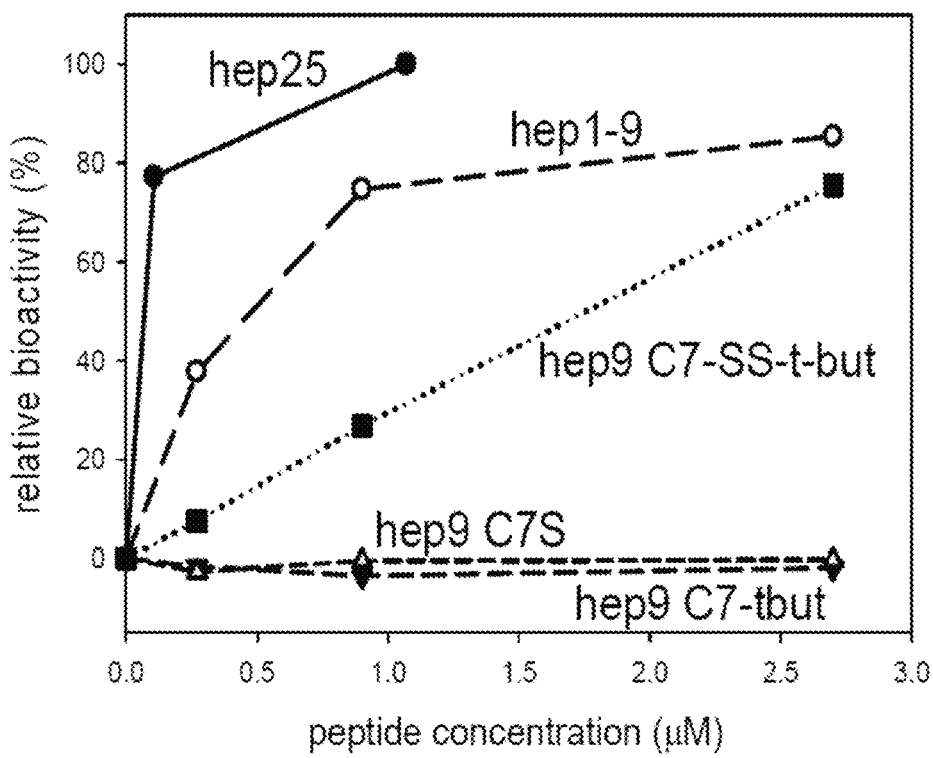
FIG. 4 is a graph showing the hepcidin activities of C7 modified peptides relative to Hep25 and Hep 1-9.

To determine the importance of the cysteine thiol on the hepcidin activity of Hep1-9, the C7 residue of Hep1-9 was substituted with amino acids that have a similar shape but cannot form disulfide bonds to give Hep9-C7S (serine substitution) and Hep9C7-tBut (t-butyl-blocked cysteine) or with a cysteine modified by disulfide coupled tertiary butyl, which can participate in disulfide exchange with HS-t-butyl as the leaving group, to give Hep9C7-SStBut. As shown in FIG. 4, amino acid substitutions that ablated the potential for disulfide formation or exchange caused a complete loss of hepcidin activity, thereby indicating that disulfide formation is required for activity. Other C7 amino acid substitutions and their resulting hepcidin activities are shown in Table 1.

Other peptides based on Hep1-9 and Hep1-10 C7A were constructed to be disulfide cyclized, have unnatural amino acid substitutions, be retroinverted, have modified F4 and F9 residues, or have a positive charge. The C-terminal amino acid was the amidated form. The modifications and the resulting hepcidin activities are shown in Table 1.

As shown in Table 1, with the exception of PR40 and PR41, mini-hepcidins which exhibit $EC_{50}$'s of about 1000 nM or less contain at least 6 contiguous amino acid residues which correspond to residues 3-8 of Hep25 (see Hep3-8). Thus, in some embodiments, preferred mini-hepcidins have at least 6 contiguous amino acid residues that correspond to 6 contiguous amino acid residues of Hep1-9, preferably residues 3-8. The amino acid residues may be unnatural or uncommon amino acids, L- or D-amino acid residues, modified residues, or a combination thereof.

In some embodiments, the mini-hepcidins of the present invention have at least one amino acid substitution, a modification, or an addition. Examples of amino acid substitutions include substituting an L-amino acid residue for its corresponding D-amino acid residue, substituting a Cys for homoCys, Pen, (D)Pen, Inp, or the like, substituting Phe for bhPhe, Dpa, bhDpa, Bip, 1Nal, and the like. The names and the structures of the substituting residues are exemplified in Table 2. Other suitable substitutions are exemplified in Table 1. Examples of a modification include modifying one or more amino acid residues such that the peptide forms a cyclic structure, retroinversion, and modifying a residue to be capable of forming a disulfide bond. Examples of an addition include adding at least one amino acid residue or at least one compound to either the N-terminus, the C-terminus, or both such as that exemplified in Table 1.

As shown in Table 1, a majority of the mini-hepcidins which exhibit $EC_{50}$'s of about 100 nM or less contain at least one Dpa or bhDpa amino acid substitution. Thus, in some embodiments, the mini-hepcidins of the present invention have at least one Dpa or bhDpa amino acid substitution.

In view of the alanine substitution data of FIG. 1, in some embodiments, the mini-hepcidins of the present invention may have an Ala at amino acid positions other than amino acid position 4 and 9 as long as there is an available thiol for forming a disulfide bond at amino acid position 7. See Hep9F4A and Hep9C-SStBut in Table 1.

In view of the position 4 amino acid substitution data of FIG. 2 and Table 1, the mini-hepcidins of the present invention may have an amino acid substitution at position 4 which does not result in a substantial change of its charge or polarity as compared to that of Hep25, Hep1-9 or Hep1-10 C7A. Preferred amino acid substitutions at position 4 of Hep1-9 or Hep1-10 C7A include Phe, D-Phe, bhPhe, Dpa, bhDpa, Bip, 1Nal, or the like.

The original mini-hepcidins as referenced herein have the following Structural Formula I $$A1-A2-A3-A4-A5-A6-A7-A8-A9-A10 \qquad \text{I}$$

wherein
A1 is Asp, Glu, pyroglutamate, Gln, Asn, or an unnatural amino acid commonly used as a substitute thereof;
A2 is Thr, Ser, Val, Ala, or an unnatural amino acid commonly used as a substitute thereof;
A3 is His, Asn, Arg, or an unnatural amino acid commonly used as a substitute thereof;
A4 is Phe, Leu, Ile, Trp, Tyr, or an unnatural amino acid commonly used as a substitute thereof which includes cyclohexylalanine;
A5 is Pro, Ser, or an unnatural amino acid commonly used as a substitute thereof;
A6 is Ile, Leu, Val, or an unnatural amino acid commonly used as a substitute thereof;
A7 is Cys, Ser, Ala, or an unnatural amino acid commonly used as a substitute thereof which includes S-tertiary butyl-cysteine;
A8 is Ile, Leu, Thr, Val, Arg, or an unnatural amino acid commonly used as a substitute thereof;
A9 is Phe, Leu, Ile, Tyr, or an unnatural amino acid commonly used as a substitute thereof which includes cyclohexylalanine; and
A10 is Cys, Ser, Ala, or an unnatural amino acid commonly used as a substitute thereof;
wherein the carboxy-terminal amino acid is in amide or carboxy-form;
wherein a Cys or another sulfhydryl amino acid is present as one of the amino acids in the sequence; and
wherein A1, A2, A3, A1 to A2, A1 to A3, A10, A9 to A10, A8 to A10, or a combination thereof are optionally absent.

In some embodiments, A1 is Asp; A2 is Thr; A3 is His; A4 is Phe; A5 is Pro; A6 is Ile; A7 is Ala; A8 is Ile; A9 is Phe; and A10 is Cys in amide form; wherein A1 or A1 to A2 are optionally absent.

In some embodiments, A1 is Asp, A2 is Thr, A3 is His, A4 is Phe, A5 is Pro, A6 is Ile, A7 is Cys or an unnatural thiol amino acid, A8 is Ile, A9 is Phe in amide form, and A10 is absent.

In some embodiments, A1 and A2 are absent, A3 is His, A4 is Phe, A5 is Pro, A6 is Ile, A7 is Cys or an unnatural thiol amino acid, A8 is Ile in amide form, and A9 and A10 are absent.

In some embodiments, A1 and A2 are absent, A3 is His, A4 is Phe, A5 is Pro, A6 is Ile, A7 is Cys or an unnatural thiol amino acid in amide form, and A8 to A10 are absent.

In some embodiments, the unnatural amino acid of A1, A2, A3, A4, A5, A6, A7, A8, A9, A10, or a combination thereof is the corresponding D-amino acid. For example, for A1, the unnatural amino acid may be D-Asp, D-Glu, D-Gln, D-Asn, or the like.

In some embodiments, the unnatural amino acid for:
A1 is D-Asp, D-Glu, D-pyroglutamate, D-Gln, D-Asn, bhAsp, Ida, or N-MeAsp;
A2 is D-Thr, D-Ser, D-Val, Tle, Inp, Chg, bhThr, or N-MeThr;
A3 is D-His, D-Asn, D-Arg, Dpa, (D)Dpa, or 2-aminoindan;
A4 is D-Phe, D-Leu, D-Ile, D-Trp, Phg, bhPhe, Dpa, Bip, 1Nal, bhDpa, Amc, PheF5, hPhe, Igl, or cyclohexylalanine;
A5 is D-Pro, D-Ser, Oic, bhPro, trans-4-PhPro, cis-4-PhPro, cis-5-PhPro, Idc;
A6 is D-Ile, D-Leu, Phg, Chg, Amc, bhIle, Ach, and N-MeIle;
A7 is D-Cys, D-Ser, D-Ala, Cys(S-tBut), homoCys, Pen, (D)Pen, Dap(AcBr), and Inp;
A8 is D-Ile, D-Leu, D-Thr, D-Val, D-Arg, Chg, Dpa, bhIle, Ach, or N-MeIle;

A9 is D-Phe, D-Leu, D-Ile, PheF5, N-MePhe, benzylamide, bhPhe, Dpa, Bip, 1Nal, bhDpa, cyclohexylalanine; and A10 is D-Cys, D-Ser, D-Ala.

In some embodiments, the amino acid substitution (and addition, if indicated) for:

A1 is Ala, D-Ala, Cys, D-Cys, Phe, D-Phe, Asp or D-Asp linked to Cys or D-Cys, Phe or D-Phe linked to a PEG molecule linked to chenodeoxycholate, ursodeoxycholate, or palmitoyl, or Dpa or (D)Dpa linked to palmitoyl;

A2 is Ala, D-Ala, Cys, D-Cys, Pro, D-Pro, Gly, or D-Gly;

A3 is Ala, D-Ala, Cys, D-Cys, Dpa, Asp or D-Asp linked to Dpa or (D)Dpa;

A4 is Ala, D-Ala, Pro, or D-Pro;

A5 is Ala, D-Ala, Pro, D-Pro, Arg, D-Arg;

A6 is Ala, D-Ala, Phe, D-Phe, Arg, D-Arg, Cys, D-Cys;

A7 is His, or D-His;

A8 is Cys, or D-Cys; and

A9 is Phe or D-Phe linked to RA, Asp, D-Asp, Asp or D-Asp linked to RB, bhPhe linked to RC, or cysteamide, wherein RA is —CONH$_2$—CH$_2$—CH$_2$—S, -D-Pro linked to Pro-Lys or Pro-Arg, -bhPro linked to Pro linked to Pro-Lys or Pro-Arg, -D-Pro linked to bhPro-Lys or bhPro-Arg, wherein RB is -PEG11-GYI-PEAPRDGQAYVRKDGEWVLLSTFL, -(PEG11)-(GPHyp)10, and wherein RC is -D-Pro linked to Pro-Lys or Pro-Arg, -D-Pro linked to bhPro-Lys or bhPro-Arg.

In some embodiments, the mini-hepcidin is a 10-mer sequence wherein A7 is Ala and A10 is Cys.

In some embodiments, the mini-hepcidin forms a cyclic structure by a disulfide bond.

In some embodiments, the mini-hepcidin is a retroinverted peptide such that A1 is the C-terminus and A10 is the N-terminus and the amino acid residues are D-amino acids. In some embodiments, the retroinverted peptide has at least one addition at the N-terminus, C-terminus, or both. In some embodiments, the retroinverted peptide contains at least one L-amino acid.

In some embodiments, the mini-hepcidin has an amino acid substitution at position 4, position 9, or both. In some embodiments, the amino acid substituent is Phg, Phe, D-Phe, bhPhe, Dpa, Bip, 1Nal, Dpa, bhDpa, Amc, or cysteamide.

In some embodiments, the mini-hepcidin has an amino acid substitution at position 7. In some embodiments, the amino acid substituent is Cys(S-tBut), Ala, D-Ala, Ser, D-Ser, homoCys, Pen, (D)Pen, His, D-His, or Inp.

Examples of some original mini-hepcidins are provided in Table 1.

TABLE 1

| Name | 1 | 2 | 3 | 4 | 5 | 6 | 7 | 8 | 9 | 10 | EC$_{50}$ (nM) |
|---|---|---|---|---|---|---|---|---|---|---|---|
| Hep25 DTHFPICIFCCG CCHRSKCGMCCKT (SEQ ID NO: 1) | | | | | | | | | | | 10 |
| Hep10wt (SEQ ID NO: 2) | D | T | H | F | P | I | C | I | F | C | |
| Length | | | | | | | | | | | |
| Hep4 (Hep4-7) (SEQ ID NO: 3) | - | - | - | F | P | I | C | - | - | - | >10,000 |
| Hep5 (Hep3-7) (SEQ ID NO: 4) | - | - | H | F | P | I | C | - | - | - | >10,000 |
| Hep6 (Hep3-8) (SEQ ID NO: 5) | - | - | H | F | P | I | C | I | - | - | 1000 |
| Hep7ΔDT (Hep3-9) (SEQ ID NO: 6) | - | - | H | F | P | I | C | I | F | - | 700 |
| Hep7 (Hep1-7) (SEQ ID NO: 7) | D | T | H | F | P | I | C | - | - | - | >10,000 |
| Hep8 (Hep1-8) (SEQ ID NO: 8) | D | T | H | F | P | I | C | I | - | - | 2000 |
| Hep9 (Hep1-9) (SEQ ID NO: 9) | D | T | H | F | P | I | C | I | F | - | 76 |
| Hep10 (Hep1-10 C7A) (SEQ ID NO: 10) | D | T | H | F | P | I | A | I | F | C | 100 |
| Thiol Modified | | | | | | | | | | | |
| Hep9F4A (SEQ ID NO: 11) | D | T | H | A | P | I | C | I | F | - | >3000 |
| Hep9C7-SStBut (SEQ ID NO: 12) | D | T | H | A | P | I | C-S-tBut | I | F | - | 700 |

TABLE 1-continued

|  | 1 | 2 | 3 | 4 | 5 | 6 | 7 | 8 | 9 | 10 | EC$_{50}$ (nM) |
|---|---|---|---|---|---|---|---|---|---|---|---|
| Hep9C7-tBut (SEQ ID NO: 13) | D | T | H | A | P | I | C-tBut | I | F | - | >10,000 |
| Hep9-C7A (SEQ ID NO: 14) | D | T | H | F | P | I | A | I | F | - | >10,000 |
| Hep9-C7S (SEQ ID NO: 15) | D | T | H | F | P | I | S | I | F | - | >10,000 |
| (D)C (SEQ ID NO: 16) | D | T | H | F | P | I | C | I | F | - | 1000 |
| homoC (SEQ ID NO: 17) | D | T | H | F | P | I | homoCys | I | F | - | 900 |
| Pen (SEQ ID NO: 18) | D | T | H | F | P | I | Pen | I | F | - | 700 |
| (D)Pen (SEQ ID NO: 19) | D | T | H | F | P | I | (D)Pen | I | F | - | 3000 |
| Dap(AcBr) (SEQ ID NO: 20) | D | T | H | F | P | I | Dap(AcBr) | I | F | - | >10000 |
| Disulfide Cyclized | | | | | | | | | | | |
| Cyc-1 (SEQ ID NO: 21) | C-D | T | H | F | P | I | C | I | F | - | 300 |
| Cyc-4 (SEQ ID NO: 22) | D | T | H | F | P | I | C | I | F-R1 | - | >10000 |
| Cyc-2 (SEQ ID NO: 23) | - | C | H | F | P | I | C | I | F | - | >10000 |
| Cyc-3 (SEQ ID NO: 24) | - | - | H | F | P | I | C | I | F-R1 | - | >10000 |
| Unnatural AA's | | | | | | | | | | | |
| PR10 (SEQ ID NO: 25) | D | Tle | H | Phg | Oic | Chg | C | Chg | F | - | >3000 |
| PR11 (SEQ ID NO: 26) | D | Tle | H | P | Oic | Chg | C | Chg | F | - | >3000 |
| Retroinverted | | | | | | | | | | | |
| PR12 (SEQ ID NO: 27) | F | I | C | I | P | F | H | T | D | - | 900* |
| riHep7ΔDT (SEQ ID NO: 28) | F | I | C | I | P | F | H | - | - | - | 150* |
| Modified Retroinverted | | | | | | | | | | | |
| PR23 (SEQ ID NO: 29) | R2-F | I | C | I | P | F | H | T | D | - | 100 |
| PR24 (SEQ ID NO: 30) | R3-F | I | C | I | P | F | H | T | D | - | 1000* |
| PR25 (SEQ ID NO: 31) | F | I | C | I | P | F | H | T | D-R6 | - | 600 |
| PR26 (SEQ ID NO: 32) | F | I | C | I | P | F | H | T | D-R6 | - | >10,000 |
| PR27 (SEQ ID NO: 33) | R4-F | I | C | I | P | F | H | T | D | - | 20* |
| PR28 (SEQ ID NO: 34) | R5-F | I | C | I | P | F | H | T | D | - | 3000 |

TABLE 1-continued

| | 1 | 2 | 3 | 4 | 5 | 6 | 7 | 8 | 9 | 10 | EC$_{50}$ (nM) |
|---|---|---|---|---|---|---|---|---|---|---|---|
| Modified F4 and F9 | | | | | | | | | | | |
| F4bhPhe (SEQ ID NO: 35) | D | T | H | bhPhe | P | I | C | I | F | - | 700 |
| F4Dpa (SEQ ID NO: 36) | D | T | H | Dpa | P | I | C | I | F | - | 30 |
| F4Bip (SEQ ID NO: 37) | D | T | H | Bip | P | I | C | I | F | - | 150 |
| F4 1Nal (SEQ ID NO: 38) | D | T | H | 1Nal | P | I | C | I | F | - | 110 |
| F4bhDpa (SEQ ID NO: 39) | D | T | H | bhDpa | P | I | C | I | F | - | 80 |
| F9bhPhe (SEQ ID NO: 40) | D | T | H | F | P | I | C | I | bhPhe | - | 150 |
| F9Dpa (SEQ ID NO: 41) | D | T | H | F | P | I | C | I | Dpa | - | 70 |
| F9Bip (SEQ ID NO: 42) | D | T | H | F | P | I | C | I | Bip | - | 150 |
| F91Nal (SEQ ID NO: 43) | D | T | H | F | P | I | C | I | 1Nal | - | 200 |
| F9bhDpa (SEQ ID NO: 44) | D | T | H | F | P | I | C | I | bhDpa | - | 100 |
| PR39 (SEQ ID NO: 45) | D | T | H | Dpa | P | I | C | I | Dpa | - | 35 |
| PR40 (SEQ ID NO: 46) | D | - | Dpa | - | P | I | C | I | F | - | 70 |
| PR41 (SEQ ID NO: 47) | D | - | Dpa | - | P | I | C | I | Dpa | - | 300 |
| PR43 (SEQ ID NO: 48) | D | T | H | Dpa | P | <u>R</u> | C | <u>R</u> | Dpa | - | 200 |
| PR44 (SEQ ID NO: 49) | D | T | H | Dpa | Oic | I | C | I | F | - | 30 |
| PR45 (SEQ ID NO: 50) | D | T | H | Dpa | Oic | I | C | I | Dpa | - | 150 |
| PR46 (SEQ ID NO: 51) | D | T | H | Dpa | P | C | C | C | Dpa | - | 80 |
| Positive Charge | | | | | | | | | | | |
| PR13 (SEQ ID NO: 52) | D | T | H | F | P | I | C | I | F-R8 | - | 100 |
| PR14 (SEQ ID NO: 53) | D | T | H | F | P | I | C | I | F-R9 | - | 90 |
| PR15 (SEQ ID NO: 54) | D | T | H | F | P | I | C | I | F-R10 | - | 150 |
| PR16 (SEQ ID NO: 55) | D | T | H | F | P | I | C | I | F-R11 | - | 50 |
| PR17 (SEQ ID NO: 56) | D | T | H | F | P | I | C | I | F-R12 | - | 300 |
| PR18 (SEQ ID NO: 57) | D | T | H | F | P | I | C | I | F-R13 | - | 1000 |
| PR19 (SEQ ID NO: 58) | D | T | H | F | P | I | C | I | bhPhe-R8 | - | 700 |

TABLE 1-continued

| | 1 | 2 | 3 | 4 | 5 | 6 | 7 | 8 | 9 | 10 | EC$_{50}$ (nM) |
|---|---|---|---|---|---|---|---|---|---|---|---|
| PR20 (SEQ ID NO: 59) | D | T | H | F | P | I | C | I | bhPhe-R9 | - | 200 |
| PR21 (SEQ ID NO: 60) | D | T | H | F | P | I | C | I | bhPhe-R12 | - | 500 |
| PR22 (SEQ ID NO: 61) | D | T | H | F | P | I | C | I | bhPhe-R13 | - | 600 |
| PR-1 (SEQ ID NO: 62) | C | Inp | (D)Dpa | Amc | R | Amc | Inp | Dpa | Cysteamide** | - | 1500 |
| PR-2 (SEQ ID NO: 63) | C | P | (D)Dpa | Amc | R | Amc | Inp | Dpa | Cysteamide** | - | 2000 |
| PR-3 (SEQ ID NO: 64) | C | P | (D)Dpa | Amc | R | Amc | Inp | Dpa | Cysteamide** | - | 1000 |
| PR-4 (SEQ ID NO: 65) | C | G | (D)Dpa | Amc | R | Amc | Inp | Dpa | Cysteamide** | - | 2000 |

R1 = -CONH$_2$-CH$_2$-CH$_2$-S
R2 = Chenodeoxycholate-(D)Asp-(PEG11)-
R3 = Ursodeoxycholate-(D)Asp-(PEG11)-
R4 = Palmitoyl-(PEG11)-
R5 = (Palmitoyl)$_2$-Dap-PEG11-, wherein "Dap" = diaminopropionic acid
R6 = -(PEG11)-GYIPEAPRDGQAYVRKDGEWVLLSTFL
R7 = -(PEG11)-(GPHyp)10, "GPHyp" = Gly-Pro-hydroxyproline
R8 = -PPK
R9 = -PPR
R10 = -bhProPK
R11 = -bhProPR
R12 = -PbhProK
R13 = -PbhProR
Underlined residues = D amino acids
"-" indicates a covalent bond, e.g. point of attachment to the given peptide
Double underlined = residues connected by a disulfide link to form a cyclized structure
*active in vivo
**oxidized
The PEG compound may be PEG11, i.e. O-(2-aminoethyl)-O'(2-carboxyethyl)-undecaethyleneglycol
PR12, riHep7ΔDT, PR23, PR24, PR25, PR26, PR27 and PR28 are retroinverted mini-hepcidins and are shown, left to right, from their C-terminus to their N-terminus.

| TABLE 2 | TABLE 2-continued |
|---|---|
| Uncommon or Unnatural Amino Acids | Uncommon or Unnatural Amino Acids |
| Chg  L-α-cyclohexylglycine | 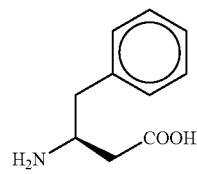 β-homophenylalanine Dpa |
| Tle 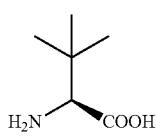 L-tert-leucine bhPhe | 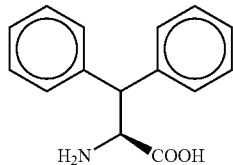 3,3-diphenyl-L-alanine bhPro |

TABLE 2-continued

Uncommon or Unnatural Amino Acids

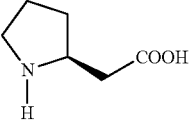

L-β-homoproline
Phg

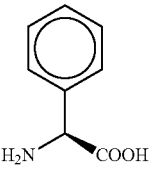

L-phenylglycine
1Nal

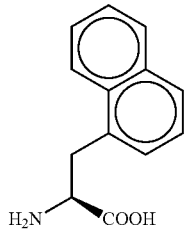

(1-naphthyl)-L-alanine
bhDpa

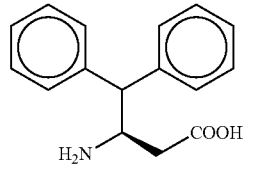

(S)-3-Amino-4,4-diphenylbutanoic acid
Bip

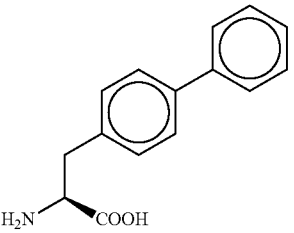

L-biphenylalanine
Pen

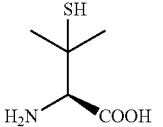

L-Penicillamine
(D)Pen

TABLE 2-continued

Uncommon or Unnatural Amino Acids

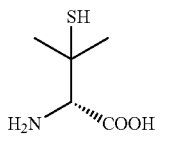

D-Penicillamine
Cys(tBut)

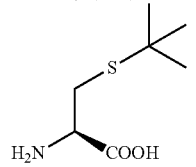

S-t-butyl-L-cysteine
Oic

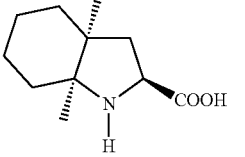

octahydroindole-2-carboxylic acid
Dap(AcBr)

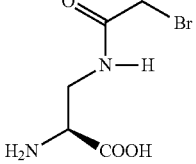

N$^\gamma$-(bromoacetyl)-L-2,3-diaminopropionic acid
homoCys

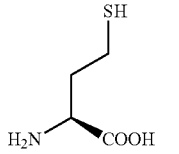

L-homocysteine
Cys(S-tBut)

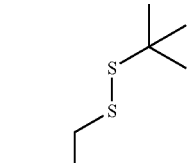

S-t-Butylthio-L-cysteine
Amc

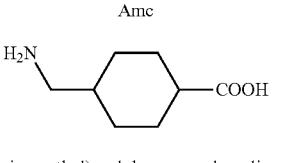

4-(aminomethyl)cyclohexane carboxylic acid
Inp

TABLE 2-continued
Uncommon or Unnatural Amino Acids
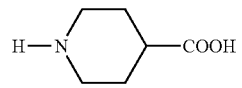
isonipecotic acid
bhAsp
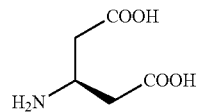
Ida
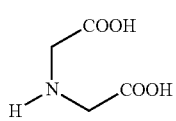
N-MeAsp
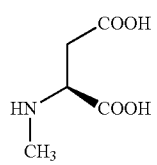
N-MeThr
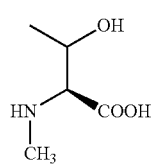
2-Aminoindane
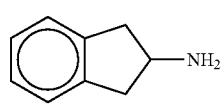
PheF5
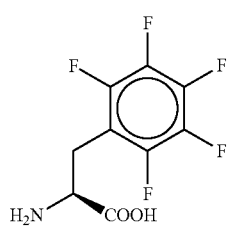
hPhe
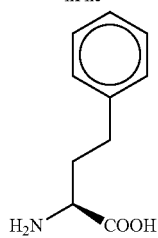
Igl
TABLE 2-continued
Uncommon or Unnatural Amino Acids
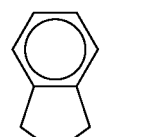
trans-4-PhPro
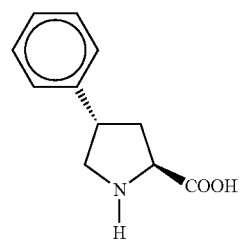
cis-4-PhPro
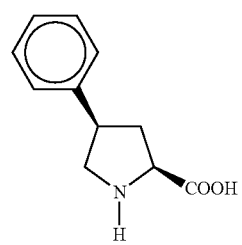
cis-5-PhPro
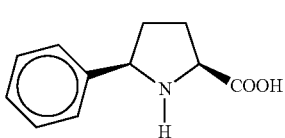
Idc
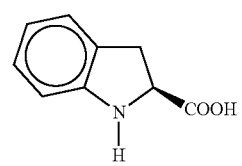
bhIle
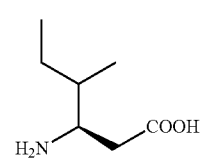
Ach TABLE 2-continued Uncommon or Unnatural Amino Acids

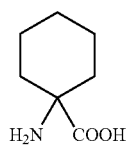
N-MeIle

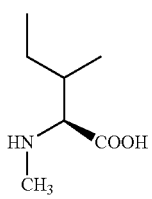
N-MePhe

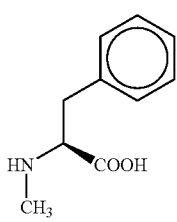
Benzylamide

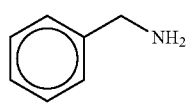
(D)Dpa

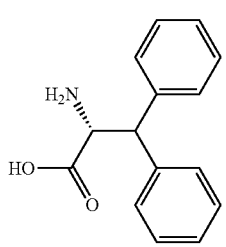 [SMILES: N[C@@H](C(=O)O)C(c1ccccc1)c1ccccc1]
3,3-diphenyl-D-alanine
Ahx

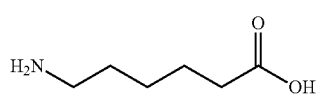
N-MeArg

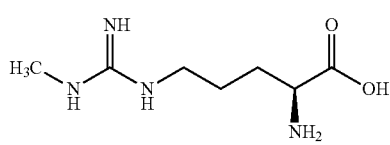
2Nal

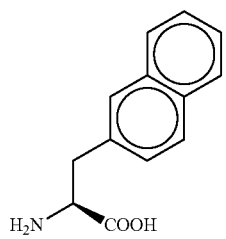
L-His(π-Me)

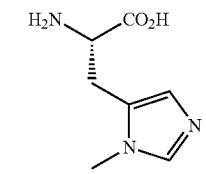
L-His(τ-Me)

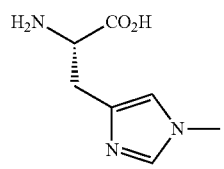

Peptide Synthesis

Hep25 was synthesized at the UCLA Peptide Synthesis Core Facility using solid phase 9-fluorenylmethyloxycarbonyl (fmoc) chemistry. Specifically, the peptides were synthesized on an ABI 431A peptide synthesizer (PE Biosystems, Applied Biosystems, Foster City, Calif.) using fmoc amino acids, Wang resin (AnaSpec, San Jose, Calif.), and double coupling for all residues. After cleavage, 30 mg crude peptides was reduced with 1000-fold molar excess of dithiothreitol (DTT) in 0.5 M Tris buffer (pH 8.2), 6 M guanidine hydrochloride, and 20 mM EDTA at 52° C. for 2 hours. Fresh DTT (500-molar excess) was added and incubated for an additional hour at 52° C. The reduced peptides were purified on the 10-g C18 Sep-Pak cartridges (Waters, Milford, Mass.) equilibrated in 0.1% TFA and eluted with 50% acetonitrile. The eluates were lyophilized and resuspended in 0.1% acetic acid. The reduced peptides were further purified by reversed-phase high-performance liquid chromatography (RP-HPLC) on Vydac C18 column (218TP510; Waters) equilibrated with 0.1% trifluoroacetic acid and eluted with an acetonitrile gradient. The eluates were lyophilized, dissolved in 0.1% acetic acid, 20% DMSO, to the approximate concentration of 0.1 mg/ml (pH 8), and air oxidized by stirring for 18 hours at room temperature. The refolded peptides were also purified sequentially on the 10-g C18 Sep-pak cartridge and on the RP-HPLC VYDAC C18 column using an acetonitrile gradient. The eluates were lyophilized and resuspended in 0.016% HCl. The conformation of refolded synthetic hepcidin derivatives was verified by electrophoresis in 12.5% acid-urea polyacrylamide gel electrophoresis (PAGE), and peptide masses were determined by matrix-assisted laser desorption/ionization time-of-flight mass spectrometry (MALDI-TOF-MS; UCLA Mass Spectrometry Facility, Los Angeles, Calif.).

The other peptides set forth in Table 1 were synthesized by the solid phase method using either Symphony® automated peptide synthesizer (Protein Technologies Inc., Tucson, Ariz.) or CEM Liberty automatic microwave peptide synthesizer (CEM Corporation Inc., Matthews, N.C.), applying 9-fluorenylmethyloxycarbonyl (Fmoc) chemistry (Fields & Noble (1990) Int J Pept Protein Res 35:161-214) and commercially available amino acid derivatives and reagents (EMD Biosciences, San Diego, Calif. and Chem-Impex International, Inc., Wood Dale, Ill.). Peptides were cleaved from resin using modified reagent K (TFA 94% (v/v); phenol, 2% (w/v); water, 2% (v/v); TIS, 2% (v/v); 2 hours) and precipitated by addition of ice-cold diethyl ether. Subsequently, peptides were purified by preparative reverse-phase high performance liquid chromatography (RP-HPLC) to >95% homogeneity and their purity evaluated by matrix-assisted laser desorption ionization spectrometry (MALDI-MS, UCLA Mass Spectrometry Facility, Los Angeles, Calif.) as well as analytical RP-HPLC employing Varian ProStar 210 HPLC system equipped with ProStar 325 Dual Wavelength UV-Vis detector with the wavelengths set at 220 nm and 280 nm (Varian Inc., Palo Alto, Calif.). Mobile phases consisted of solvent A, 0.1% TFA in water, and solvent B, 0.1% TFA in acetonitrile. Analyses of peptides were performed with a reversed-phase C18 column (Vydac 218TP54, 4.6×250 mm, Grace, Deerfield, Ill.) applying linear gradient of solvent B from 0 to 100% over 100 min (flow rate: 1 ml/min).

Other methods known in the art may be used to synthesize or obtain the peptides according to the present invention. All peptides were synthesized as carboxyamides ($—CONH_2$) which creates a charge-neutral end more similar to a peptide bond than the negatively charged —COOH end. Nevertheless, peptides having the negatively charged —COOH end are contemplated herein.

Activity Assays

Flow Cytometry.

The activity of peptides of the present invention was measured by flow cytometry as previously described. See Nemeth et al. (2006) Blood 107:328-333, which is herein incorporated by reference. ECR293/Fpn-GFP, a cell line stably transfected with a ponasterone-inducible ferroportin construct tagged at the C-terminus with green fluorescent protein was used. See Nemeth et al. (2004) Science 306: 2090-2093, which is herein incorporated by reference. Briefly, the cells were plated on poly-D-lysine coated plates in the presence of 20 μM FAC, with or without 10 μM ponasterone. After 24 hours, ponasterone was washed off, and cells were treated with peptides for 24 hours. Cells were then trypsinized and resuspended at $1 \times 10^6$ cells/ml, and the intensity of green fluorescence was analyzed by flow cytometry. Flow cytometry was performed on FAC Scan (fluorescence activated cell scanner) Analytic Flow Cytometer (Becton Dickinson, San Jose, Calif.) with CellQuest version 3.3 software (Becton Dickinson). Cells not induced with ponasterone to express Fpn-GFP were used to establish a gate to exclude background fluorescence. Cells induced with ponasterone, but not treated with any peptides, were used as the positive control. Each peptide was tested over the range of concentrations (0, 0.01, 0.03, 0.1, 0.3, 1, 3 and 10 μM). Each peptide treatment was repeated independently 3 to 6 times. For each concentration of peptide, the results were expressed as a fraction of the maximal activity ($F_{Hep25}$) of Hep25 (in the dose range 0.01-10 μM), according to the formula $1-((F_x-F_{Hep25})/(F_{untreated}-F_{Hep25}))$, where F was the mean of the gated green fluorescence and x was the peptide. The $IEC_{50}$ concentrations are set forth in the Table 1.

Ferritin Assay.

Cells treated with peptides having hepcidin activity will retain iron and contain higher amounts of ferritin. Thus, following ferritin assay may be used to identify mini-hepcidins according to the present invention. Briefly, HEK293-Fpn cells are incubated with 20 μM FAC with or without 10 μM ponasterone. After 24 hours, ponasterone is washed off, and hepcidin derivatives are added for 24 hours in the presence of 20 μM FAC. Cellular protein is extracted with 150 mM NaCl, 10 mM EDTA, 10 mM Tris (pH 7.4), 1% Triton X-100, and a protease inhibitor cocktail (Sigma-Aldrich, St Louis, Mo.). Ferritin levels are determined by an enzyme-linked immunosorbent assay (ELISA) assay (Ramco Laboratories, Stafford, Tex., or Biotech Diagnostic, Laguna Niguel, Calif.) according to the manufacturer's instructions and are normalized for the total protein concentration in each sample, as determined by the bicinchoninic acid (BCA) assay (Pierce, Rockford, Ill.).

In Vivo Assays. Serum Iron Assay.

The decrease in serum iron after peptide administration is the principal measure of hepcidin activity. Thus, as provided herein, the hepcidin activity of selected peptides of the present invention were assayed in vivo by measuring serum iron in test subjects. Briefly, C57/Bl6J mice were maintained on NIH 31 rodent diet (333 parts per million (ppm) iron; Harlan Teklad, Indianapolis, Ind.). Two weeks before the experiment, the mice were switched to a diet containing about 2-4 ppm iron (Harlan Teklad, Indianapolis, Ind.) in order to suppress endogenous hepcidin. Peptide stocks were diluted to desired concentrations in sterile phosphate buffered saline (PBS) or other diluents as described next. Mice were subjected to the following treatments: (a) Injected intraperitoneally either with 100 μl PBS (control) or with 50 μg peptide in 100 μl PBS; (b) Injected with 100 μl of peptide (or PBS) mixed with 500 μg empty liposomes Coatsome EL series (NOF, Tokyo, Japan) (prepared as per manufacturer's recommendation); (c) Injected with 100 μl peptides (or PBS) solubilized with SL220 solubilization agent (NOF, Tokyo, Japan); (d) Gavaged with 250 μl of peptide (or PBS) in 1× solvent (Cremophor EL (Sigma)/ethanol/PBS; (12.5:12.5: 75)). Mice were sacrificed 4 hours later, blood was collected by cardiac puncture, and serum was separated using Microtainer tubes (Becton Dickinson, Franklin Lakes, N.J.). Serum iron was determined by using a colorimetric assay (Diagnostic Chemicals, Oxford, Conn.), which was modified for the microplate format so that 10 μl serum was used per measurement. The results were expressed as the percentage of decrease in serum iron when compared with the average value of serum iron levels in PBS-treated mice.

Figure 5:
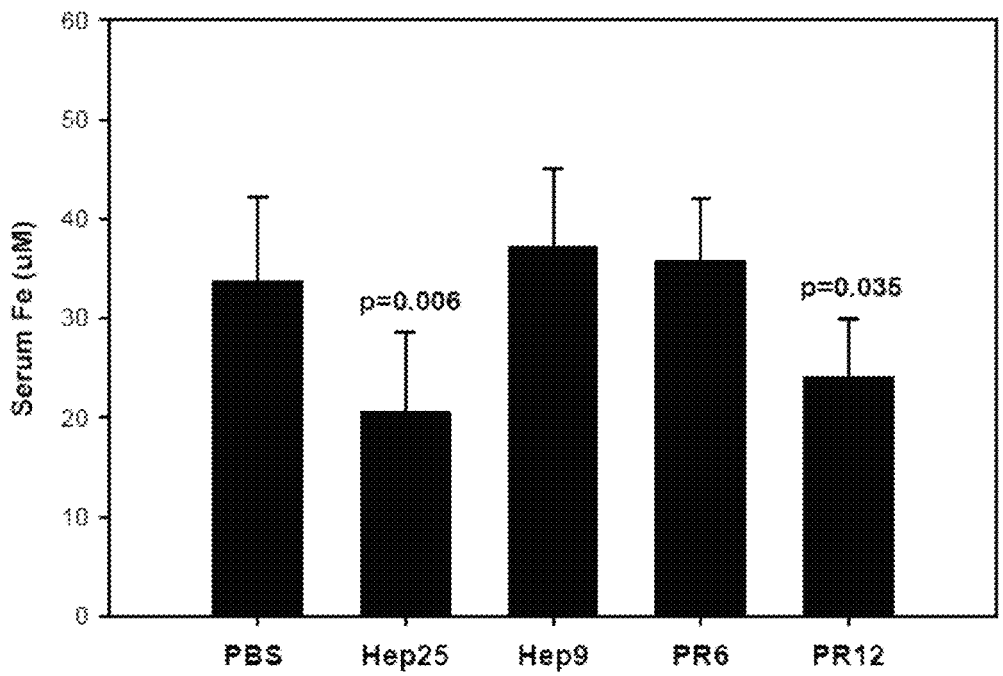
FIG. 5 is a graph showing in vivo effect (as measured by serum iron levels in mice) of mini-hepcidins Hep1-9, PR6 and PR12 compared to Hep25 or control (PBS). The peptides were injected intraperitoneally, 50 µg peptide per mouse.

As shown in FIG. 5, intraperitoneal (i.p.) administration of 50 μg PR12 per mouse in PBS caused a significant decrease in serum iron after 4 hours, when compared to i.p. administration of PBS. The serum iron decrease was similar to that caused by i.p. injection of 50 μg of Hep25. Injection (i.p.) of Hep9 did not result in a serum iron decrease. PR12 is a retroinverted form of Hep9, and is resistant to proteolysis because of the retroinverted structure. The experiment indicates that increased proteolytic resistance improves the activity of mini-hepcidins.

Figure 6:
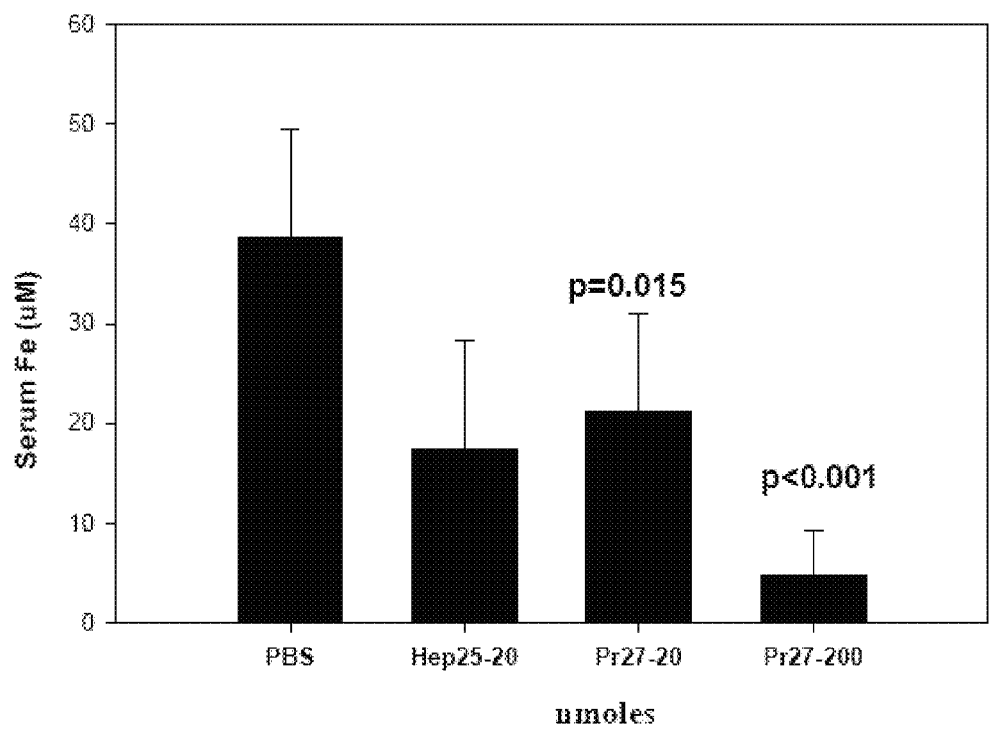
FIG. 6 is a graph showing in vivo effect (as measured by serum iron levels in mice) of mini-hepcidin PR27 injected intraperitoneally (20 and 200 nmoles). The amount of injected Hep25 was 20 nmoles.

As shown in FIG. 6, i.p. administration of 200 nmoles of riHep7ΔDT in PBS resulted in serum iron concentrations significantly lower than those achieved after injection of PBS, and also lower than i.p. injection of 20 nmoles of Hep25. Administration of 20 nmoles of riHep7ΔDT slightly but not significantly reduced serum iron concentrations. The experiment indicates that after i.p. injection peptides as small as 7 amino acids are able to display activity comparable to Hep25.

Figure 7:
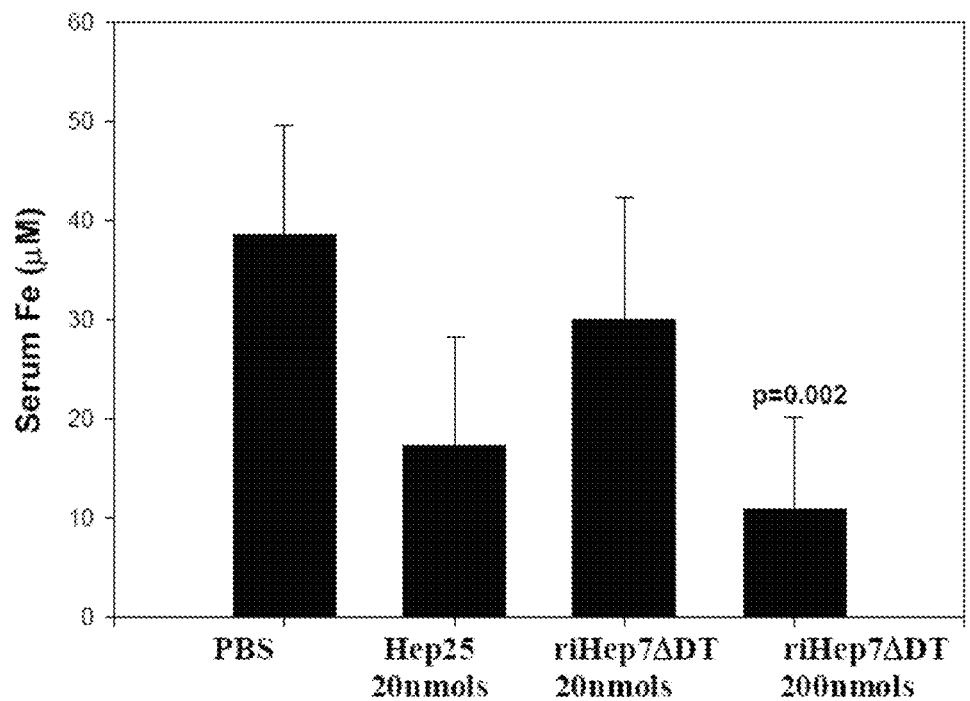
FIG. 7 is a graph showing in vivo effect (as measured by serum iron levels in mice) of mini-hepcidin riHep7ΔDT injected intraperitoneally (20 and 200 nmoles). The amount of injected Hep25 was 20 nmoles.

As shown in FIG. 7, i.p. administration of 20 nmoles PR27 in PBS caused a serum iron decrease comparable to that caused by i.p. administration of 20 nmoles Hep25. This indicated that mini-hepcidin can achieve similar potency to Hep25 in vivo. Higher concentration of PR27 (200 nmoles) caused even greater decrease in serum iron concentrations.

Figure 8:
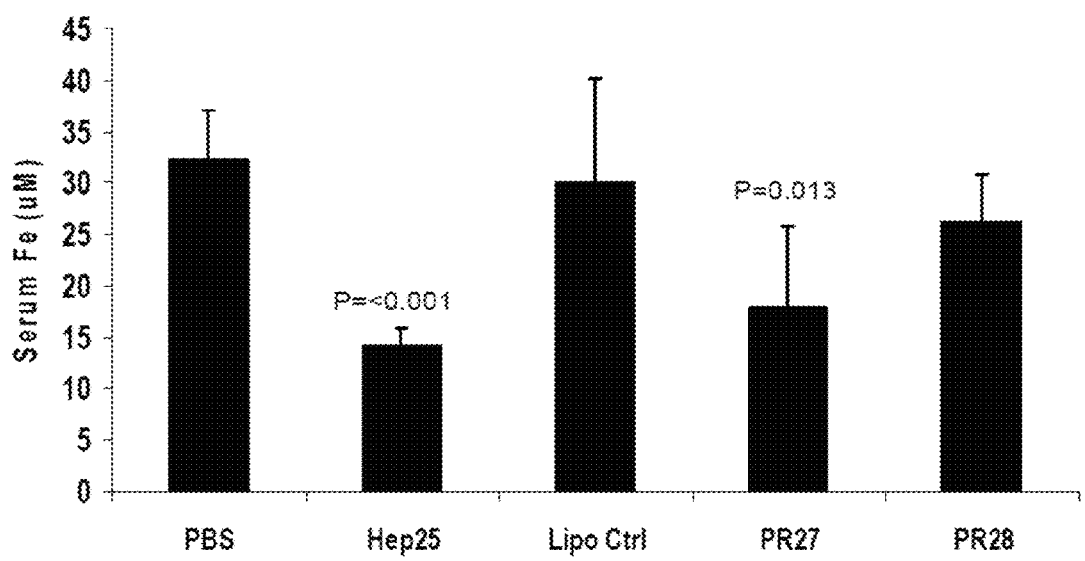
FIG. 8 is a graph showing in vivo effect (as measured by serum iron levels in mice) of mini-hepcidins PR27 and PR28 which were first mixed with liposomes and injected intraperitoneally (20 nmoles). The amount of injected Hep25 was 20 nmoles.

As shown in FIG. 8, i.p. administration of 20 nmoles PR27 in liposomal solution also caused a serum iron decrease similar to that caused by i.p. administration of 20 nmoles Hep25. Administration of liposomal solution by itself did not affect serum iron levels. The liposomal solution was prepared by mixing 100 µl of PBS with 500 µg empty liposomes COATSOME EL series (NOF, Tokyo, Japan) (prepared as per manufacturer's recommendation). Mini-hepcidin PR28 dissolved in liposomal solution, however, showed lesser ability to decrease serum iron than PR27. The experiment indicates that suspension of peptides in liposomes does not affect their activity. Thus, liposomes may be useful for oral administration of peptides according to the present invention.

Figure 9:
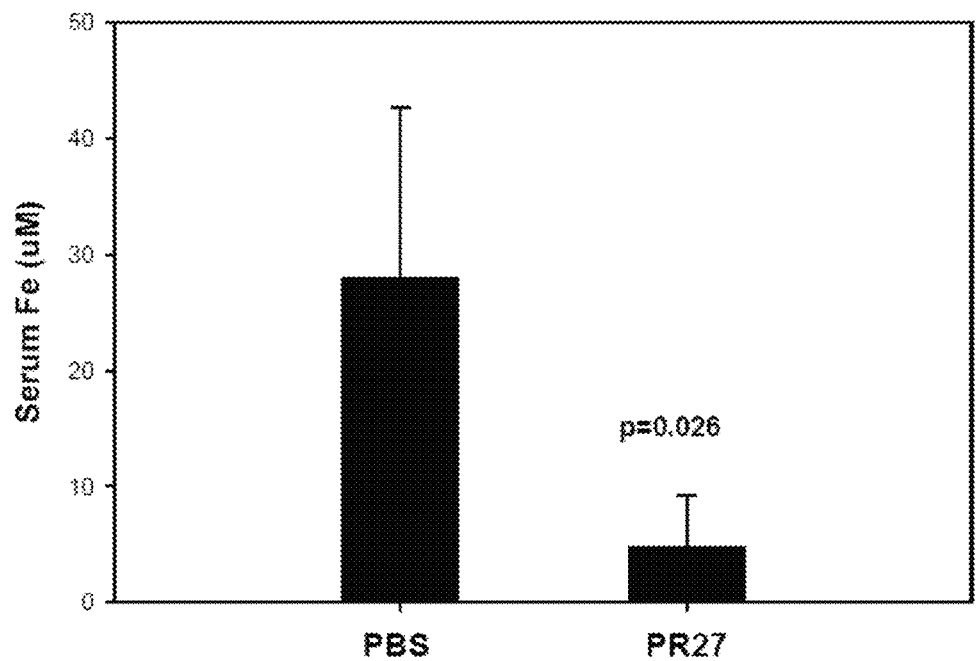
FIG. 9 is a graph showing in vivo effect (as measured by serum iron levels in mice) of mini-hepcidin PR27 after oral administration by gavage (200 nmoles).

As shown in FIG. 9, oral administration of PR27 200 nmoles by gavage in a cremophore EL solution caused a decrease in serum iron in mice as compared to oral administration of PBS in the same formulation. Cremophor EL increases solubility of chemicals, and is frequently used excipient or additive in drugs. Cremophor EL solution was prepared by mixing Cremophor EL (Sigma), ethanol and PBS in a ratio 12.5:12.5:75. 250 µl of the solution was administered by gavage to mice.

Thus, the present invention may be used to decrease serum iron in subjects. A preferred mini-hepcidin according to the present invention is a retroinverted peptide which comprises a PEG molecule, such as PEG11, linked to its N-terminal amino acid. In some embodiments, the PEG molecule is linked to palmitoyl group or diaminopropionic acid linked to one or more palmitoyl groups.

In addition to assaying the effect on serum iron content, other in vivo assays known in the art may be conducted to identify mini-hepcidins according to the present invention and/or determine the therapeutically effective amount of a given peptide or mini-hepcidin according to the present invention. Examples of such assays include the following:

Tissue Iron Assay.

In addition to or instead of the serum iron assay above, tissue iron distribution can be determined by enhanced Perl's stain of liver and spleen sections obtained from the treated mice. Briefly, the tissue sections are fixed in 4% paraformaldehyde/PBS, incubated in Perl's solution (1:1, 2% HCl and 2% potassium ferrocyanide) and diaminobenzidine in 0.015% hydrogen peroxide. Tissue non-heme iron may be quantitated using the micromethod of Rebouche et al. (2004) J Biochem Biophys Methods. 58(3):239-51; Pak et al. (2006) Blood 108(12):3730-5. 100 mg pieces of liver and spleen are homogenized and acid is added to release non-heme bound iron which is detected by colorimetric reaction using ferrozine and compared to controls. Treatment with mini-hepcidins would be expected to cause redistribution of iron from other tissues to the spleen. Over weeks to months, the administration of mini-hepcidins would be expected to decrease tissue iron content in all tissues because of diminished dietary iron absorption.

Hematology Assays.

Hematology assays may be used to identify mini-hepcidins according to the present invention and/or determine the therapeutically effective amount of a given peptide or mini-hepcidin according to the present invention. Briefly, blood from treated subjects is collected into heparin-containing tubes. Hemoglobin, RBC, MCV, EPO, white cell parameters, reticulocyte counts, and reticulocyte Hgb content are determined using methods known in the art and compared to controls. Treatment with mini-hepcidins would be expected to cause a decrease in MCV and diminish the Hgb content of reticulocytes. Administration of mini-hepcidins in excessive amounts would be expected to decrease Hgb.

Iron Export Assays.

Iron ($^{55}$Fe) export assays known in the art using primary hepatocytes and macrophages may be used to identify mini-hepcidins according to the present invention and/or determine the therapeutically effective amount of a given peptide or mini-hepcidin according to the present invention. Peptides having hepcidin activity will diminish or decrease the release of $^{55}$Fe from cells. Briefly, cells are incubated with $^{55}$Fe-NTA or $^{55}$Fe-Tf for 36 hours. After washing off unincorporated $^{55}$Fe, cells are treated with a given peptide or a control. In case of ferroportin mutants, the transfection is performed prior to addition of $^{55}$Fe and expression allowed to proceed during the 36 hour iron-loading period. Aliquots of the media are collected after 1, 4, 8, 24, 36, 48 and 72 hours and radioactivity is determined by a scintillation counter. Cell-associated radioactivity can be measured by centrifuging cells through silicone oil to lower the non-specific binding of radiolabeled iron to cells using methods known in the art.

To determine whether a given peptide modifies the internalization and degradation of endogenous ferroportin, the protein levels and cellular distribution of ferroportin in hepatocytes and macrophages treated with the peptide may be assayed using Western blotting, immunohistochemistry and ferroportin antibodies known in the art.

Modified Mini-Hepcidins

Additional mini-hepcidins according to the present invention are shown in Table 3 and Table 4 as follows:

TABLE 3

| Name | 1 | 2 | 3 | 4 | 5 | 6 | 7 | 8 | 9 | 10 | EC$_{50}$ (nM) in vitro | Active @ 20 nmoles/ mouse IP |
|---|---|---|---|---|---|---|---|---|---|---|---|---|
| Hept10wt (SEQ ID NO: 2) | D | T | H | F | P | I | C | I | F | C | | |
| PR42' (SEQ ID NO: 67) | D | T | H | Dpa | P | R | C | R | Dpa | | 30 | |
| PR47 (SEQ ID NO: 68) | D | T | H | Dpa | P | I | C | I | F-R4 | | 50 | N |
| PR48 (SEQ ID NO: 69) | D | T | H | Dpa | P | I | C | I | Dpa-R4 | | 50 | N |

TABLE 3-continued

| Name | 1 | 2 | 3 | 4 | 5 | 6 | 7 | 8 | 9 | 10 | EC$_{50}$ (nM) in vitro | Active @ 20 nmoles/ mouse IP |
|---|---|---|---|---|---|---|---|---|---|---|---|---|
| PR49 (SEQ ID NO: 70) | | | H | Dpa | P | I | C | I | F-R4 | | <10 | N |
| PR50 (SEQ ID NO: 71) | | | H | Dpa | P | I | C | I | Dpa-R4 | | <10 | N |
| PR51 (SEQ ID NO: 72) | D | T | H | Dpa | P | V | C | V | F-R4 | | 100 | |
| PR52 (SEQ ID NO: 73) | D | T | H | Dpa | P | L | C | L | F-R4 | | <10 | |
| PR53 (SEQ ID NO: 74) | N-MeAsp | T | H | Dpa | P | I | C | I | bhPhe-R14 | | 10 | |
| PR54 (SEQ ID NO: 75) | N-MeAsp | T | H | Dpa | bhPro | I | C | I | bhPhe-R14 | | 10 | |
| PR55 (SEQ ID NO: 76) | N-MeAsp | T | H | Dpa | P | Ach | C | Ach | F-R14 | | 10 | |
| PR56 (SEQ ID NO: 77) | N-MeAsp | T | H | Dpa | Oic | R | C | R | bhPhe-R14 | | 15 | |
| PR57 (SEQ ID NO: 78) | N-MeAsp | T | H | Dpa | bhPro | R | C | R | bhPhe-R14 | | 2 | Y |
| PR58 (SEQ ID NO: 79) | Ida | T | H | Dpa | P | I | C | I | bhPhe-R14 | | 1 | |
| PR59 (SEQ ID NO: 80) | Ida | T | H | Dpa | bhPro | I | C | I | bhPhe-R14 | | 2 | N |
| PR60 (SEQ ID NO: 81) | Ida | T | H | Dpa | P | Ach | C | Ach | F-R14 | | 3 | Y* |
| PR61 (SEQ ID NO: 82) | Ida | T | H | Dpa | bhPro | R | C | R | bhPhe-R14 | | 10-100 | Y (also by SQ) |

R4 = Palmitoyl-(PEG11)-, PEG11 = O-(2-aminoethyl)-O'-(2-carboxyethyl)-undecaethyleneglycol
R14= Palmitoyl-PEG-miniPEG3-, and "miniPEG3" = 11-amino-3,6,9-trioxaundecanoic acid
Underlined residues = D amino acids
"—" indicates a covalent bond, e.g. point of attachment to the given peptide
IP = intraperitoneal administration,
SQ = subcutaneous administration
*= Exhibits detectable and reproducible activity at about 50% lower than the most active compounds in Table 3 and 4. As used herein, "Active" means that at 4 hours after injection serum iron in peptide-injected mice decreased statistically significantly (p < 0.05) compared to solvent-injected mice. "Activity" refers to the % decrease of serum iron 4 hours after injection compared to solvent-treated mice.
In some embodiments, PEG11 can be substituted with miniPEG3 and miniPEG3 can be substituted with PEG11.

TABLE 4

| Name | 1 | 2 | 3 | 4 | 5 | 6 | 7 | 8 | 9 | 10 | Active @ 20 nmoles/ mouse IP | Active @ 20 nmoles/ mouse SQ |
|---|---|---|---|---|---|---|---|---|---|---|---|---|
| Hep10wt (SEQ ID NO: 2) | D | T | H | F | P | I | C | I | F | C | | |
| PR62 (SEQ ID NO: 83) | Ida | T | H | Dpa | bhPro | R | C | R | bhPhe-R14 | | N | |
| PR63 (SEQ ID NO: 84) | Ida | T | H | Dpa | bhPro | N-MeArg | C | N-MeArg | bhPhe-R14 | | Y | |
| PR64 (SEQ ID NO: 85) | Ida | T | H | Dpa | bhPro | bhArg | C | bhArg | bhPhe-R14 | | N | |
| PR65 (SEQ ID NO: 86) | Ida | T | H | Dpa | bhPro | R | C | R | bhPhe-R15 | | Y | Y |
| PR66 (SEQ ID NO: 87) | Ida | T | H | Dpa | bhPro | R | C | R | bhPhe | | Y | N |
| PR67 (SEQ ID NO: 88) | Ida | T | H | Dpa | bhPro | R | Cys(S-S-Pal) | R | bhPhe | | Y | Y |
| PR68 (SEQ ID NO: 89) | Ida | T | H | Dpa | bhPro | R | Cys(S-S-cysteamine-Pal) | R | bhPhe | | Y | |
| PR69 (SEQ ID NO: 90) | Ida | T | H | Dpa | bhPro | R | Cys(S-S-Cys-NHPal) | R | bhPhe | | Y* | |
| PR70 (SEQ ID NO: 91) | Ida | T | H | Dpa | bhPro | R | Cys(S-S-Cys) | R | bhPhe-R14 | | Y* | |
| PR71 (SEQ ID NO: 92) | Ida(NHPal) | T | H | Dpa | bhPro | R | C | R | bhPhe | | Y* | N |
| PR72 (SEQ ID NO: 93) | Ida | T | H | Dpa | bhPro | R | C | R | bhPhe | Ida(NHPal) | Y | N |
| PR73 (SEQ ID NO: 94) | Ida | T | H | Dpa | bhPro | R | C | R | bhPhe | Ahx-Ida(NHPal) | Y | |
| PR74 (SEQ ID NO: 95) | Ida | T | H | Dpa | bhPro | R | C | R | bhPhe | Ahx-Ida(NBzI2) | Y | |

TABLE 4-continued

| Name | 1 | 2 | 3 | 4 | 5 | 6 | 7 | 8 | 9 | 10 | Active @ 20 nmoles/mouse IP | Active @ 20 nmoles/mouse SQ |
|---|---|---|---|---|---|---|---|---|---|---|---|---|
| PR75 (SEQ ID NO: 96) | Ida | T | H | Dpa | bhPro | R | C | R | bhPhe-R16 | | N | |
| PR76 (SEQ ID NO: 97) | D | T | H | F | P | R | Cys(S-S-tBut) | R | W-R17 | | N | |
| PR77 (SEQ ID NO: 98) | D | T | H | F | P | R | Cys(S-S-tBut) | R | W-R18 | | N | |
| PR78 (SEQ ID NO: 99) | D | T | H | F | P | R | Cys(S-S-tBut) | R | W-R19 | | N | |
| PR79 (SEQ ID NO: 100) | D | T | H | F | P | R | Cys(S-S-tBut) | R | W-R20 | | N | |
| PR82 (SEQ ID NO: 101) | Ida | T | H | Dpa | bhPro | R | C | R | W | Ahx-Ida(NHPal) | | Y |

R4 = Palmitoyl-(PEG11)-, wherein PEG11 = O-(2-aminoethyl)-O'-(2-carboxyethyl)-undecaethyleneglycol
R14 = Palmitoyl-PEG-miniPEG3-, and "miniPEG3" = 11-amino-3,6,9-trioxaundecanoic acid
R15 = Palmitoyl-PEG-
R16 = S-(Palmityl)thioglycolic-PEG-
R17 = Butanoyl-PEG11-
R18 = Octanoyl-PEG11-
R19 = Palmitoyl-PEG11-
R20 = Tetracosanoyl-PEG11-
Ahx-Ida(NHPal) = Aminohexanoic acid spacer between peptide residue 9 and Ida residue; Palmitylamine amide on Ida side chain
Ida(NHPal) = Palmitylamine amide on Ida side chain
Ida(NBzI2) = N,N'-Dibenzylamine amide on Ida side chain
Cys(S-S-Pal) = Palmitoyl attached to Cys7 via a disulfide bond
Cys(S-S-cysteamine-Pal) = Palmitoyl attached to Cys7 via SS-Cysteamine
Cys(S-S-Cys-NHPal) = Palmitylamine attached to Cys7 via another Cys
Cys(S-S-Cys) = Cys attached to Cys7 via disulfide bond
Underlined residues = D amino acids
"—" indicates a covalent bond, e.g. point of attachment to the given peptide
*= detectable and reproducible activity but at least 50% lower than other active compounds in Table 4. As used herein, "Active" means that the injection of the compound resulted in statistically significant (p < 0.05) lowering of serum iron compared to solvent injection when measured 4 hours after administration. "Activity" refers to the % decrease of serum iron 4 hours after injection compared to solvent-treated mice.
IP = intraperitoneal administration,
SQ = subcutaneous administration
In some embodiments, PEG11 can be substituted with miniPEG3.
In some embodiments, miniPEG3 can be substituted with PEG11.
In some embodiments, PEG can be substituted with PEG11, but not miniPEG3.

In Tables 3 and 4, PR47, PR48, PR49, PR50, PR51, PR52, PR76, PR77, PR78, and PR79 are retroinverted mini-hepcidins and are shown, left to right, from their C-terminus to their N-terminus in order to exemplify the alignment between their amino acid residues and that of residues 1-10 of Hep25. Thus, the conventional recitation of these retroinverted mini-hepcidins from their N-terminus to their C-terminus are as follows (D amino acids are underlined):

PR47: R4-F-I-C-I-P-Dpa-H-T-D
PR48: R4-Dpa-I-C-I-P-Dpa-H-T-D
PR49: R4-F-I-C-I-P-Dpa-H
PR50: R4-Dpa-I-C-I-P-Dpa-H
PR51: R4-F-V-C-V-P-Dpa-H-T-D
PR52: R4-F-L-C-L-P-Dpa-H-T-D
PR76: R17-W-R-Cys(S-S-tBut)-R-P-F-H-T-D
PR77: R18-W-R-Cys(S-S-tBut)-R-P-F-H-T-D
PR78: R19-W-R-Cys(S-S-tBut)-R-P-F-H-T-D
PR79: R20-W-R-Cys(S-S-tBut)-R-P-F-H-T-D

As shown in Table 4, the route of administration may play a role in the activity of the given mini-hepcidin (compare, for example, PR65 and PR66). Thus, the indication of no activity of some of the mini-hepcidins in Tables 3 and 4 should not be interpreted as indicating that the given mini-hepcidin lacks any activity at any route of administration and/or dosage. In fact, as shown in Table 3, quite a few of such mini-hepcidins exhibit significant in vitro activity at considerably lower dosages as the original mini-hepcidins.

These additional mini-hepcidins are modifications of the mini-hepcidins as set forth in PCT/US2009/066711 (hereinafter referred to as "original mini-hepcidins" and having the Structural Formula I). As used herein, mini-hepcidins which are modifications of the original mini-hepcidins are referred to herein as "modified mini-hepcidins". As used herein, "mini-hepcidins" refers to both original mini-hepcidins and modified mini-hepcidins. Modified mini-hepcidins according to the present invention have the following Structural Formula IA or IB:

$$A1-A2-A3-A4-A5-A6-A7-A8-A9-A10 \qquad IA$$

$$A10-A9-A8-A7-A6-A5-A4-A3-A2-A1 \qquad IB$$

A1 is Asp, D-Asp, Glu, D-Glu, pyroglutamate, D-pyroglutamate, Gln, D-Gln, Asn, D-Asn, or an unnatural amino acid commonly used as a substitute thereof such as bhAsp, Ida, Ida(NHPal), and N-MeAsp, preferably Ida and N-MeAsp;

A2 is Thr, D-Thr, Ser, D-Ser, Val, D-Val, Ile, D-Ile, Ala, D-Ala or an unnatural amino acid commonly used as a substitute thereof such as Tle, Inp, Chg, bhThr, and N-MeThr;

A3 is His, D-His, Asn, D-Asn, Arg, D-Arg, or an unnatural amino acid commonly used as a substitute thereof such as L-His(π-Me), D-His(π-Me), L-His(τ-Me), or D-His(τ-Me);

A4 is Phe, D-Phe, Leu, D-Leu, Ile, D-Ile, Trp, D-Trp, Tyr, D-Tyr, or an unnatural amino acid commonly used as a substitute thereof such as Phg, bhPhe, Dpa, Bip, 1Nal, 2Nal, bhDpa, Amc, PheF5, hPhe, Igl, or cyclohexylalanine, preferably Dpa;

A5 is Pro, D-Pro, Ser, D-Ser, or an unnatural amino acid commonly used as a substitute thereof such as Oic, bhPro, trans-4-PhPro, cis-4-PhPro, cis-5-PhPro, and Idc, preferably bhPro;

A6 is Arg, D-Arg, Ile, D-Ile, Leu, D-Leu, Thr, D-Thr, Lys, D-Lys, Val, D-Val, or an unnatural amino acid commonly used as a substitute thereof such as D-Nω,ω-dimethyl-arginine, L-Nω,ω-dimethyl-arginine, D-homoarginine, L-homoarginine, D-norarginine, L-norarginine, citrulline, a modified Arg wherein the guanidinium group is modified or substituted, Norleucine, norvaline, bhIle, Ach, N-MeArg, and N-MeIle, preferably Arg;

A7 is Cys, D-Cys, Ser, D-Ser, Ala, D-Ala, or an unnatural amino acid commonly used as a substitute thereof such as Cys(S-tBut), homoCys, Pen, (D)Pen, preferably S-tertiary butyl-cysteine, Cys(S-S-Pal), Cys(S-S-cysteamine-Pal), Cys(S-S-Cys-NHPal), and Cys(S-S-Cys) or any amino acid derivative having an exchangeable cysteine;

A8 is Arg, D-Arg, Ile, D-Ile, Leu, D-Leu, Thr, D-Thr, Lys, D-Lys, Val, D-Val, or an unnatural amino acid commonly used as a substitute thereof such as D-Nω,ω-dimethyl-arginine, L-Nω,ω-dimethyl-arginine, D-homoarginine, L-homoarginine, D-norarginine, L-norarginine, citrulline, a modified Arg wherein the guanidinium group is modified or substituted, Norleucine, norvaline, bhIle, Ach, N-MeArg, and N-MeIle, preferably Arg;

A9 is Phe, D-Phe, Leu, D-Leu, Ile, D-Ile, Tyr, D-Tyr, Trp, D-Trp, Phe-$R^a$, D-Phe-$R^a$, Dpa-$R^a$, D-Dpa-$R^a$, Trp-$R^a$, bhPhe-$R^a$, or an unnatural amino acid commonly used as a substitute thereof such as PheF5, N-MePhe, benzylamide, 2-aminoindane, bhPhe, Dpa, Bip, 1Nal, 2Nal, bhDpa, and cyclohexylalanine, which may or may not have $R^a$ linked thereto, preferably bhPhe and bhPhe-$R^a$, wherein $R^a$ is palmitoyl-PEG-, wherein PEG is PEG11 or mini-PEG3, palmitoyl-PEG-PEG, wherein PEG is PEG11 or miniPEG3, butanoyl (C4)-PEG11-, octanoyl (C8, Caprylic)-PEG11-, palmitoyl (C16)-PEG11-, or tetracosanoyl (C24, Lignoceric)-PEG11-; and A10 is Cys, D-Cys, Ser, D-Ser, Ala, D-Ala, or an unnatural amino acid such as Ida, Ida(NHPal)Ahx, and Ida(NBzl2)Ahx;

wherein the carboxy-terminal amino acid is in amide or carboxy-form;

wherein at least one sulfhydryl amino acid is present as one of the amino acids in the sequence (and preferably, the sulfydryl group is capable of exchange); and wherein A1, A1 to A2, A10, or a combination thereof are optionally absent, with the proviso that the peptide is not one of the peptides as set forth in Table 1. In some embodiments, the modified mini-hepcidin forms a cyclic structure by a disulfide bond. In some embodiments, the N-terminal amino acid is a free amine. In some embodiments, the N-terminal amino acid is a blocked amine such as with an acetyl group. In some embodiments, A6 and/or A8 is a lysine derivative such as N-ε-Dinitrophenyl-lysine, N-ε-Methyl-lysine, N,N-ε-Dimethyl-lysine, and N,N,N-ε-Trimethyl-lysine.

Five of the modified mini-hepcidins in Table 4 contain tryptophan in order to facilitate measurements of their concentration. Thus, in some embodiments, the modified mini-hepcidins of the present invention contain tryptophan. In some embodiments, the tryptophan residue(s) is deleted or substituted with another amino acid. Other modified mini-hepcidins were made by modifying original mini-hepcidins by substituting the two isoleucines flanking the cysteine with arginines or arginine derivatives. Unexpectedly, it was found that substituting these isoleucines with arginines resulted in mini-hepcidins with increased activity. It is believed that the unexpectedly superior activity is the result of the presence of arginine at the 6th amino acid position and/or the 8th amino acid position. Thus, in some embodiments, the amino acid residue at position A6 and/or A8 of structural formula I is arginine. Additional modifications of such mini-hepcidins also resulted in unexpectedly higher activities. The modified mini-hepcidins according to the present invention unexpectedly exhibit superior activity as compared to the modified mini-hepcidins exemplified in U.S. Ser. No. 13/131,792. In addition, it was found that many of the modified mini-hepcidins retain their activity when subcutaneously administered.

In some embodiments the N-terminal amino acid has a free amine. In some embodiment the N-terminal amine is blocked with a group that removes its charge, preferably an acetyl or formal group. In some embodiments the N-terminal amine is modified to be conjugated with an acyl chain with preferred embodiments with a fatty acid such as caprylic, capric, lauric, myristic, palmitic, or stearic such that an acyl chain is on the N-terminus. The acyl chain also may be attached via a linker commonly known in the art, e.g. a polyethylene glycol linker, preferably PEG3.

In some embodiments, the side-chain of amino acid A1 can be modified as indicated for the N-terminal amine. For example, the free carbonyl group on the amino acid A1 can be modified, e.g. blocked by an acyl group such as palmitoyl (see PR71).

In some embodiment, A4 is a bulky hydrophobic amino acid such as Phe, Tyr, Trp, Leu, or Ile or any unnatural amino acid commonly used as a substitute thereof that contains 4 or more carbons in its side-chain, preferably a cyclic structure such as Phg, Bip, 1Nal, 2Nal, Amc, PheF5, Igl (L-2-indanylglycine) or Cha (L-cyclohexylalanine), preferably Dpa. In some embodiments, A4 contains the betahomo form of the above bulky hydrophobic amino acids, e.g. bhPhe, or bhDpa. Other modifications to the side-chain include aromatic substituents such as those disclosed in Wang et al. (2002) Tetrahedron 58:3101-3110 and Wang et al. (2002) Tetrahedron 58:7365-7374. In some embodiments, the A4 residue is a D-amino acid.

In some embodiments, the amino acid at position A9 is a bulky hydrophobic amino acid such as Phe, Tyr, Trp, Leu, or Ile or any unnatural amino acid commonly used as a substitute thereof that contains 4 or more carbons in its side-chain, preferably a cyclic structure such as Phg, Dpa, Bip, 1Nal, 2Nal, Amc, PheF5, Igl or Cha, such as a cyclic or aromatic group containing 1 or more rings or aromatic substituents. In some embodiments, the A9 residue is Dpa or Trp.

In some embodiments, the mini-hepcidins of the present invention are modified or formulated in order to maintain and/or increase its in vivo bioavailability. For example, in some embodiments, the peptide chain is conjugated with an acyl chain. In some embodiments, the acyl chain may be conjugated to the N-terminal or C-terminal amino acid or a Cysteine residue. In some embodiments, the acyl chain is conjugated to the A7 residue. The acyl chain may include a fatty acid such as caprylic, capric, lauric, myristic, palmitic, or stearic. The acyl chain also may also contain a spacer such as a polyethylene glycol spacer. In some embodiments, the spacer is a polyethylene glycol spacer (1-11 PEG), preferably PEG3 or PEG11. In some embodiments, the spacer comprises of an amino acid where the number of carbons between the amino group and the carboxylic acid group is separated by about 2-8 carbons, such as 6-aminohexanoic acid (see, for example, PR73). Other suitable spacers include a hydrophobic structure that has a ring and/or aromatic character (see, for example, PR74).

The modified mini-hepcidins were demonstrated in a mouse hemochromatosis model that daily administration of the modified mini-hepcidins, e.g. PR65, prevented iron overload. Therefore, the modified mini-hepcidins according to the present invention, alone or in combination with one or more original mini-hepcidins, may be administered to subjects in order to treat, e.g. inhibit and/or reduce, iron overload in subjects, such as humans. Therefore, modified and original mini-hepcidins according to the present invention may be used in medicaments and treatments in order to treat iron overload disorders, e.g. beta-thalassemia and hereditary hemochromatosis, by inhibiting and/or reducing iron overload in subjects. In some embodiments, at least one modified mini-hepcidin and/or at least one original mini-hepcidin is administered to subjects before, during, after, or a combination thereof, symptoms of iron overload are observed and/or being diagnosed as having an iron overload disorder.

Thus, in some embodiments, one or more modified mini-hepcidins, alone or in combination with one or more original mini-hepcidins, are provided in the form of a composition which comprises a carrier suitable for its intended purpose. The compositions may also include one or more additional ingredients suitable for its intended purpose. For example, for assays, the compositions may comprise liposomes, niclosamide, SL220 solubilization agent (NOF, Japan), cremophor EL (Sigma), ethanol, and DMSO. For treatment of an iron overload disease, the compositions may comprise different absorption enhancers and protease inhibitors, solid microparticles or nanoparticles for peptide encapsulation (such as chitosan and hydrogels), macromolecular conjugation, lipidization and other chemical modification.

The present invention also provides kits comprising one or more modified mini-hepcidins, alone or in combination with one or more original mini-hepcidins, and/or compositions of the present invention packaged together with reagents, devices, instructional material, or a combination thereof. For example, the kits may include reagents used for conducting assays, drugs and compositions for diagnosing, treating, or monitoring disorders of iron metabolism, devices for obtaining samples to be assayed, devices for mixing reagents and conducting assays, and the like.

As the peptides of the present invention exhibit hepcidin activity, i.e. act as agonists of ferroportin degradation, one or more modified mini-hepcidins, alone or in combination with one or more original mini-hepcidins, may be used to treat iron overload diseases. For example, one or more modified mini-hepcidins, alone or in combination with one or more original mini-hepcidins, may be administered to a subject to ameliorate the symptoms and/or pathology associated with iron overload in iron-loading anemias (especially β-thalassemias) where phlebotomy is contraindicated and iron chelators are the mainstay of treatment but are often poorly tolerated. One or more modified mini-hepcidins, alone or in combination with one or more original mini-hepcidins, may be used to treat hereditary hemochromatosis, especially in subjects who do not tolerate maintenance phlebotomy. One or more modified mini-hepcidins, alone or in combination with one or more original mini-hepcidins, may be used to treat acute iron toxicity. In some embodiments, treatment with one or more modified mini-hepcidins, alone or in combination with one or more original mini-hepcidins, may be combined with phlebotomy or chelation.

Thus, one or more modified mini-hepcidins, alone or in combination with one or more original mini-hepcidins may be administered to a subject, preferably a mammal such as a human. In some embodiments, the administration to the subject is before, during, and/or after the subject exhibits an increase in iron levels and/or abnormally high levels of iron. In some embodiments, the subject to be treated is one who is at risk of having high levels of iron and/or has a genetic predisposition to having an iron overload disease. In some embodiments, the peptides are administered in a form of a pharmaceutical composition. In some embodiments, the peptides are administered in a therapeutically effective amount. As used herein, a "therapeutically effective amount" is an amount which ameliorates the symptoms and/or pathology of a given disease of iron metabolism as compared to a control such as a placebo.

A therapeutically effective amount may be readily determined by standard methods known in the art. The dosages to be administered can be determined by one of ordinary skill in the art depending on the clinical severity of the disease, the age and weight of the subject, or the exposure of the subject to iron. Preferred effective amounts of mini-hepcidins range from about 0.01 to about 10 mg/kg body weight, about 0.01 to about 3 mg/kg body weight, about 0.01 to about 2 mg/kg, about 0.01 to about 1 mg/kg, or about 0.01 to about 0.5 mg/kg body weight for parenteral formulations. Effective amounts for oral administration may be up to about 10-fold higher. Moreover, treatment of a subject with a peptide or composition of the present invention can include a single treatment or, preferably, can include a series of treatments. It will be appreciated that the actual dosages will vary according to the particular peptide or composition, the particular formulation, the mode of administration, and the particular site, host, and disease being treated. It will also be appreciated that the effective dosage used for treatment may increase or decrease over the course of a particular treatment. Optimal dosages for a given set of conditions may be ascertained by those skilled in the art using conventional dosage-determination tests in view of the experimental data for a given peptide or composition. Changes in dosage may result and become apparent by standard diagnostic assays known in the art. In some conditions chronic administration may be required.

The pharmaceutical compositions of the invention may be prepared in a unit-dosage form appropriate for the desired mode of administration. The compositions of the present invention may be administered for therapy by any suitable route including oral, rectal, nasal, topical (including buccal and sublingual), vaginal and parenteral (including subcutaneous, intramuscular, intravenous and intradermal). A variety of administration routes can be used in accordance with the present invention, including oral, topical, transdermal, nasal, pulmonary, transpercutaneous (wherein the skin has been broken either by mechanical or energy means), rectal, buccal, vaginal, via an implanted reservoir, or parenteral. Parenteral includes subcutaneous, intravenous, intramuscular, intraperitoneal, intra-articular, intra-synovial, intrasternal, intrathecal, intrahepatic, intralesional and intracranial injection or infusion techniques, as well as injectable materials (including polymers) for localized therapy. In some embodiments, the route of administration is subcutaneous. In some embodiments, the composition is in a sealed sterile glass vial. In some embodiments, the composition contains a preservative. Pharmaceutical compositions may be formulated as bulk powder, tablets, liquids, gels, lyophilized, and the like, and may be further processed for administration. See e.g. REMINGTON: THE SCIENCE AND PRACTICE OF PHARMACY.

20th ed. (2000) Lippincott Williams & Wilkins. Baltimore, Md., which is herein incorporated by reference.

It will be appreciated that the preferred route will vary with the condition and age of the recipient, the nature of the condition to be treated, and the chosen peptide and composition.

Pharmaceutical compositions of the present invention comprise a therapeutically effective amount of at least one peptide as disclosed herein, and a pharmaceutically acceptable carrier or diluent, which may be inert. As used herein the language "pharmaceutically acceptable carrier" is intended to include any and all solvents, dispersion media, bulking agent, coatings, antibacterial and antifungal agents, preservatives, isotonic and absorption delaying agents, and the like, compatible with pharmaceutical administration and known in the art. Except insofar as any conventional media or agent is incompatible with the active compound, use thereof in the compositions is contemplated.

Supplementary compounds can also be incorporated into the compositions. Supplementary compounds include niclosamide, liposomes, SL220 solubilization agent (NOF, Japan), Cremophor EL (Sigma), ethanol, and DMSO.

Toxicity and therapeutic efficacy of the peptides and compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Peptides which exhibit large therapeutic indices are preferred. While peptides that exhibit toxic side effects may be used, care should be taken to design a delivery system that targets such peptides to the site of affected tissue in order to minimize potential damage to uninfected cells and, thereby, reduce side effects.

The data obtained from the cell culture assays and animal studies can be used in formulating a range of dosage for use in humans. The dosage of peptides of the present invention lies preferably within a range of circulating concentrations that include the $ED_{50}$ with little or no toxicity. The dosage may vary within this range depending upon the dosage form employed and the route of administration utilized. For any peptide used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography or by mass spectroscopy.

Modified Mini-Hepcidin, PR65

Peptide Synthesis.

Figure 10A:
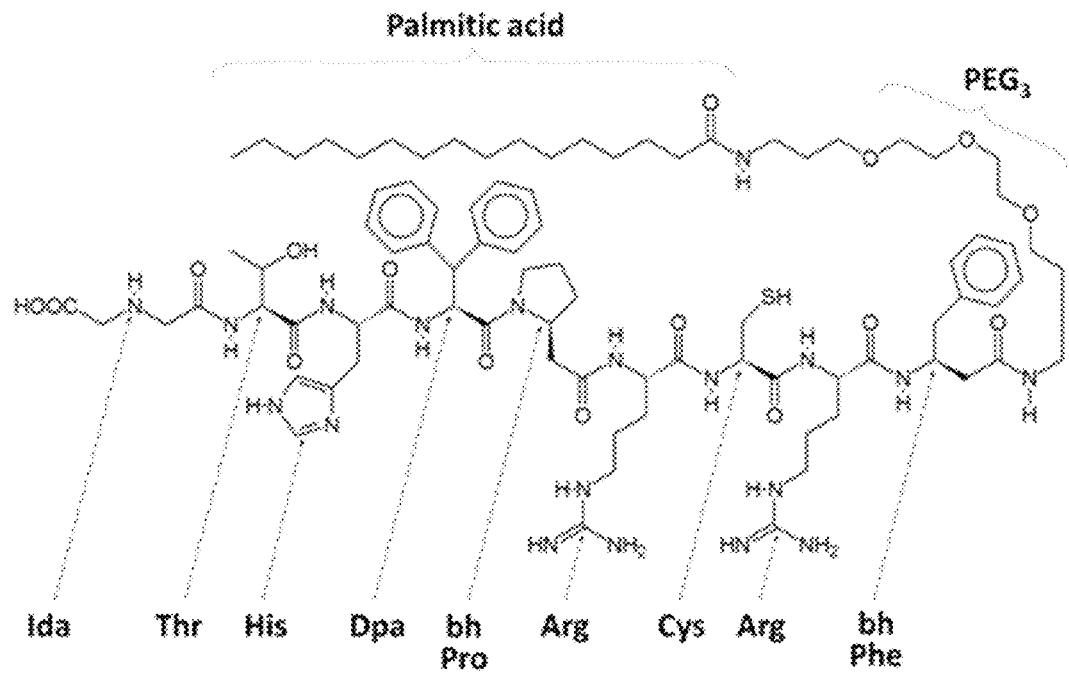
FIGS. 10A-10C show mini-hepcidin PR65 and its activity in wild-type mice.

Modified mini-hepcidins according to the present invention were synthesized using standard solid-phase fmoc chemistry and was purified by reverse-phase HPLC. For PR65, from A1 to A9 of Structural Formula IA (i.e. from the N to C terminus) the primary sequence was all L-amino acids as follows: iminodiacetic acid, threonine, histidine, diphenylalanine, beta-homo proline, arginine, cysteine, arginine and beta-homo phenylalanine. The C-terminal carboxy-amide was derivatized with a polyethylene glycol (PEG) linker and palmitic acid groups (FIG. 10A). Human hepcidin was purchased from Peptides International (Louisville, Ky.).

Animal Studies.

All studies were approved by the UCLA Office of Animal Research Oversight. Six weeks old male wild-type C57BL/6 mice were used to compare the activities of native hepcidin and PR65, and to test the effect of PR65 after intraperitoneal versus subcutaneous route of administration. Hepcidin and PR65 were administered in 100 µl of SL220, a PEG-phospholipid based solubilizer (NOF Corporation, Japan) (Preza G C, et al. (2011) J Clin. Invest. 121(12):4880-4888) and iron parameters were measured after 4 hours. This solvent does not significantly change serum iron concentrations in mice (<5 µM change, data not shown).

The therapeutic effects of PR65 was studied in hepcidin-1 knockout mice ($Hamp1^{-/-}$) (Lesbordes-Brion J C, et al. (2006) Blood 108(4):1402-1405) and backcrossed onto the C57BL/6 background (N4, 99% gene marker identity) using marker-assisted accelerated backcrossing (Charles River Laboratories, Wilmington, Mass.). PR65 was administered subcutaneously in 100 µl of SL220 solubilizer. Short-term studies were carried out for up to 48 hours to establish the effectiveness of a single injection. Long-term studies ("prevention" and "treatment") were carried out for 2 weeks using daily injections and iron and hematological parameters measured 24 hours after the last injection.

To test the ability of PR65 to prevent, inhibit, or reduce iron loading ("prevention" studies), male $Hamp1^{-/-}$ mice were iron-depleted by placing them on a low-iron diet (4 ppm iron) for 2 months starting at the age of 5-6 weeks. The regimen was developed to match the hepatic iron content of wild-type C57B6 mice, about 2-3 µmoles/g wet liver (Ramos E, et al. (2011) Hepatology 53(4):1333-1341). A group of mice was analyzed immediately after iron depletion (baseline group), and the remaining animals were switched to an iron-loading diet (standard chow, about 300 ppm Fe) and received daily subcutaneous injection of solvent or PR65 (20, 50 or 100 nmoles) for 2 weeks. All mouse diets were obtained from Harlan-Teklad (Madison, Wis.).

To test the effect of PR65 on iron-loaded $Hamp1^{-/-}$ mice ("treatment" studies), male mice were kept on the standard diet for their entire lifespan. Beginning at 12-14 weeks of age, 50 nmoles of PR65 or solvent was injected daily by the subcutaneous route for 2 weeks.

Measurement of Iron and Hematological Parameters.

Serum iron and non-heme iron concentrations were determined as previously described (Ramos E, et al. (2011) Hepatology 53(4):1333-1341), using acid treatment followed by a colorimetric assay for iron quantitation (Genzyme, Cambridge, Mass.). Deparaffinized sections were stained with the Perls Prussian blue stain for non-heme iron, enhanced with the SG peroxidase substrate kit (Vector Labs, Burlingame, Calif.) and counterstained with nuclear fast red. Complete blood counts were obtained with a HemaVet blood analyzer (Drew Scientific, Oxford, Conn.).

Statistical Analysis.

The statistical significance of differences between group means was evaluated using Student T-test and the Sigmaplot 11.0 package (Systat Software, San Jose, Calif.).

Mini-Hepcidin Treatment Regimen

Figure 10B:
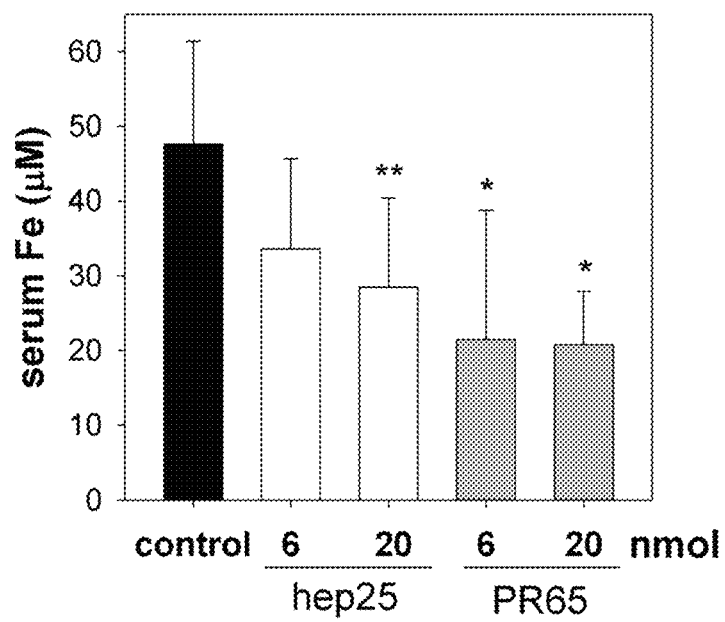
Figure 10C:
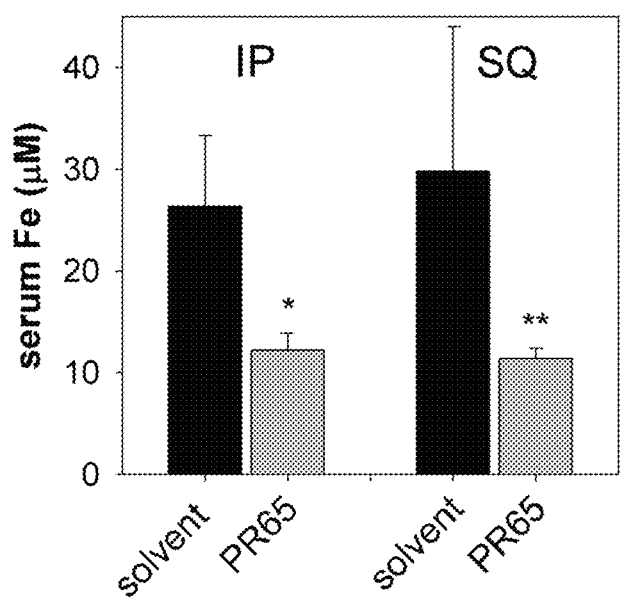

PR65 (FIG. 10A) was selected for the prevention and treatment studies in hepcidin-null mice based on pilot studies in wild-type C57BL/6 mice. PR65 was found to be among the most potent mini-hepcidins and its molar bioactivity after intraperitoneal injection was comparable to that of native hepcidin (FIG. 10B). Moreover, PR65 retained full activity with subcutaneous as compared to intraperitoneal administration (FIG. 10C) and its cost of synthesis was favorable compared to other mini-hepcidins. Based on qualitative assessment of more than 80 mini-hepcidins, the high bioactivity of PR65 compared to the prototypical peptide containing the 9 N-terminal amino acids of human hepcidin (SEQ ID NO:9) is likely due to increased aromaticity, solubility, resistance to proteolysis, as well as lower renal clearance due to increased plasma protein binding mediated by the palmitoyl group.

Figure 11A:
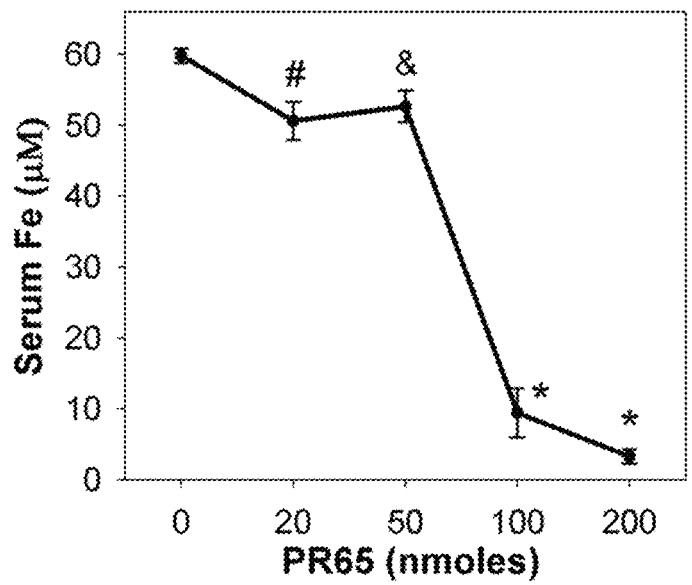
FIGS. 11A and 11B show the hypoferremic effect of PR65 in iron-loaded hepcidin knockout mice.
Figure 11B:
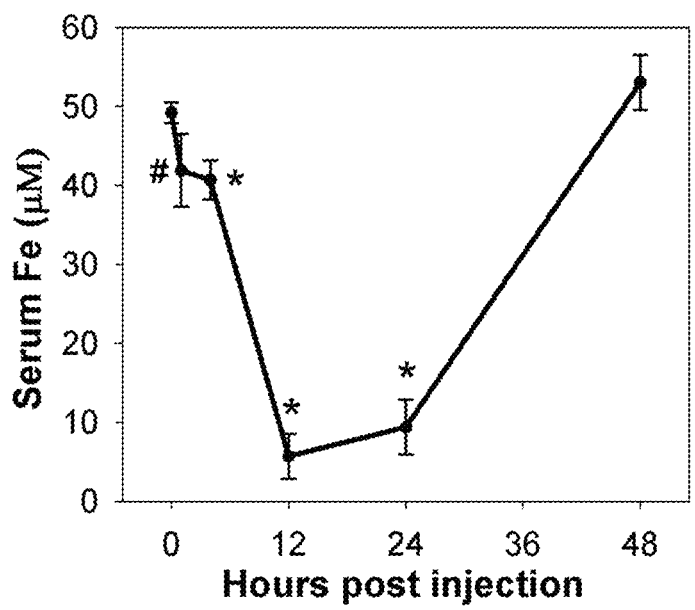

To establish optimal dosing parameters for a long-term mini-hepcidin treatment regimen, dose-response (FIG. 11A) and time course (FIG. 11B) experiments in iron-loaded hepcidin knockout mice, Hamp1−/− mice, was performed. After 24 hours, subcutaneous injection of 20 and 50 nmoles of PR65 caused 15% and 10% (p=0.005, p=0.004) decreases in serum iron, while 100 and 200 nmole doses resulted in an 85% and 95% reduction ($p<0.001$ for both). Because 100 nmoles of PR65 produced a near maximal hypoferremia, this dose was selected for a time course experiment to determine the timing and duration of its peak effect. The maximal drop (88%) in serum Fe occurred 12 hours after subcutaneous injection ($p<0.001$), and serum Fe remained severely suppressed (82%) at 24 hours but returned to solvent control levels 48 hours after injection.

Figure 12:
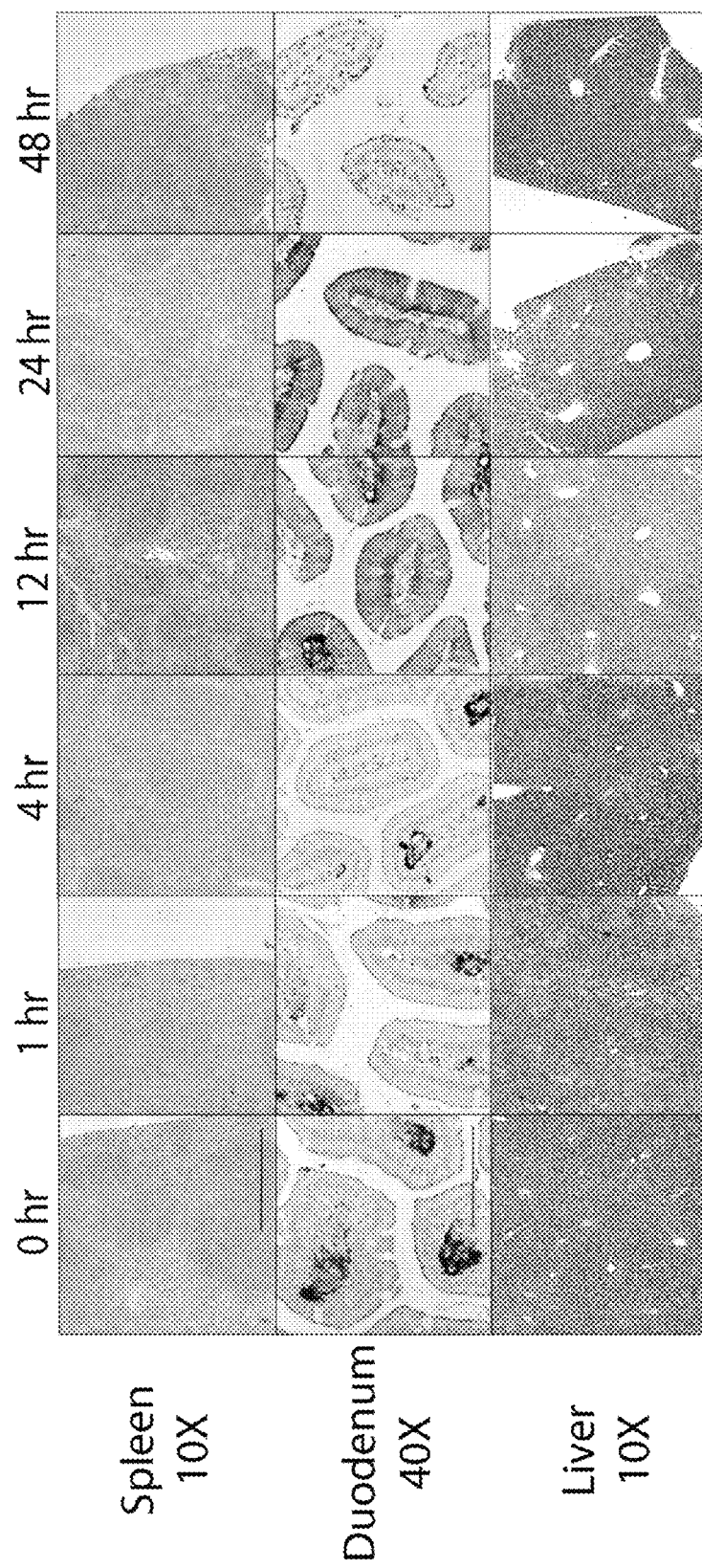
FIG. 12 shows the changes in iron distribution in PR65-treated hepcidin knockout mice. Tissue iron was visualized by enhanced Perls stain at 0-48 hours after subcutaneous injection of PR65 (100 nmoles). Representative images are shown. Horizontal bars indicate 400 µm (10×) and 100 µm (40×). Top row: Spleen iron was scant and its distribution did not change appreciably during the 48 hours. Middle row: Iron in the villus stroma was evident in solvent-treated and 1-4 hour PR65-treated mice, indicating active ferroportin-mediated efflux of iron from basolateral membranes of enterocytes. From 12-24 hours, iron was retained in enterocytes consistent with (mini)hepcidin-induced ferroportin degradation. 48 hours after injection iron was no longer retained by enterocytes. Bottom row: As expected, the livers were iron-loaded at baseline and no changes in the pattern of iron staining were seen within 48 hours of PR65 treatment.

The activity of PR65 (100 nmoles) was also assessed over 48 hours through its effect on tissue iron retention. Interestingly, spleen iron accumulation was not observed during 48 hours after PR65 injection (FIG. 12). This is likely because the spleen in hepcidin knockout mice is completely depleted of iron and it takes more than 2 days to accumulate enough iron so it is conclusively detectable by enhanced Perls stain. Liver iron content, which was already high in these mice, did not visibly change through the course of the experiment. From 1-4 hours after injection, duodenal sections showed distinct iron staining around villous capillary networks indicating continued high ferroportin activity and uncurbed iron transfer to plasma. From 12-24 hours after PR65 injection, iron accumulated within enterocytes consistent with the expected mini-hepcidin-induced loss of ferroportin and diminished iron transfer to plasma. As the mini-hepcidin effect wore off 48 hours after injection, iron was no longer retained in enterocytes.

Thus, in some embodiments, subjects are treated with a given does, e.g. about 100 μg/kg, of a mini-hepcidin daily, and after about one week, the dose is halved if the subject's serum iron concentration is below about 10 μM or doubled if serum iron is above about 30 μM. At about the beginning of the third week of treatment, the dose may be increased or decreased by about 25-50% to maintain serum iron levels between about 10-30 μM. In some embodiments, after about 1 week of administration of one or more mini-hepcidins, the iron levels, and/or ferroportin, and/or mini-hepcidin levels in the subject may be monitored using methods known in the art or as disclosed herein, and then based on the levels, the subject may be treated accordingly, e.g. administered one or more subsequent doses of one or more mini-hepcidins which may be higher or lower than the initial dose. The mini-hepcidins of the subsequent doses may be the same or different from the mini-hepcidins of the first dose.

Chronic Administration of Mini-Hepcidin Prevents Iron Loading in Hepcidin Deficient Subjects The ability of PR65 to prevent iron loading in hepcidin in subjects was examined using mice as models. Hepcidin KO mice were placed on an iron-deficient diet for 8 weeks to lower their iron stores to a level comparable to that of WT mice. After iron depletion, a group of mice was analyzed to establish the baseline iron and hematological parameters and the rest of the mice were placed on an iron-loading diet (300 ppm Fe) for 2 weeks while simultaneously receiving daily subcutaneous injections of solven only (control) or PR65 (20, 50 or 100 nmoles) in solvent. It was hypothesized that in comparison to the solvent treatment, PR65 would cause iron retention in the spleen, decrease serum iron and prevent liver iron loading. Because cardiac iron overload is a marker for poor prognosis in iron-loaded patients, heart iron was also measured. Hemoglobin concentrations were monitored to detect potential iron-restrictive effects of hepcidin excess on erythropoiesis.

Figure 13A:
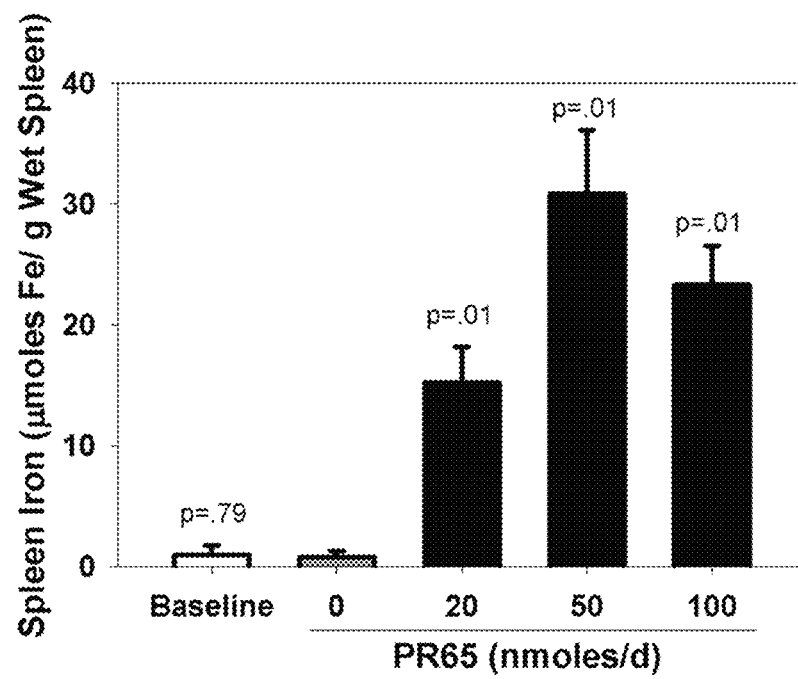
Figure 13B:
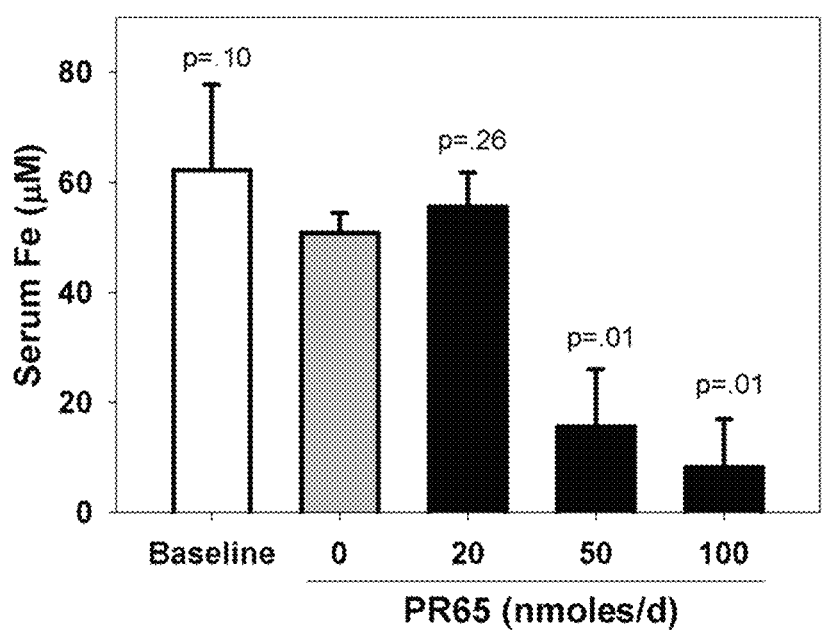
Figure 13C:
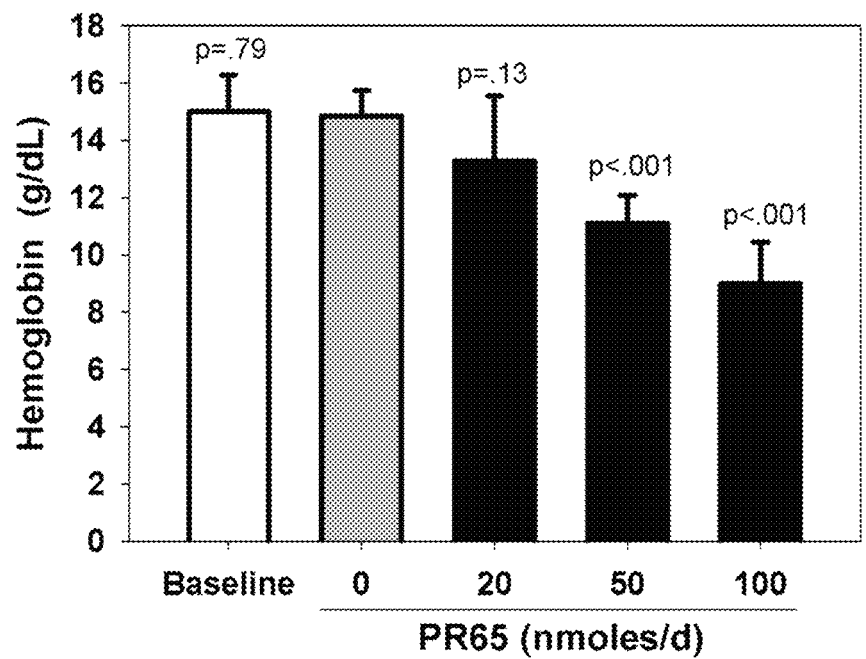
Figure 13D:
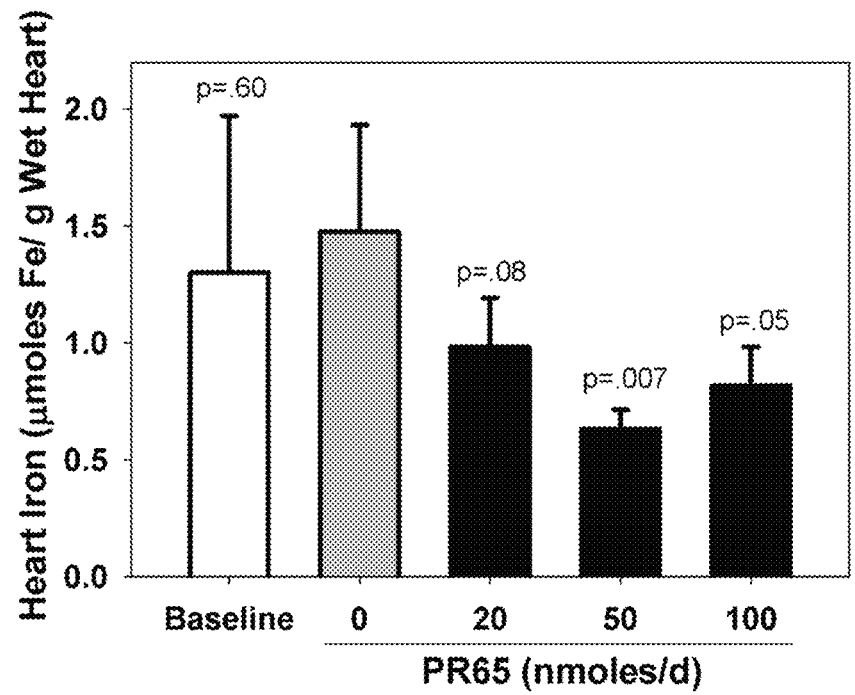
Figure 13E:
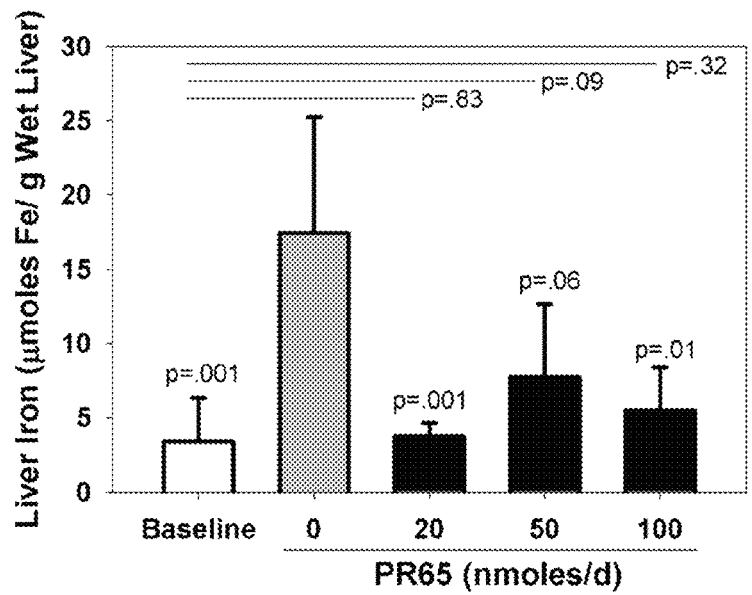

Hepcidin agonist activity of the mini-hepcidins was confirmed in all treated groups by the increased retention of iron in macrophages manifested as increases in spleen iron content. Compared to the almost undetectable non-heme iron content in solvent-injected control spleens, all three mini-hepcidin doses caused 15- to 30-fold increases in spleen iron content (p=0.01 for all) (FIG. 13A). Serum iron did not change in mice that received 20 nmoles of PR65 daily (p=0.26), but decreased by 69% and 83% in mice that received 50 and 100 nmoles per day (p=0.01 for both) (FIG. 13B). The decrease in circulating iron concentrations was also reflected as dose-dependent 3 and 5 g/dL reductions of hemoglobin concentrations in the 50 and 100 nmoles groups, respectively ($p<0.001$ for both), but hemoglobin levels did not change significantly at 20 nmoles (p=0.13) (FIG. 13C). Heart iron concentration dropped 33%, 60% and 47% in mice treated with 20, 50 and 100 nmoles of PR65 respectively (p=0.08, 0.007, 0.05) (FIG. 13D). Additionally, mice treated with the three PR65 doses had 76%, 53% and 68% less liver iron than solvent-treated controls (p=0.001, 0.06, 0.01) and no statistically significant increases in liver iron compared to mice from the iron-depleted baseline group. Except for serum iron and hemoglobin, the lack of a consistent dose-response relationship may indicate that the maximum effect was reached at a relatively low dose so that the differences reflect statistical fluctuations (liver and heart iron) or that two or more effects of PR65 interact in a complex manner (splenic iron may reflect the combined effects of decreased iron export from the spleen, decreased iron absorption in the duodenum, and decreased number of erythrocytes all of which are expected effects of PR65).

Figure 14:
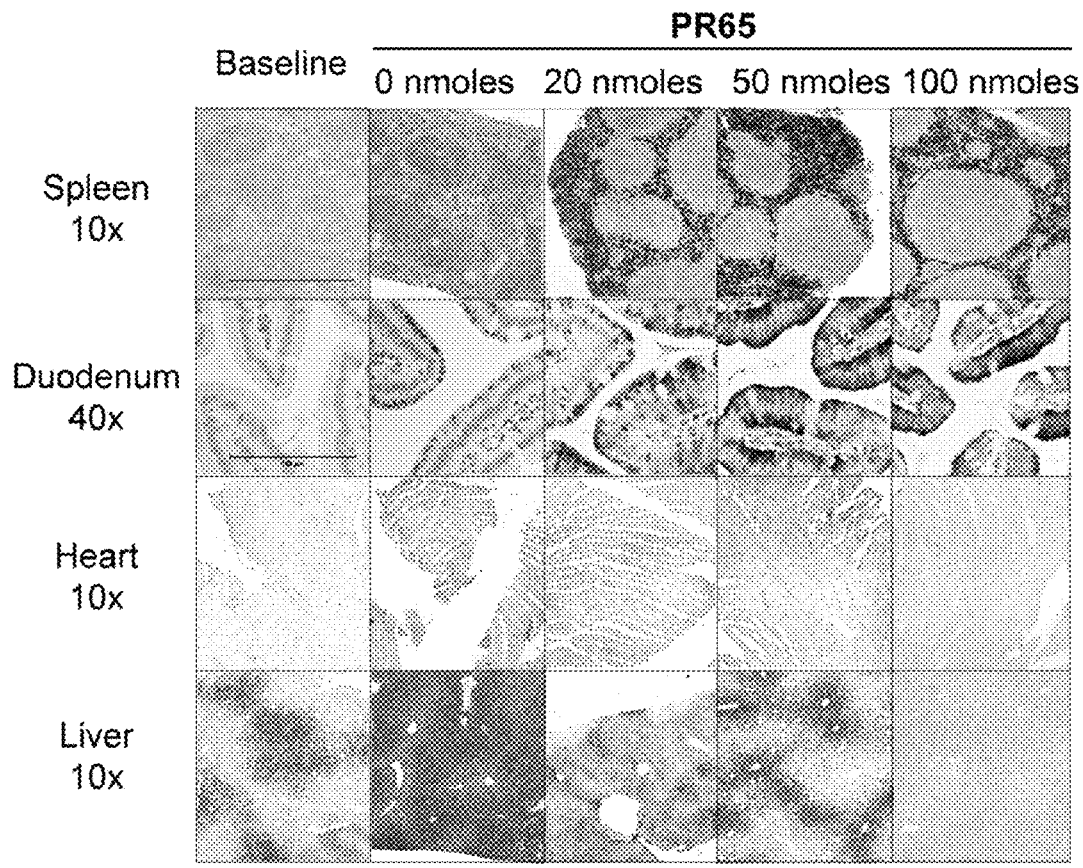
FIG. 14 shows the cellular distribution of iron after 2 weeks of PR65 injections for the prevention of iron overload. Representative images are shown. Horizontal bars indicate 400 µm (10×) and 100 µm (40×). Iron accumulation was seen in the splenic red pulp of PR65-treated mice but not solvent-treated mice. Similarly, iron accumulation in duodenal enterocytes was seen only in PR65-treated mice. Compared to heart iron staining of solvent-injected mice, there was less iron accumulation in the heart of animals injected with 50 and 100 nmoles of PR65, consistent with the quantitative method in FIG. 4. Liver iron loading in mice treated with 20 and 50 nmoles of PR65 was similar to that of the baseline group and much less than the iron loading in the solvent-treated group. At the highest PR65 dose, liver iron was lower than at baseline indicating that mice were able to mobilize liver iron despite high mini-hepcidin activity.

Perls stains of organ sections from mini-hepcidin-treated mice compared to iron-depleted baseline mice indicated that iron stores in the liver did not increase from baseline in the 20 and 50 nmoles groups, and were even lower than baseline at the 100 nmole dose (FIG. 14). In contrast, liver sections of the solvent-injected mice showed very high iron levels. A similar pattern of differences between the solvent and PR65 groups was observed in the heart, with a complete lack of iron staining in the heart of mice that received 100 nmoles of peptide. Significant accumulation of iron in the red pulp of the spleen was observed in all mini-hepcidin groups, but not in mice that received solvent, or in baseline iron-depleted mice. Duodenal sections at baseline showed no iron staining, while PR65-treated mice showed iron retention in the duodenal enterocytes, again confirming that PR65 blocked iron efflux from enterocytes.

Thus, in some embodiments, the present invention provides methods of preventing iron loading in subjects having abnormally low or no levels of hepcidin which comprises chronic administration of one or more mini-hepcidins according to the present invention.

Mini-Hepcidin Effect in Iron Overloaded Hepcidin Knockout Mice

Figure 15A:
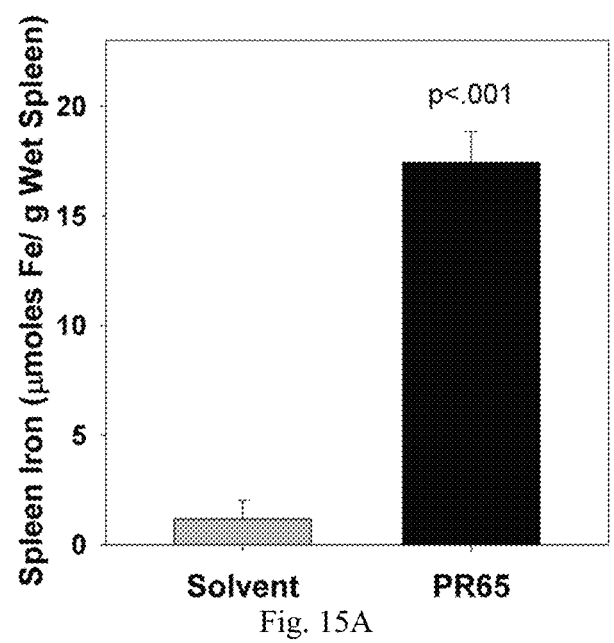
FIGS. 15A-15E shows that two-week PR65 treatment of iron-loaded hepcidin knockout mice caused modest redistribution of iron. Hepcidin knockout mice were kept on a 300 ppm iron diet for their entire lifespan. Starting at 12 weeks of age, one group of mice was injected subcutaneously with solvent (n=4) and the other with 50 nmoles of PR65 (n=4) daily for 2 weeks. Iron and hematological parameters were measured 24 hours after the last injection. In PR65-treated mice compared to solvent-treated mice.
Figure 15B:
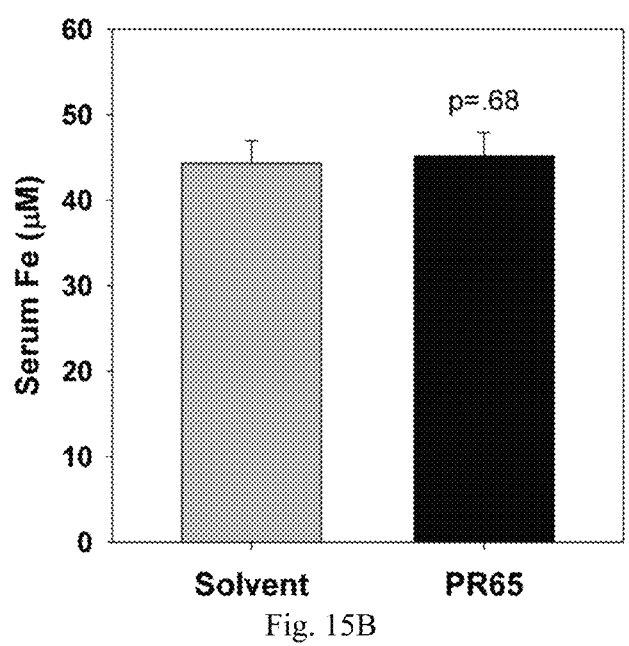
Figure 15C:
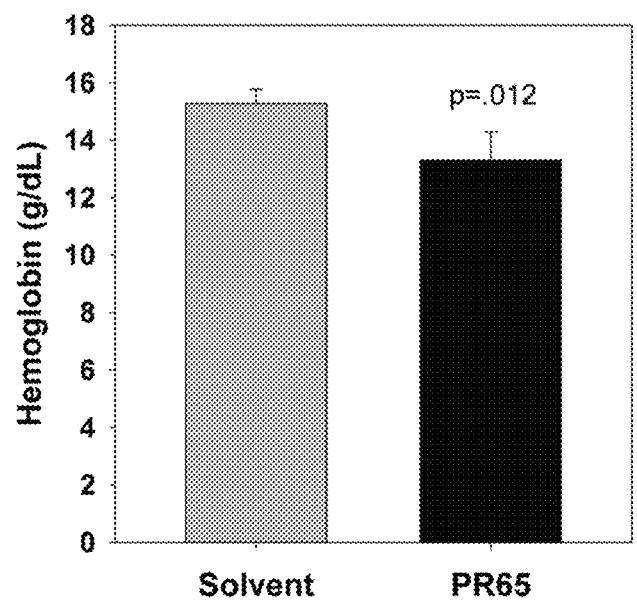
Figure 15D:
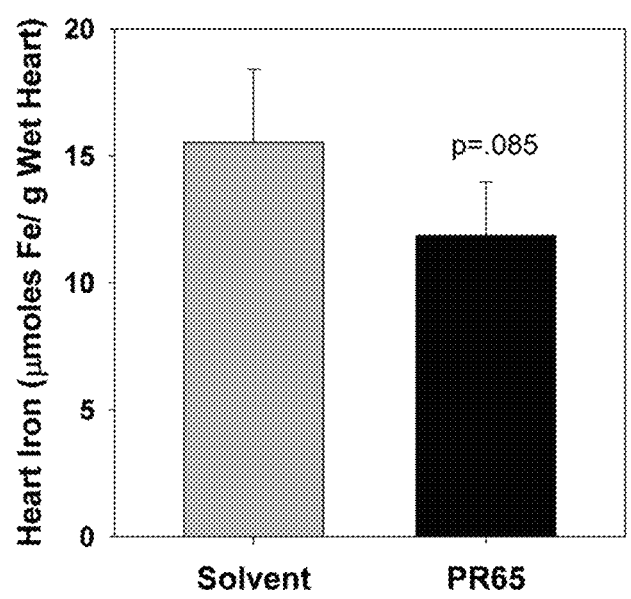
Figure 15E:
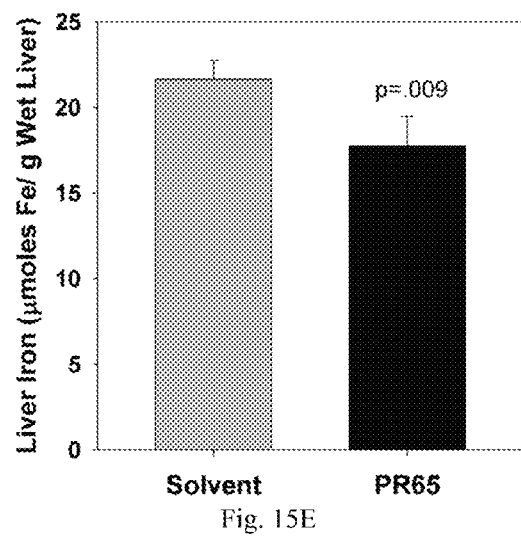

To assess the potential of mini-hepcidins as a standalone treatment for iron overload in subjects, 12 week old iron-overloaded hepcidin knockout mice were injected with 50 nmoles of PR65 daily for 14 days. This dose was chosen as the maximal tolerated dose because mice that received 100 nmoles in the previous experiment became moderately anemic. Peptide activity was confirmed by the 15-fold increase in spleen iron content (p<0.001) (FIG. 15A). In contrast to mice that were iron-depleted before PR65 administration, in mice with established iron overload serum iron levels were not decreased 24 hours after the last dose compared to solvent-treated mice (p=0.682) (FIG. 15B). However, the 2 g/dL decrease in hemoglobin (p=0.012) (FIG. 15C) suggests that serum iron could have been transiently decreased during the treatment. The less than 24 hours duration of the hypoferremic effect of each 50 nmoles dose may have been due to the severe iron overload of the hepcidin knockout mice at this age. Accumulated hepatocyte iron could stimulate ferroportin synthesis and iron efflux from hepatocytes into plasma by relieving the inhibition of ferroportin translation by iron-regulatory proteins (IRPs) interacting with 5' iron-regulatory element (5' IRE) in the ferroportin mRNA, and possibly by other mechanisms. Compared to the control group, iron-loaded mice treated with PR65 showed a trend toward decreased heart iron concentrations (24% decrease, p=0.085) (FIG. 15D), and their liver iron levels decreased by about 20% (p=0.009) or about 200 µg/g (FIG. 15E), an amount equivalent to the total hepatic iron content in wild-type mice.

Figure 16:
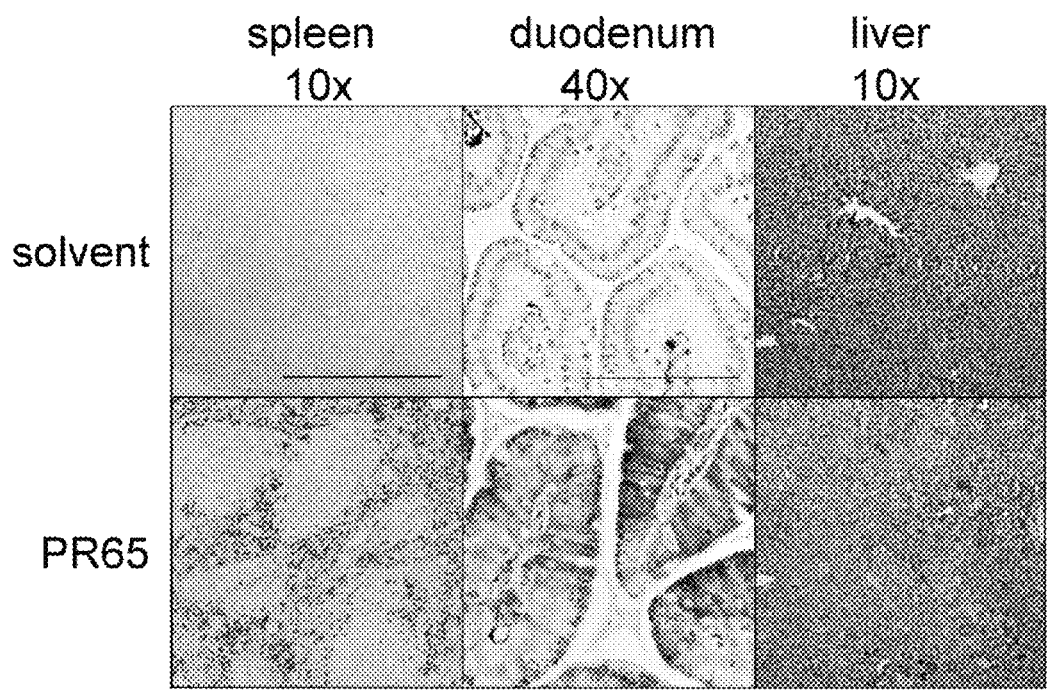
FIG. 16 shows the cellular distribution of iron after 2 weeks of PR65 injections for the treatment of established iron overload. Tissue sections correspond to the animals analyzed in FIGS. 15A-15E, with representative images shown. Horizontal bars indicate 400 μm (10×) and 100 μm (40×). Enhanced Perls stain confirmed that splenic macrophages and duodenal enterocytes retained iron in PR65-treated but not in solvent-treated mice. Compared to solvent-treated controls, less intense iron staining was observed in the liver of mice treated with PR65. No consistent differences between solvent- and PR65-treated mice were seen in sections of the heart (not shown).
Figure 17:
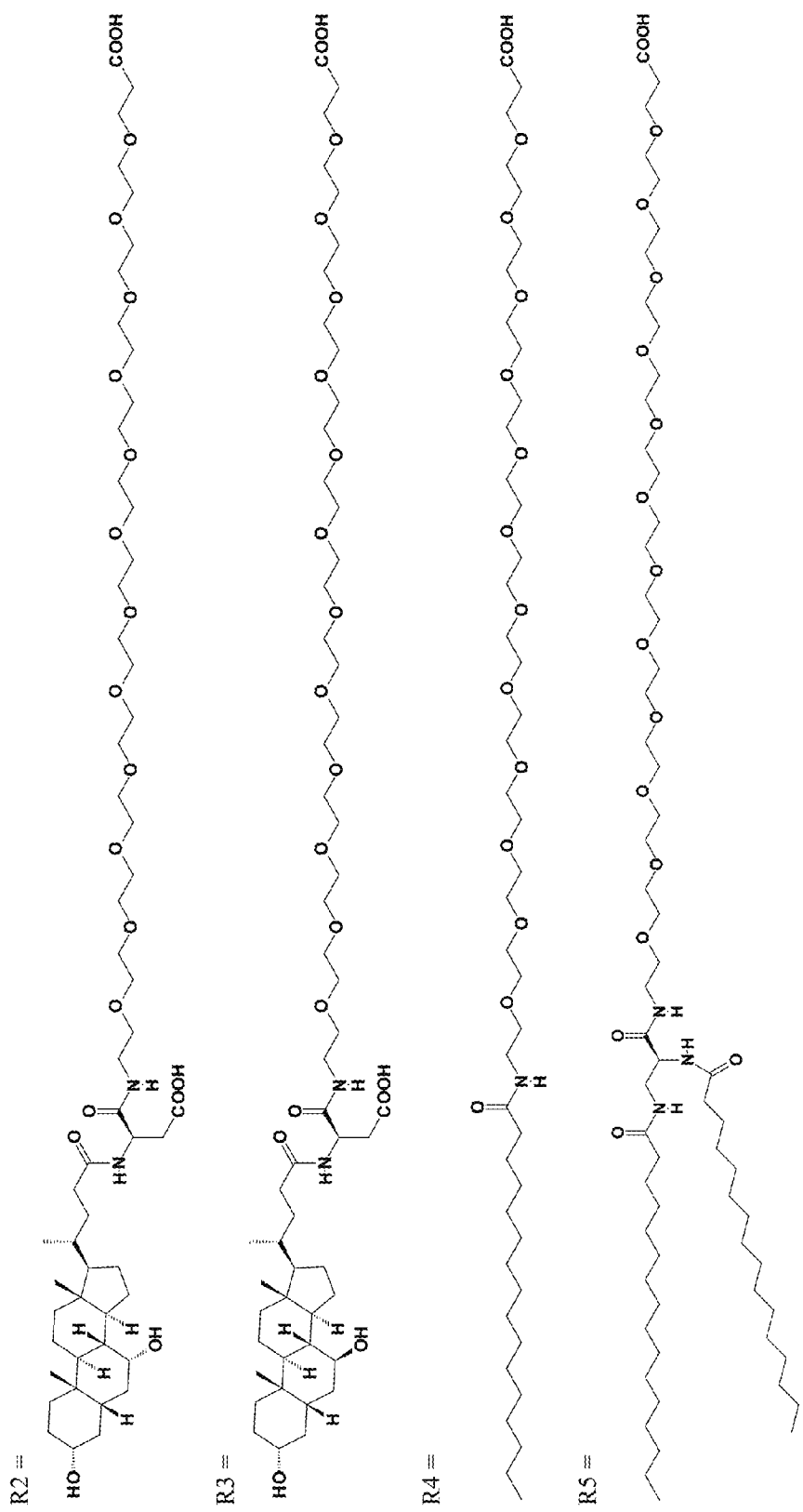
FIG. 17 shows some of the structures of the molecules recited in Tables 1, 3 and 4.
Figure 17:
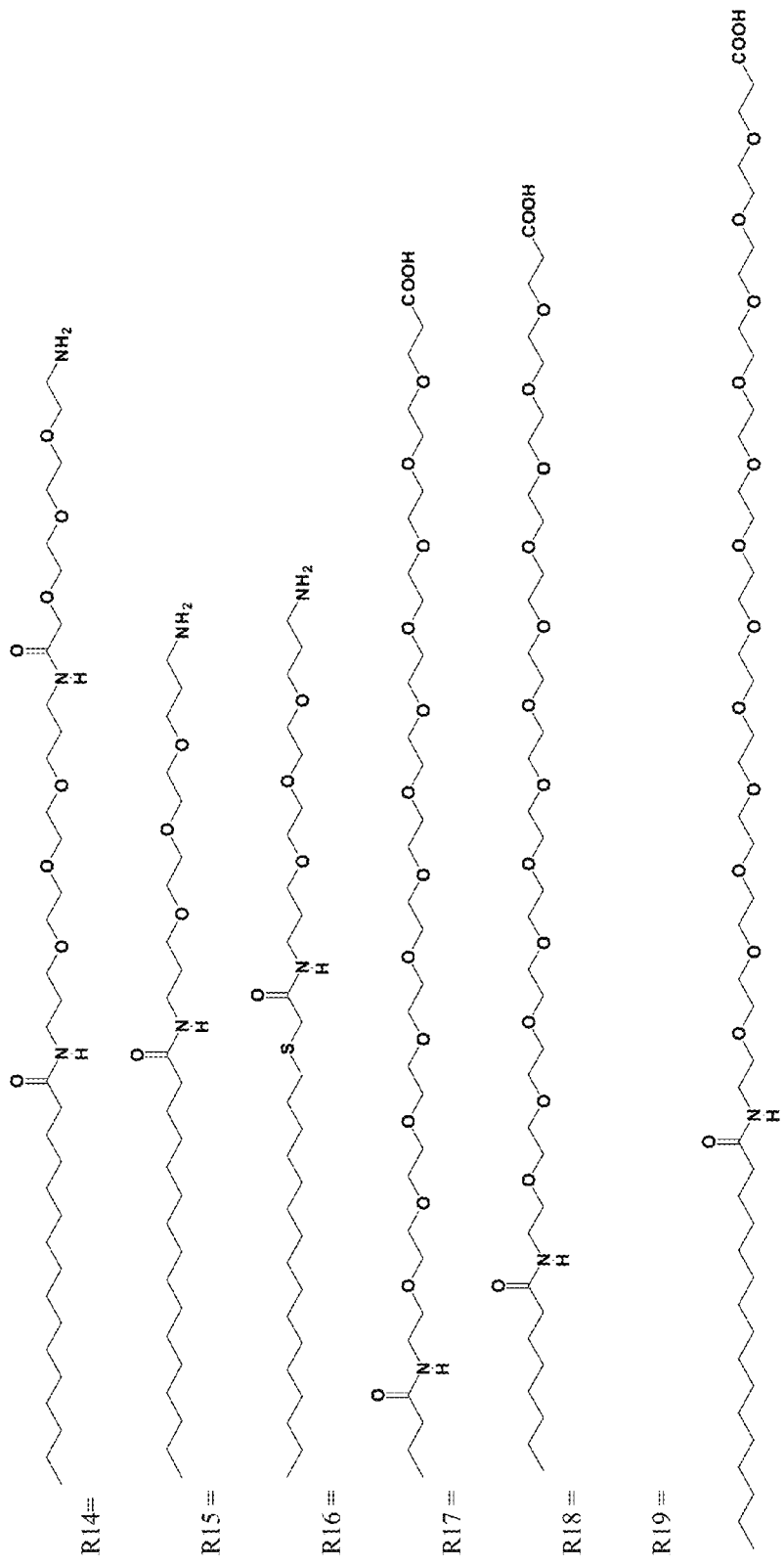
Figure 17:
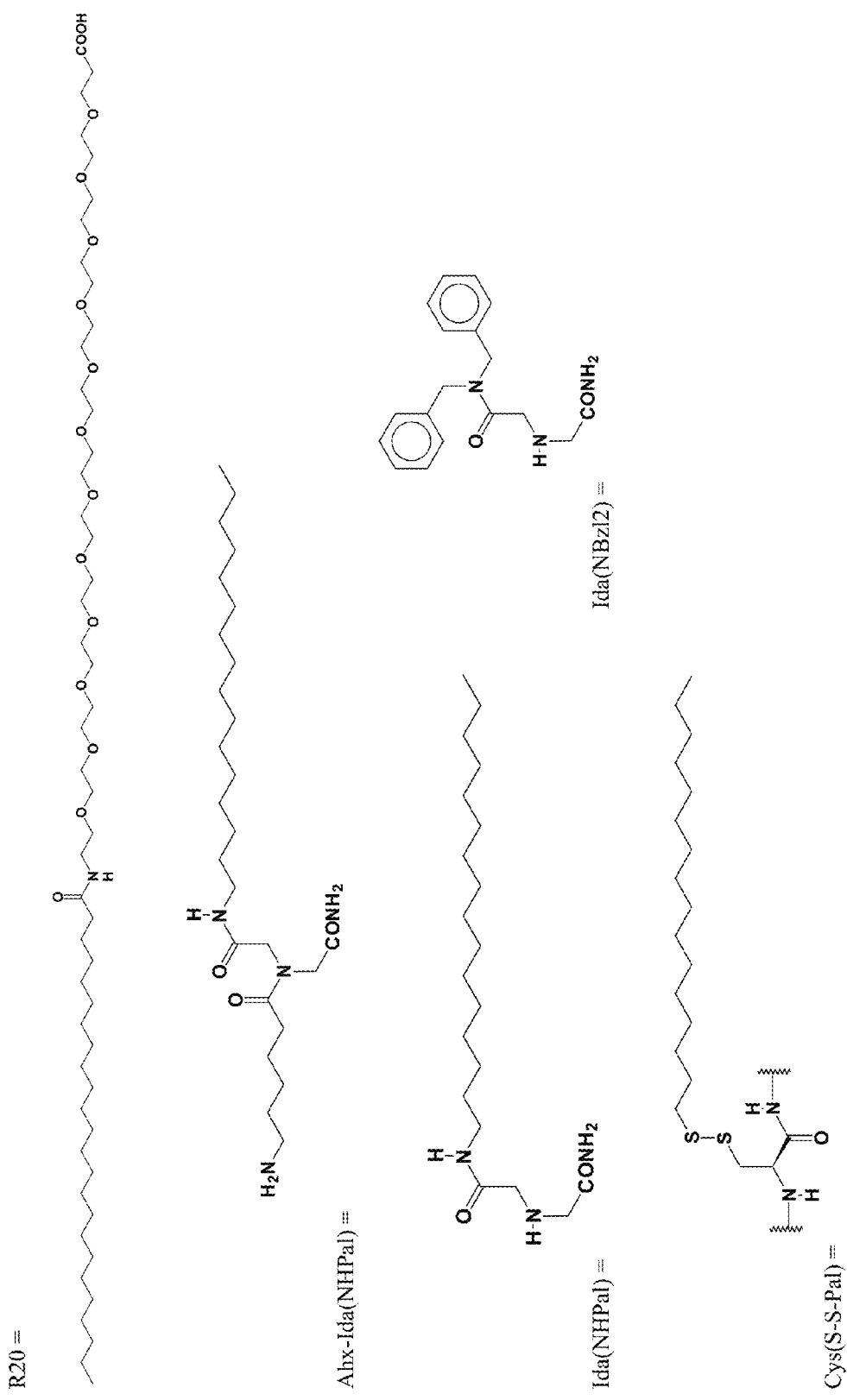
Figure 17:
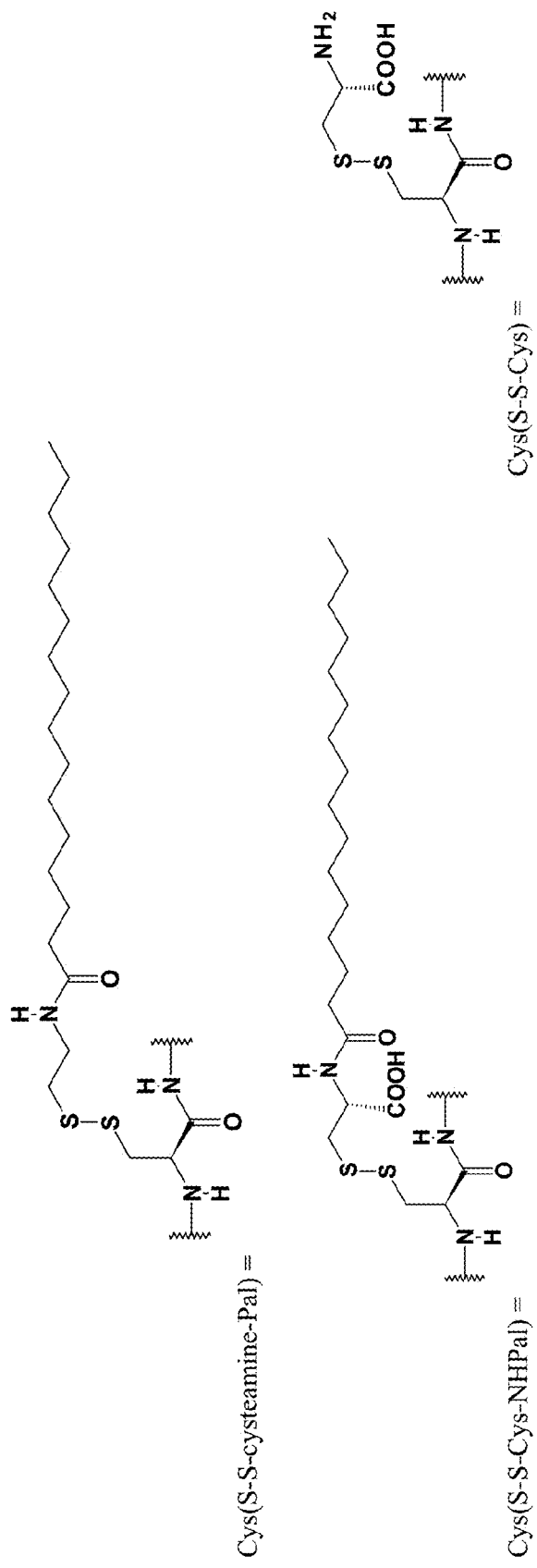

Enhanced Perls staining demonstrated iron retention in the spleen and duodenum in mice treated with PR65 and a change in the iron distribution pattern in the liver (FIG. 16). No statistically significant differences were noticeable in the heart and pancreas sections of the solvent and PR65-treated mice. In the aggregate, staining and quantitative analysis indicate that the 2-week mini-hepcidin treatment alone could not only inhibit dietary iron absorption but also redistribute a modest amount of iron from the liver to the spleen.

Thus, in some embodiments, human subjects being treated for an iron overload disease are treated with one or more mini-hepcidins for a period of at least the minimum period necessary to detect that the treatment prevented liver iron accumulation by available imaging technologies (e.g. FerriScan), e.g. about three months. In some subjects, the treatment may be continued for many years or for the life of the subject.

As shown in FIG. 13, PR65 acted predominantly by reducing iron absorption but also redistributed iron into splenic macrophages when administered prophylactically. Thus, in some embodiments, one or more mini-hepcidins may be administered to a subject as a prophylactic treatment against iron overload in the subject. For example, where a subject having liver iron that is within a normal range, but has a predisposition for an iron overload disease (e.g. genetically predisposed to excessive iron adsorption), or is at risk of developing an abnormally high level of iron, the subject may be administered one or more mini-hepcidins to prevent and/or reduce the likelihood that the subject will develop an iron overload disease and/or abnormally high levels of iron.

According to FIG. 13, iron distribution was calculated based on the following assumptions and equations: Estimated organ masses based on average weight of 25 g, Blood volume (5.5%)=1.4 ml, Liver mass (5%)=1.3 g, Spleen mass (0.3%)=0.08 g, % Fe in Hb=0.34% based on the molecular mass of Hb=64,000 Dalton and 4 iron atoms with a total atomic mass of 224 Dalton, Total iron in Hb=(Hb concentration)×(Blood volume)×(% Fe in Hb), and Total iron in an organ=molar iron concentration×organ mass×56 g/mole. The amounts for the solvent group and the PR65 group are shown as follows:

TABLE 5

| | Total organ iron (mg) |
|---|---|
| Solvent treatment | |
| Hb = 15 g/dl | 0.7 |
| Liver iron concentration = 17 µmoles/g | 1.2 |
| Spleen iron concentration = 0.5 µmoles/g | 0.002 |
| Total | 1.9 |
| PR65: 50 nmoles | |
| Hemoglobin = 11.5 g/dl | 0.5 |
| Liver iron concentration = 8 µmoles/g | 0.6 |
| Spleen iron concentration = 30 µmoles/g | 0.1 |
| Total | 1.2 (36% decrease) |

The resulting decrease of plasma iron could also reduce the levels of toxic non-transferrin bound iron (NTBI) and promote the mobilization of iron from the heart and endocrine organs where iron excess is not tolerated. Thus, in some embodiments, one or more mini-hepcidins may be administered to a subject in order to reduce the levels of NTBI and/or promote the mobilization of iron from the heart and endocrine organs to other organs and tissues.

Unlike phlebotomy or chelation, mini-hepcidins would not be expected to appreciably increase iron losses from the body. In a relatively mild model of iron overload in HFE null mice (Viatte L, et al. (2006) Blood 107(7):2952-2958), transgenic hepcidin expression was reported to cause significant redistribution of iron into hepatic macrophages, a location where iron accumulation is relatively nontoxic. In more overloaded Hamp1$^{-/-}$ mice, red pulp macrophages in mini-hepcidin-treated mice retained iron but the small resulting decrease in liver and heart iron stores suggests that mini-hepcidins alone confer a modest therapeutic benefit once the liver iron burden is high. The shorter than 24 hour effect of a mini-hepcidin dose on transferrin saturation in this severe iron overload model may imply that NTBI continues to deliver iron to parenchymal organs counteracting the effects of iron redistribution to macrophages and decreased iron absorption.

Therefore, in established iron overload in human subjects, effective treatment with one or more mini-hepcidins may include more than one dose per day, a prolonged treatment period before a beneficial effect in liver iron can be detected, or may be combined with removal of iron by phlebotomy or chelation.

Dosages

The exclusive use of L-amino acids in PR65 was found to significantly reduce peptide production costs. In addition, the unnatural and highly aromatic residues in PR65 were unexpectedly found to substantially reduce the minimal effective dose in mice to 20 nmoles/d or 1.3 mg/kg/d.

According to U.S. Food and Drug Administration dosing adjustment guidelines, the difference in metabolic rates between the mouse and human requires a conversion based on the Km factor which normalizes doses to body surface area (Reagan-Shaw S, et al. (2008) FASEB J 22(3):659-661). A human equivalent dose (HED) can be estimated by HED=animal dose (mg/kg)×(animal Km/human Km), where the Km for mouse and an adult human are 3 and 37, respectively. Thus, according to the present invention, a subcutaneous dose of mini-hepcidin in a human could be up to about 50-100 µg/kg/d, about 75-125 µg/kg/d, or about 90-110 µg/kg/d, preferably about 100 µg/kg/d (as this dose is a readily administrable amount of peptide about three times the median basal dose of the most widely used peptide drug, subcutaneous insulin, commonly used at 0.75 U/kg/d or 33 µg/kg/d in type 2 diabetics (Rosenstock J, et al. (2001) Diabetes Care 24(4):631-636)). Of course, lower doses, as well as higher doses, depending on the particular mini-hepcidin, form of administration, formulation, the subject and the degree of iron overload, may be administered to subject.

Important differences between murine and human iron metabolism that could alter the effect of a mini-hepcidin, e.g. PR65, in humans include the somewhat longer lifetime of human erythrocytes (120 days vs 40 days) and the much lower fractional iron losses in humans (daily iron losses compared to total body iron) as estimated from the slower depletion of iron stores on iron-deficient diets (in males: 300-600 days vs 15-20 days). The net effect of these differences is the much lower contribution of intestinal iron absorption to the daily iron flux in humans (4-8% compared to more than 50% in mice) (Ramos E, et al. (2011) Hepatology 53(4):1333-1341). If hepcidin and its analogs exert stronger effects on macrophages than on enterocytes (Reagan-Shaw S, et al. (2008) FASEB J 22(3):659-661) this could further decrease the relative doses of mini-hepcidins required for a similar hypoferremic effect in humans. Thus, in some embodiments, a therapeutically effective dose of one or more mini-hepcidins ranges from about 10-500 µg/kg/d. Again, lower doses, as well as higher doses, depending on the particular mini-hepcidin, form of administration, formulation, the subject and the degree of iron overload, may be administered to subject.

As provided herein, mini-hepcidins according to the present invention may be used to inhibit, reduce, or treat iron overload in subjects at risk due to genetic defects or those who have already undergone iron depletion, but no longer tolerate chelation or venesection therapy. The mini-hepcidins according to the present invention may be used to treat a subject having β-thalassemia major and/or a subject having hepcidin levels that are higher than normal but are lower than what is appropriate for the degree of iron overload and the particular subject. For example, one or more min-hepcidins according to the present invention may be used to treat a subject who suffers from hyperabsorption of dietary iron, but has normal levels of iron, in order to lower the amount of iron in the subject and offset the hyperabsorption. One or more mini-hepcidins according to the present invention may be used to treat ineffective erythropoiesis and improve anemia in subjects.

Because of the relatively small size of the mini-hepcidins of the present invention, the mini-hepcidins may be appropriately formulated and optimized for oral administration or administration by other noninvasive means such as those used for insulin administration (Roach P. (2008) Clinical Pharmacokinetics 47(9):595-610) such as inhalation, or transcutaneous delivery, or mucosal nasal or buccal delivery.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. An isolated peptide having the following structural formula IA or IB

A1-A2-A3-A4-A5-A6-A7-A8-A9-A10    IA

A10-A9-A8-A7-A6-A5-A4-A3-A2-A1    IB wherein

A1 is Asp, D-Asp, Glu, D-Glu, pyroglutamate, D-pyroglutamate, Gln, D-Gln, Asn, D-Asn, bhAsp, Ida, Ida(NHPal), or N-MeAsp;

A2 is Thr, D-Thr, Ser, D-Ser, Val, D-Val, Ile, D-Ile, Ala, D-Ala, Tle, Inp, Chg, bhThr, or N-MeThr;

A3 is His, D-His, Asn, D-Asn, Arg, D-Arg, L-His(π-Me), D-His(π-Me), L-His(τ-Me), or D-His(τ-Me);

A4 is Phe, D-Phe, Leu, D-Leu, Ile, D-Ile, Trp, D-Trp, Tyr, D-Tyr, Phg, bhPhe, Dpa, Bip, 1Nal, 2Nal, bhDpa, Amc, PheF5, hPhe, Igl, or cyclohexylalanine;

A5 is Pro, D-Pro, Ser, D-Ser, Oic, bhPro, trans-4-PhPro, cis-4-PhPro, cis-5-PhPro, or Idc;

A6 is Arg, L-Nω,ω-dimethyl-arginine, L-homoarginine, L-norarginine, citrulline, or N-MeArg;

A7 is Cys, D-Cys, Ser, D-Ser, Ala, D-Ala, Cys(S-tBut), homoCys, Pen, (D)Pen, S-tertiary butyl-cysteine, Cys(S-S-Pal), Cys(S-S-cysteamine-Pal), Cys(S-S-Cys-NHPal), or Cys(S-S-Cys);

A8 is Arg, L-Nω,ω-dimethyl-arginine, L-homoarginine, L-norarginine, citrulline, or N-MeArg;

A9 is Phe, D-Phe, Leu, D-Leu, Ile, D-Ile, Tyr, D-Tyr, Trp, D-Trp, Phe-$R^a$, D-Phe-$R^a$, Dpa-$R^a$, D-Dpa-$R^a$, Trp-$R^a$, bhPhe-$R^a$, PheF5, N-MePhe, benzylamide, 2-aminoindane, bhPhe, Dpa, Bip, 1Nal, 2Nal, bhDpa, or cyclohexylalanine, which may or may not have $R^a$ linked thereto, wherein $R^a$ is palmitoyl-PEG- wherein PEG is PEG11 or miniPEG3, palmitoyl-PEG-PEG11, palmitoyl-PEG-miniPEG3, butanoyl (C4)-PEG11-, octanoyl (C8, Caprylic)-PEG11-, palmitoyl (C16)-PEG11-, or tetracosanoyl (C24, Lignoceric)-PEG11-; and A10 is Cys, D-Cys, Ser, D-Ser, Ala, D-Ala, Ida, Ahx-Ida(NHPal), or Ahx-Ida(NBzl2);

wherein the carboxy-terminal amino acid is in amide or carboxy-form;

wherein at least one sulfhydryl amino acid is present as one of the amino acids in the sequence; and wherein A1, A1 to A2, A10, or a combination thereof are optionally absent, and wherein bhAsp is 3-aminopentanedioic acid Ida is 2,2'-azanediyldiacetic acid;

Ida(NHPal) is a palmitylamine amide on Ida side chain;

Ida(NBzl2) is N,N'-Dibenzylamine amide on Ida side chain;

N-MeAsp is methyl-L-aspartic acid;

Ahx is aminohexanoic acid;

Tle is L-tert-leucine;

Inp is isonipecotic acid;

Chg is L-α-cyclohexylglycine;

bhThr is β-homothreonine;

N-MeThr is (2S)-3-hydroxy-2-(methylamino)butanoic acid;

His(π-Me) is $N^π$-methylhistidine;

His(τ-Me) is $N^τ$-methylhistidine;

Phg is L-phenylglycine;

bhPhe is β-homophenylalanine;

Dpa is 3,3-diphenyl-L-alanine;

Bip is L-biphenylalanine;

1Nal is (1-naphthyl)-L-alanine;

2Nal is (2-naphthyl)-L-alanine;

bhDpa is (S)-3-Amino-4,4-diphenylbutanoic acid;

Amc is 4-(aminomethyl)cyclohexane carboxylic acid;

PheF5 is (R)-2-amino-3-(perfluorophenyl)propanoic acid;

hPhe is (S)-2-amino-4-phenylbutanoic acid;

Igl is (S)-2-amino-2-(2,3-dihydro-1H-inden-2-yl)acetic acid;

Oic is octahydroindole-2-carboxylic acid;

bhPro is L-β-homoproline;

trans-4-PhPro is (2S,4S)-4-phenylpyrrolidine-2-carboxylic acid;

cis-4-PhPro is (2S,4R)-4-phenylpyrrolidine-2-carboxylic acid;

cis-5-PhPro is (2R,5S)-5-phenylpyrrolidine-2-carboxylic acid;

Idc is (R)-indoline-2-carboxylic acid;

Cys(S-tBut) is S-t-Butylthio-L-cysteine;

homoCys is L-homocysteine;

Pen is L-Penicillamine;

(D)Pen is D-Penicillamine;

Cys(S-S-Pal) is palmitoyl attached to Cys via a disufide bond;

Cys(S-S-cysteamine-Pal) is palmitoyl attached to Cys via SS-Cysteamine;

Cys(S-S-Cys-NHPal) is palmitylamine attached to Cys via another Cys;

Cys(S-S-Cys) is Cys attached to Cys via disulfide bond;

N-MeArg is $N^ω$-methyl-L-arginine;

PEG11 is O-(2-aminoethyl)-O'-(2-carboxyethyl)-undecaethyleneglycol; and miniPEG3 is 11-amino-3,6,9-trioxaundecanoic acid.

2. The peptide according to claim 1, wherein the peptide contains at least one of the following:

a) A1=N-MeAsp, Ida, or Ida(NHPal);

b) A5=bhPro;

c) A6=Arg, or N-MeArg;

d) A7=Cys(S-S-Pal), Cys(S-S-cysteamine-Pal), Cys(S-S-Cys-NHPal), or Cys(S-S-Cys); and/or e) A8=Arg, or N-MeArg.

3. The peptide according to claim 1, wherein:

i) when A1 is Ida and A9 is Phe, then A10 is not Ahx-Ida(NHPal);

ii) when A1 is Ida, A9 is not bhPhe-$R^b$, wherein $R^b$ is S-(palmityl)thioglycolic-PEG-;

iii) when A4 is D-Phe, A7 is not D-Cys(S-S-tBut) and A9 is not D-Trp-$R^c$, wherein $R^c$ is Butanoyl-PEG11-, Octanoyl-PEG11-, Palmitoyl-PEG11-, or Tetracosanoyl-PEG11-.

4. The peptide according to claim 1, wherein

A1 is D-Asp, N-MeAsp, Ida, or Ida(NHPal);

A2 is Thr or D-Thr;

A3 is His or D-His;

A4 is Dpa or D-Dpa;

A5 is Pro, D-Pro, bhPro, or Oic;

A6 is Arg, or N-MeArg;

A7 is Cys, D-Cys, Cys(S-S-Pal), Cys(S-S-cysteamine-Pal), Cys(S-S-Cys-NHPal), or Cys(S-S-Cys);

A8 is Arg, or N-MeArg;

A9 is Phe, D-Phe, Dpa, D-Dpa, Trp, D-Trp, bhPhe, Phe-$R^a$, D-Phe-$R^a$, Dpa-$R^a$, D-Dpa-$R^a$ bhPhe-$R^a$, where in $R^a$ is palmitoyl-PEG- wherein PEG is PEG11 or miniPEG3, palmitoyl-PEG-PEG wherein PEG is PEG11 or miniPEG3, butanoyl (C4)-PEG11-, octanoyl (C8, Caprylic)-PEG11-, palmitoyl (C16)-PEG11-, or tetracosanoyl (C24, Lignoceric)-PEG11-; and A10, if present, is Ahx-Ida(NHPal) or Adx-Ida(NBzl2).

5. The peptide of according to claim 1, wherein the peptide is selected from the group consisting of:

Asp-Thr-His-Dpa-Pro-Arg-Cys-Arg-Dpa (SEQ ID NO: 67),

N-MeAsp-Thr-His-Dpa-Oic-Arg-Cys-Arg-bhPhe-R14 (SEQ ID NO: 77),

N-MeAsp-Thr-His-Dpa-bhPro-Arg-Cys-Arg-bhPhe-R14 (SEQ ID NO: 78),

Ida-Thr-His-Dpa-bhPro-Arg-Cys-Arg-bhPhe-R14 (SEQ ID NO: 82),

Ida-Thr-His-Dpa-bhPro-Arg-Cys-Arg-bhPhe-R15 (SEQ ID NO: 86),

Ida-Thr-His-Dpa-bhPro-Arg-Cys-Arg-bhPhe (SEQ ID NO:87),

Ida-Thr-His-Dpa-bhPro-Arg-Cys(S-S-Pal)-Arg-bhPhe (SEQ ID NO: 88),
Ida-Thr-His-Dpa-bhPro-Arg-Cys(S-S-cysteamine-Pal)-Arg-bhPhe (SEQ ID NO: 89),
Ida-Thr-His-Dpa-bhPro-Arg-Cys(S-S-Cys-NHPal)-Arg-bhPhe (SEQ ID NO: 90),
Ida-Thr-His-Dpa-bhPro-Arg-Cys(S-S-Cys)-Arg-bhPhe-R14 (SEQ ID NO: 91),
Ida(NHPal)-Thr-His-Dpa-bhPro-Arg-Cys-Arg-bhPhe (SEQ ID NO: 92),
Ida-Thr-His-Dpa-bhPro-Arg-Cys-Arg-bhPhe-Ida(NHPal) (SEQ ID NO:93),
Ida-Thr-His-Dpa-bhPro-Arg-Cys-Arg-bhPhe-Ahx-lda(NBzl2) (SEQ ID NO: 95), and
Ida-Thr-His-Dpa-bhPro-Arg-Cys-Arg-Trp-Ahx-Ida(NHPal) (SEQ ID NO: 101),
wherein
Ahx is an aminohexanoic acid spacer between peptide residue 9 and Ida residue;
R14 is Palmitoyl-PEG-miniPEG3-, and miniPEG3 is 11-amino-3,6,9-trioxaundecanoic acid; and
R15 is Palmitoyl-PEG-.

6. The peptide according to claim 1, wherein the peptide exhibits hepcidin activity.

7. The peptide according to claim 1, wherein the peptide binds ferroportin.

8. A composition which comprises at least one peptide according to claim 1.

9. A method of binding a ferroportin or inducing ferroportin internalization and degradation which comprises contacting the ferroportin with at least one peptide according to claim 1 or a composition comprising the at least one peptide.

10. A method of treating a disease of iron metabolism in a subject which comprises administering at least one peptide according to claim 1 or a composition comprising the at least one peptide to the subject.

11. The method of claim 10, wherein the disease of iron metabolism is an iron overload disease.

12. A kit comprising at least one peptide according to claim 1 or a composition comprising the at least one peptide packaged together with a reagent, a device, instructional material, or a combination thereof.

13. A complex comprising at least one peptide according to claim 1 bound to a ferroportin or an antibody.

14. The method according to claim 10, wherein the at least one peptide is administered at an effective daily dose as a single daily dose or as divided daily doses.

15. The method according to claim 14, wherein the effective daily dose is about 10-500 µg/kg/day and the at least one peptide is provided in a formulation for subcutaneous injection.

16. The method according to claim 14, wherein the effective daily dose is about 10-1000 µg/kg/day and the at least one peptide is provided in a formulation for oral, pulmonary, parenteral, or mucosal administration.

17. An isolated peptide having the following structural formula IA or IB $$A1-A2-A3-A4-A5-A6-A7-A8-A9-A10 \quad \text{IA}$$

$$A10-A9-A8-A7-A6-A5-A4-A3-A2-A1 \quad \text{IB}$$

wherein
A1 is Asp, D-Asp, Glu, D-Glu, pyroglutamate, D-pyroglutamate, Gln, D-Gln, Asn, D-Asn, bhAsp, Ida, Ida(NHPal), or N-MeAsp;
A2 is Thr, D-Thr, Ser, D-Ser, Val, D-Val, Ile, D-Ile, Ala, D-Ala, Tle, Inp, Chg, bhThr, or N-MeThr;
A3 is His, D-His, Asn, D-Asn, Arg, D-Arg, L-His(π-Me), D-His(π-Me), L-His(τ-Me), or D-His(τ-Me);
A4 is Phe, D-Phe, Leu, D-Leu, Ile, D-Ile, Trp, D-Trp, Tyr, D-Tyr, Phg, bhPhe, Dpa, Bip, 1Nal, 2Nal, bhDpa, Amc, PheF5, hPhe, Igl, or cyclohexylalanine;
A5 is Pro, D-Pro, Ser, D-Ser, Oic, bhPro, trans-4-PhPro, cis-4-PhPro, cis-5-PhPro, or Idc;
A6 is Arg;
A7 is Cys, D-Cys, Ser, D-Ser, Ala, D-Ala, Cys(S-tBut), homoCys, Pen, (D)Pen, S-tertiary butyl-cysteine, Cys(S-S-Pal), Cys(S-S-cysteamine-Pal), Cys(S-S-Cys-NHPal), or Cys(S-S-Cys);
A8 is Arg;
A9 is Phe, D-Phe, Leu, D-Leu, Ile, D-Ile, Tyr, D-Tyr, Trp, D-Trp, Phe-$R^a$, D-Phe-$R^a$, Dpa-$R^a$, D-Dpa-$R^a$, Trp-$R^a$, bhPhe-$R^a$, PheF5, N-MePhe, benzylamide, 2-aminoindane, bhPhe, Dpa, Bip, 1Nal, 2Nal, bhDpa, or cyclohexylalanine, which may or may not have $R^a$ linked thereto, wherein $R^a$ is palmitoyl-PEG- wherein PEG is PEG11 or miniPEG3, palmitoyl-PEG-PEG11, palmitoyl-PEG-miniPEG3, butanoyl (C4)-PEG11-, octanoyl (C8, Caprylic)-PEG11-, palmitoyl (C16)-PEG11-, or tetracosanoyl (C24, Lignoceric)-PEG11-; and
A10 is Cys, D-Cys, Ser, D-Ser, Ala, D-Ala, Ida, Ahx-Ida(NHPal), or Ahx-Ida(NBzl2);
wherein the carboxy-terminal amino acid is in amide or carboxy-form;
wherein at least one sulfhydryl amino acid is present as one of the amino acids in the sequence; and
wherein A1, A1 to A2, A10, or a combination thereof are optionally absent, and wherein
bhAsp is 3-aminopentanedioic acid
Ida is 2,2'-azanediyldiacetic acid;
Ida(NHPal) is a palmitylamine amide on Ida side chain;
Ida(NBzl2) is N,N'-Dibenzylamine amide on Ida side chain;
N-MeAsp is methyl-L-aspartic acid;
Ahx is aminohexanoic acid;
Tle is L-tert-leucine;
Inp is isonipecotic acid;
Chg is L-α-cyclohexylglycine;
bhThr is β-homothreonine;
N-MeThr is (2S)-3-hydroxy-2-(methylamino)butanoic acid;
His(π-Me) is $N^{\pi}$-methylhistidine;
His(τ-Me) is $N^{\tau}$-methylhistidine;
Phg is L-phenylglycine;
bhPhe is β-homophenylalanine;
Dpa is 3,3-diphenyl-L-alanine;
Bip is L-biphenylalanine;
1Nal is (1-naphthyl)-L-alanine;
2Nal is (2-naphthyl)-L-alanine;
bhDpa is (S)-3-Amino-4,4-diphenylbutanoic acid;
Amc is 4-(aminomethyl)cyclohexane carboxylic acid;
PheF5 is (R)-2-amino-3-(perfluorophenyl)propanoic acid;
hPhe is (S)-2-amino-4-phenylbutanoic acid;
Igl is (S)-2-amino-2-(2,3-dihydro-1H-inden-2-yl)acetic acid;
Oic is octahydroindole-2-carboxylic acid;
bhPro is L-β-homoproline;
trans-4-PhPro is (2S,4S)-4-phenylpyrrolidine-2-carboxylic acid;
cis-4-PhPro is (2S,4R)-4-phenylpyrrolidine-2-carboxylic acid;

cis-5-PhPro is (2R,5S)-5-phenylpyrrolidine-2-carboxylic acid;
Idc is (R)-indoline-2-carboxylic acid;
Cys(S-tBut) is S-t-Butylthio-L-cysteine;
homoCys is L-homocysteine;
Pen is L-Penicillamine;
(D)Pen is D-Penicillamine;
Cys(S-S-Pal) is palmitoyl attached to Cys via a disufide bond;
Cys(S-S-cysteamine-Pal) is palmitoyl attached to Cys via SS-Cysteamine;
Cys(S-S-Cys-NHPal) is palmitylamine attached to Cys via another Cys;
Cys(S-S-Cys) is Cys attached to Cys via disulfide bond;
N-MeArg is $N^\omega$-methyl-L-arginine;
PEG11 is O-(2-aminoethyl)-O'-(2-carboxyethyl)-undecaethyleneglycol; and
miniPEG3 is 11-amino-3,6,9-trioxaundecanoic acid.

18. An isolated peptide consisting of the following structural formula IA or IB

A1-A2-A3-A4-A5-A6-A7-A8-A9-A10    IA

A10-A9-A8-A7-A6-A5-A4-A3-A2-A1    IB wherein
A1 is Asp, D-Asp, Glu, D-Glu, pyroglutamate, D-pyroglutamate, Gln, D-Gln, Asn, D-Asn, bhAsp, Ida, Ida(NHPal), or N-MeAsp;
A2 is Thr, D-Thr, Ser, D-Ser, Val, D-Val, Ile, D-Ile, Ala, D-Ala, Tle, Inp, Chg, bhThr, or N-MeThr;
A3 is His, D-His, Asn, D-Asn, Arg, D-Arg, L-His($\pi$-Me), D-His($\pi$-Me), L-His($\tau$-Me), or D-His($\tau$-Me);
A4 is Phe, D-Phe, Leu, D-Leu, Ile, D-Ile, Trp, D-Trp, Tyr, D-Tyr, Phg, bhPhe, Dpa, Bip, 1Nal, 2Nal, bhDpa, Amc, PheF5, hPhe, Igl, or cyclohexylalanine;
A5 is Pro, D-Pro, Ser, D-Ser, Oic, bhPro, trans-4-PhPro, cis-4-PhPro, cis-5-PhPro, or Idc;
A6 is Arg;
A7 is Cys, D-Cys, Ser, D-Ser, Ala, D-Ala, Cys(S-tBut), homoCys, Pen, (D)Pen, S-tertiary butyl-cysteine, Cys(S-S-Pal), Cys(S-S-cysteamine-Pal), Cys(S-S-Cys-NHPal), or Cys(S-S-Cys);
A8 is Arg;
A9 is Phe, D-Phe, Leu, D-Leu, Ile, D-Ile, Tyr, D-Tyr, Trp, D-Trp, Phe-$R^a$, D-Phe-$R^a$, Dpa-$R^a$, D-Dpa-$R^a$, Trp-$R^a$, bhPhe-$R^a$, PheF5, N-MePhe, benzylamide, 2-aminoindane, bhPhe, Dpa, Bip, 1Nal, 2Nal, bhDpa, or cyclohexylalanine, which may or may not have $R^a$ linked thereto, wherein $R^a$ is palmitoyl-PEG- wherein PEG is PEG11 or miniPEG3, palmitoyl-PEG-PEG11, palmitoyl-PEG-miniPEG3, butanoyl (C4)-PEG11-, octanoyl (C8, Caprylic)-PEG11-, palmitoyl (C16)-PEG11-, or tetracosanoyl (C24, Lignoceric)-PEG11-; and
A10 is Cys, D-Cys, Ser, D-Ser, Ala, D-Ala, Ida, Ahx-Ida(NHPal), or Ahx-Ida(NBzl2);
wherein the carboxy-terminal amino acid is in amide or carboxy-form;
wherein at least one sulfhydryl amino acid is present as one of the amino acids in the sequence; and
wherein A1, A1 to A2, A10, or a combination thereof are optionally absent, and wherein
bhAsp is 3-aminopentanedioic acid
Ida is 2,2'-azanediyldiacetic acid;
Ida(NHPal) is a palmitylamine amide on Ida side chain;
Ida(NBzl2) is N,N'-Dibenzylamine amide on Ida side chain;
N-MeAsp is methyl-L-aspartic acid;
Ahx is aminohexanoic acid;
Tle is L-tert-leucine;
Inp is isonipecotic acid;
Chg is L-α-cyclohexylglycine;
bhThr is β-homothreonine;
N-MeThr is (2S)-3-hydroxy-2-(methylamino)butanoic acid;
His($\pi$-Me) is $N^\pi$-methylhistidine;
His($\tau$-Me) is $N^\tau$-methylhistidine;
Phg is L-phenylglycine;
bhPhe is β-homophenylalanine;
Dpa is 3,3-diphenyl-L-alanine;
Bip is L-biphenylalanine;
1Nal is (1-naphthyl)-L-alanine;
2Nal is (2-naphthyl)-L-alanine;
bhDpa is (S)-3-Amino-4,4-diphenylbutanoic acid;
Amc is 4-(aminomethyl)cyclohexane carboxylic acid;
PheF5 is (R)-2-amino-3-(perfluorophenyl)propanoic acid;
hPhe is (S)-2-amino-4-phenylbutanoic acid;
Igl is (S)-2-amino-2-(2,3-dihydro-1H-inden-2-yl)acetic acid;
Oic is octahydroindole-2-carboxylic acid;
bhPro is L-β-homoproline;
trans-4-PhPro is (2S,4S)-4-phenylpyrrolidine-2-carboxylic acid;
cis-4-PhPro is (2S,4R)-4-phenylpyrrolidine-2-carboxylic acid;
cis-5-PhPro is (2R,5S)-5-phenylpyrrolidine-2-carboxylic acid;
Idc is (R)-indoline-2-carboxylic acid;
Cys(S-tBut) is S-t-Butylthio-L-cysteine;
homoCys is L-homocysteine;
Pen is L-Penicillamine;
(D)Pen is D-Penicillamine;
Cys(S-S-Pal) is palmitoyl attached to Cys via a disufide bond;
Cys(S-S-cysteamine-Pal) is palmitoyl attached to Cys via SS-Cysteamine;
Cys(S-S-Cys-NHPal) is palmitylamine attached to Cys via another Cys;
Cys(S-S-Cys) is Cys attached to Cys via disulfide bond;
N-MeArg is $N^\omega$-methyl-L-arginine;
PEG11 is O-(2-aminoethyl)-O'-(2-carboxyethyl)-undecaethyleneglycol; and
miniPEG3 is 11-amino-3,6,9-trioxaundecanoic acid.

* * * * *